(12) United States Patent
Raza et al.

(10) Patent No.: US 11,186,877 B2
(45) Date of Patent: Nov. 30, 2021

(54) TERMINAL ERYTHROID DIFFERENTIATION AS A BIOMARKER FOR PROGNOSIS AND TREATMENT, AND THERAPEUTIC TARGET IN MYELOID MALIGNANCIES

(71) Applicant: The Trustees of Columbia University in the City of New York, New York, NY (US)

(72) Inventors: Azra Raza, New York, NY (US); Abdullah Mahmood Ali, New York, NY (US); Naomi Galili, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 94 days.

(21) Appl. No.: 16/223,942

(22) Filed: Dec. 18, 2018

(65) Prior Publication Data

US 2019/0187159 A1 Jun. 20, 2019

Related U.S. Application Data

(60) Provisional application No. 62/608,070, filed on Dec. 20, 2017.

(51) Int. Cl.
*C12Q 1/6886* (2018.01)

(52) U.S. Cl.
CPC ...... *C12Q 1/6886* (2013.01); *C12Q 2600/112* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

2006/0024692 A1* 2/2006 Nakamura ........... C12Q 1/6886
435/6.12

OTHER PUBLICATIONS

Jha et al Scientific Reports. Nov. 2016. 6: 37099, p. 1-13 (Year: 2016).*

(Continued)

*Primary Examiner* — Carla J Myers
(74) *Attorney, Agent, or Firm* — Leason Ellis LLP

(57) ABSTRACT

The present invention relates to utilizing terminal erythroid differentiation (TED) as a biomarker for prognosis and as a therapeutic target in myeloid malignancies, in particular myelodysplastic syndromes. The present invention relates to identifying patients with myelodysplastic syndromes at risk for poor survival/outcomes who would benefit from aggressive treatment, by characterizing their TED profile using protein and gene expression markers and combinations thereof.

2 Claims, 27 Drawing Sheets
(25 of 27 Drawing Sheet(s) Filed in Color)

(56) References Cited

OTHER PUBLICATIONS

Affymetrix NetAffx, available via URL: <affymetrix.com/analysis/netaffx/showresults.affx., printed on Dec. 8, 2020, 3 pages (Year: 2020).*

Bejar et al. Validation of a prognostic model and the impact of mutations in patients with lower-risk myelodysplastic syndromes. J Clin Oncol. Sep. 20, 2012;30(27):3376-3382.

Chang et al. Asynchronous synthesis of erythrocyte membrane proteins. Proc Natl Acad Sci U S A. Sep. 1976;73(9):3206-3210.

Chen et al. Resolving the distinct stages in erythroid differentiation based on dynamic changes in membrane protein expression during erythropoiesis. Proc Natl Acad Sci U S A. Oct. 13, 2009;106(41):17413-17418.

Greenberg et al. Revised international prognostic scoring system for myelodysplastic syndromes. Blood. Sep. 20, 2012;120(12):2454-2465.

Gronowicz et al. Maturation of the reticulocyte in vitro. J Cell Sci. Oct. 1984;71:177-197.

Hanspal et al. Asynchronous synthesis of membrane skeletal proteins during terminal maturation of murine erythroblasts. Blood. Jul. 15, 1992;80(2):530-539.

Hu et al. Isolation and functional characterization of human erythroblasts at distinct stages: implications for understanding of normal and disordered erythropoiesis in vivo. Blood. Apr. 18, 2013;121(16):3246-3253.

Malcovati et al. SF3B1 mutation identifies a distinct subset of myelodysplastic syndrome with ring sideroblasts. Blood. Jul. 9, 2015;126(2):233-241.

Mangaonkar et al. Prognostic interaction between bone marrow morphology and SF3B1 and ASXL1 mutations in myelodysplastic syndromes with ring sideroblasts. Blood Cancer J. Feb. 12, 2018;8(2):18.

Patnaik et al. SF3B1 mutations are prevalent in myelodysplastic syndromes with ring sideroblasts but do not hold independent prognostic value. Blood. Jan. 12, 2012;119(2):569-572.

Peters et al. Changing patterns in cytoskeletal mRNA expression and protein synthesis during murine erythropoiesis in vivo. Proc Natl Acad Sci U S A. Jul. 1, 1992;89(13):5749-5753.

Shiozawa et al. Gene expression and risk of leukemic transformation in myelodysplasia. Blood. Dec. 14, 2017;130(24):2642-2653.

Wu et al. The clinical implication of SRSF2 mutation in patients with myelodysplastic syndrome and its stability during disease evolution. Blood. Oct. 11, 2012;120(15):3106-3111.

Zhang et al. Disease-associated mutation in SRSF2 misregulates splicing by altering RNA-binding affinities. Proc Natl Acad Sci U S A. Aug. 25, 2015;112(34):E4726-4734.

Pomares et al. Validation of the Low Risk Prognostic Scoring System (LR-PSS) in Patients with VERY Low, Low and Intermediate Risk IPSS-R Myelodysplastic Syndrome. Results from a Single Center. Blood. 2015;126(23):2902-2902.

Raza and Galil, The genetic basis of phenotypic heterogeneity in myelodysplastic syndromes. Nat Rev Cancer. Dec. 2012;12(12):849-859.

* cited by examiner

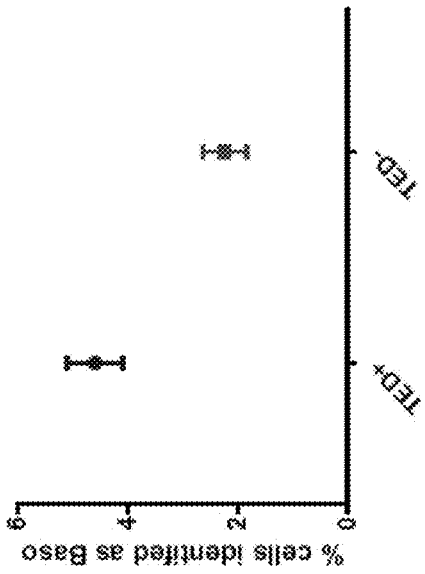
Figure 3B  Basonormoblast
P = 0.0030
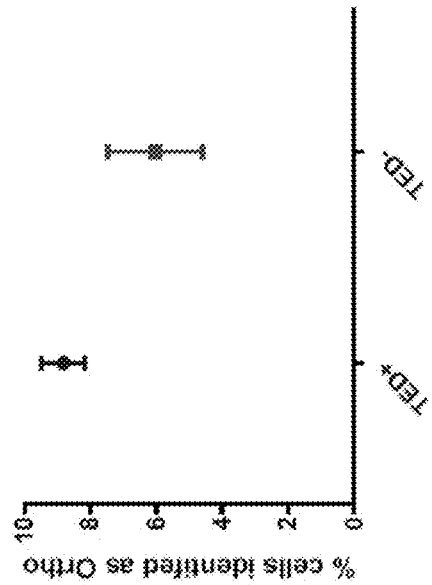
Figure 3D  Orthochromatic
P = 0.0051
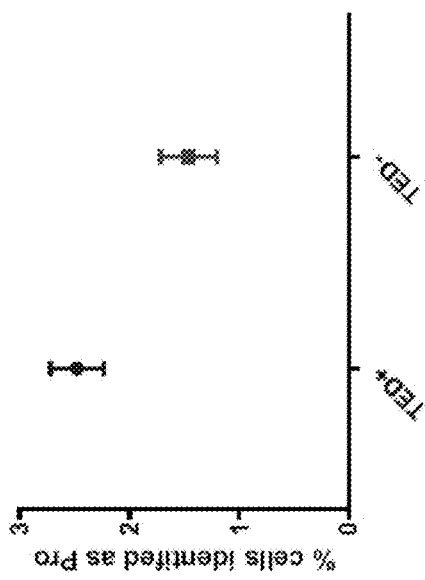
Figure 3A  Pronormoblast
P = 0.0609
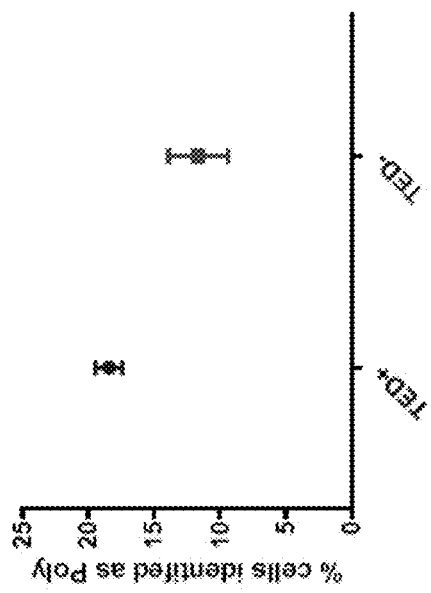
Figure 3C  Polychromatic
P = 0.0010

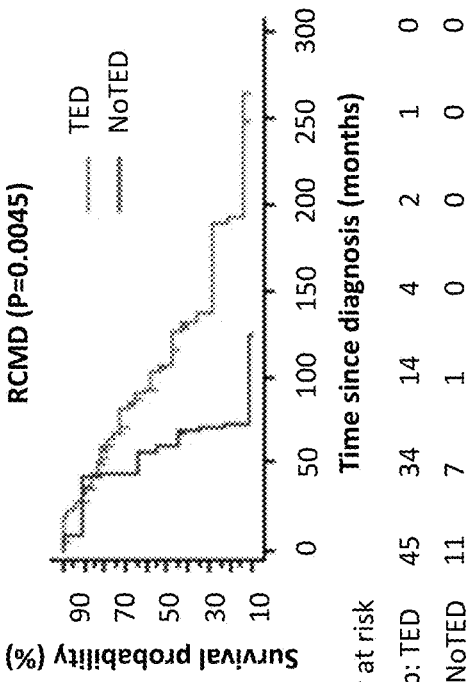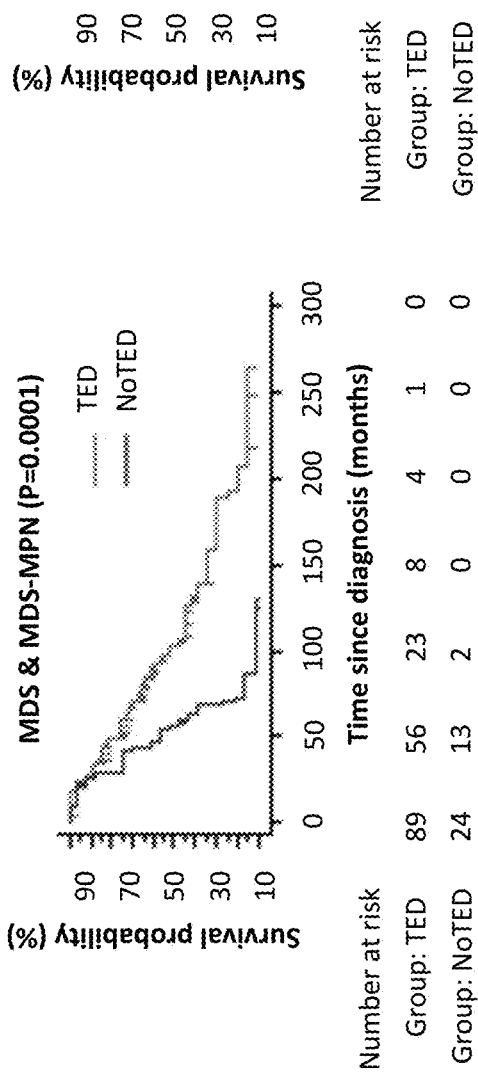

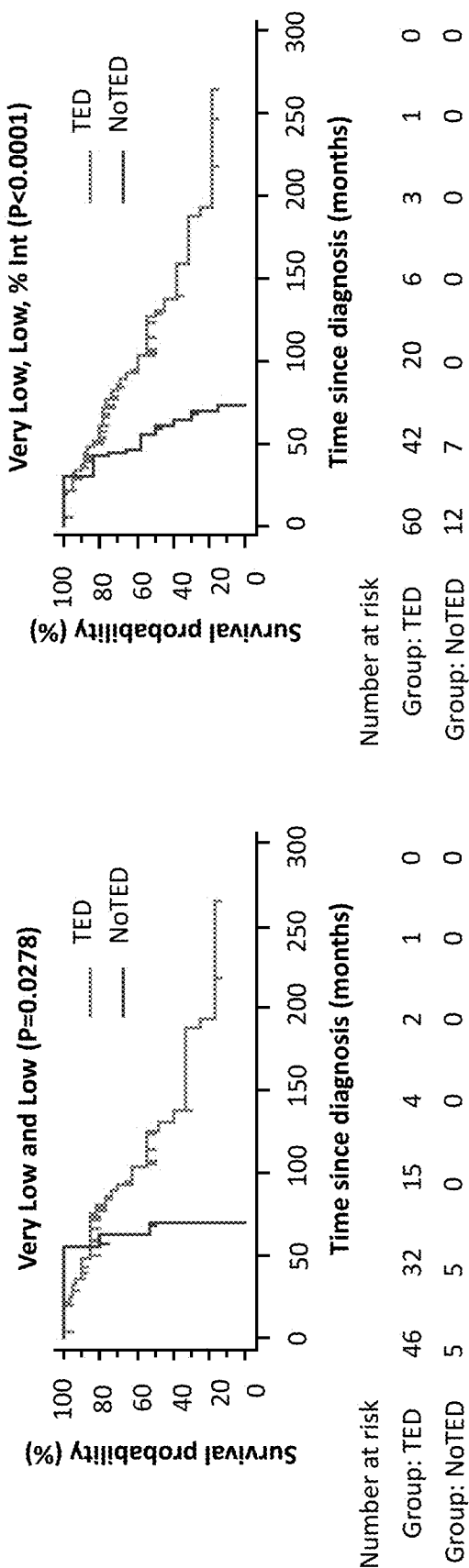

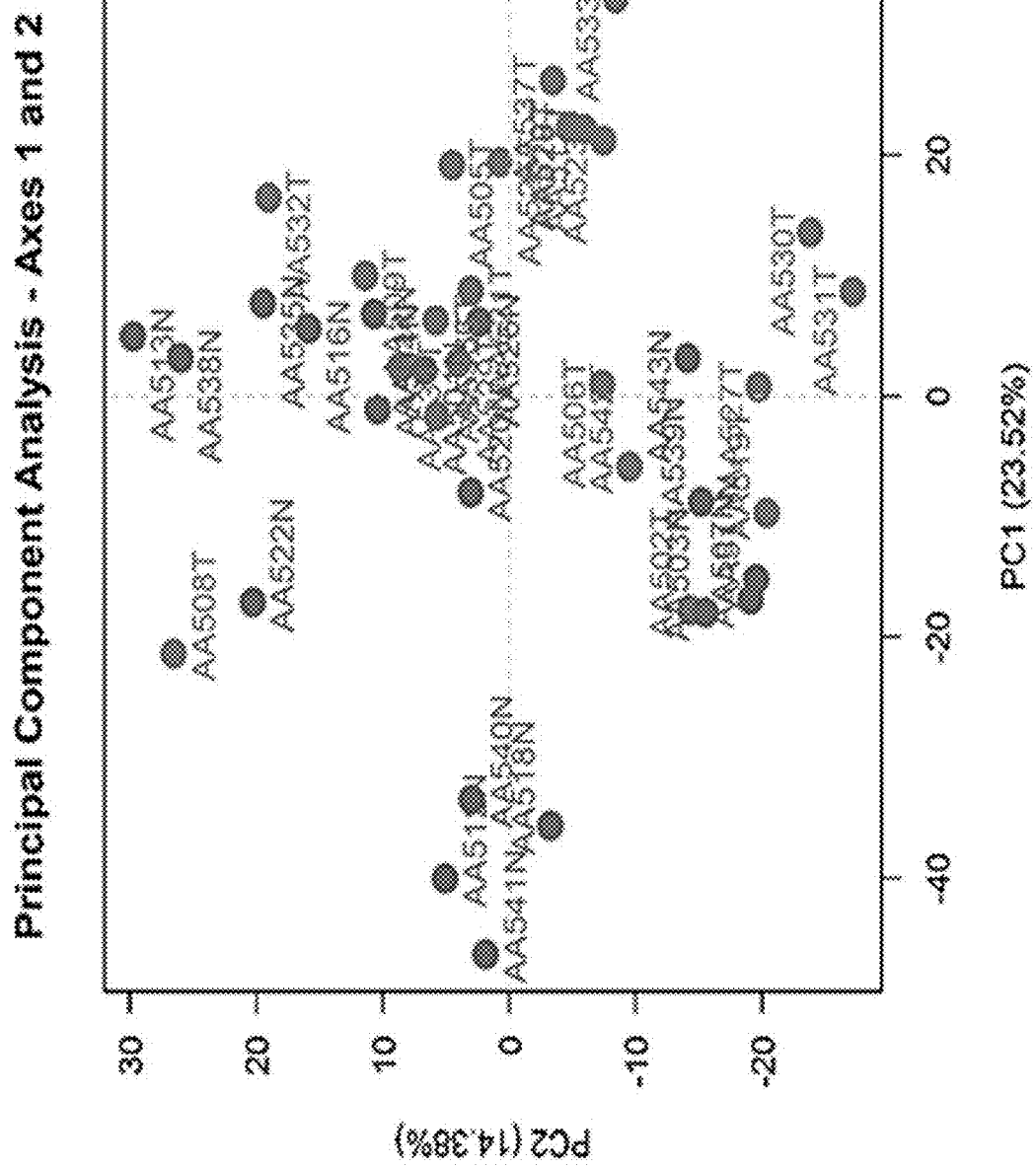

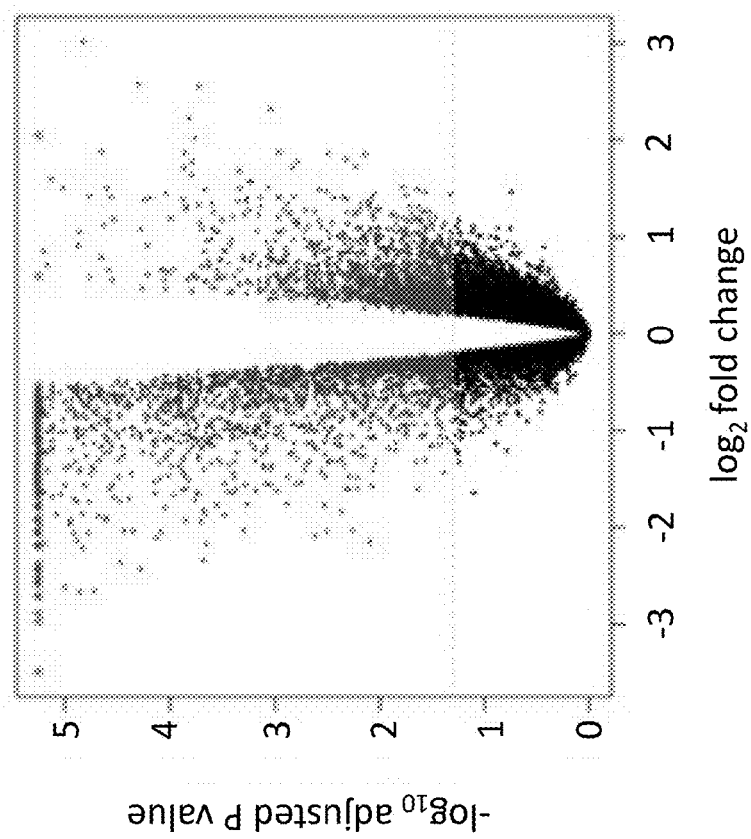
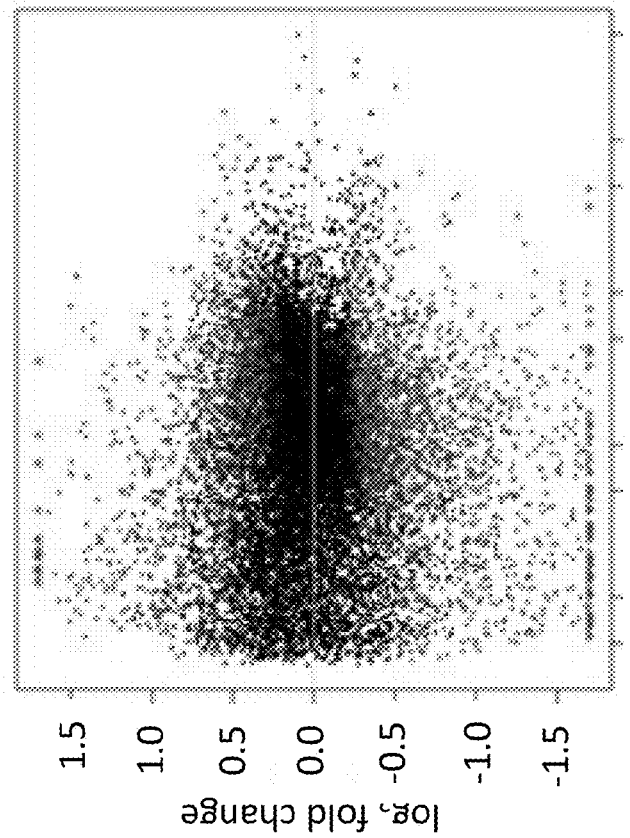
Figure 9B

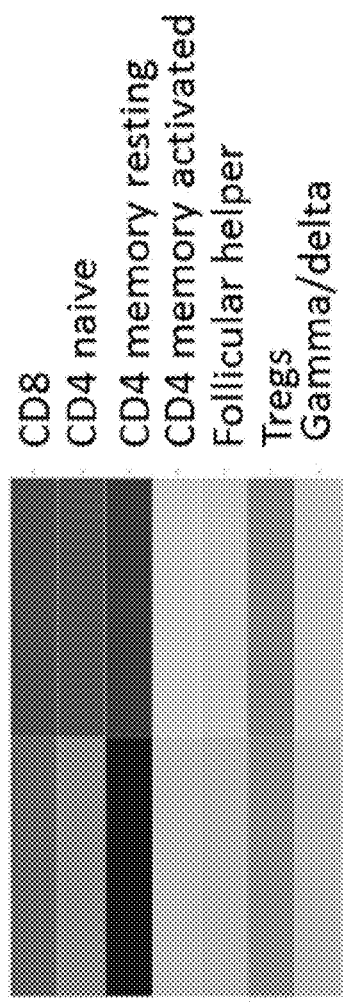
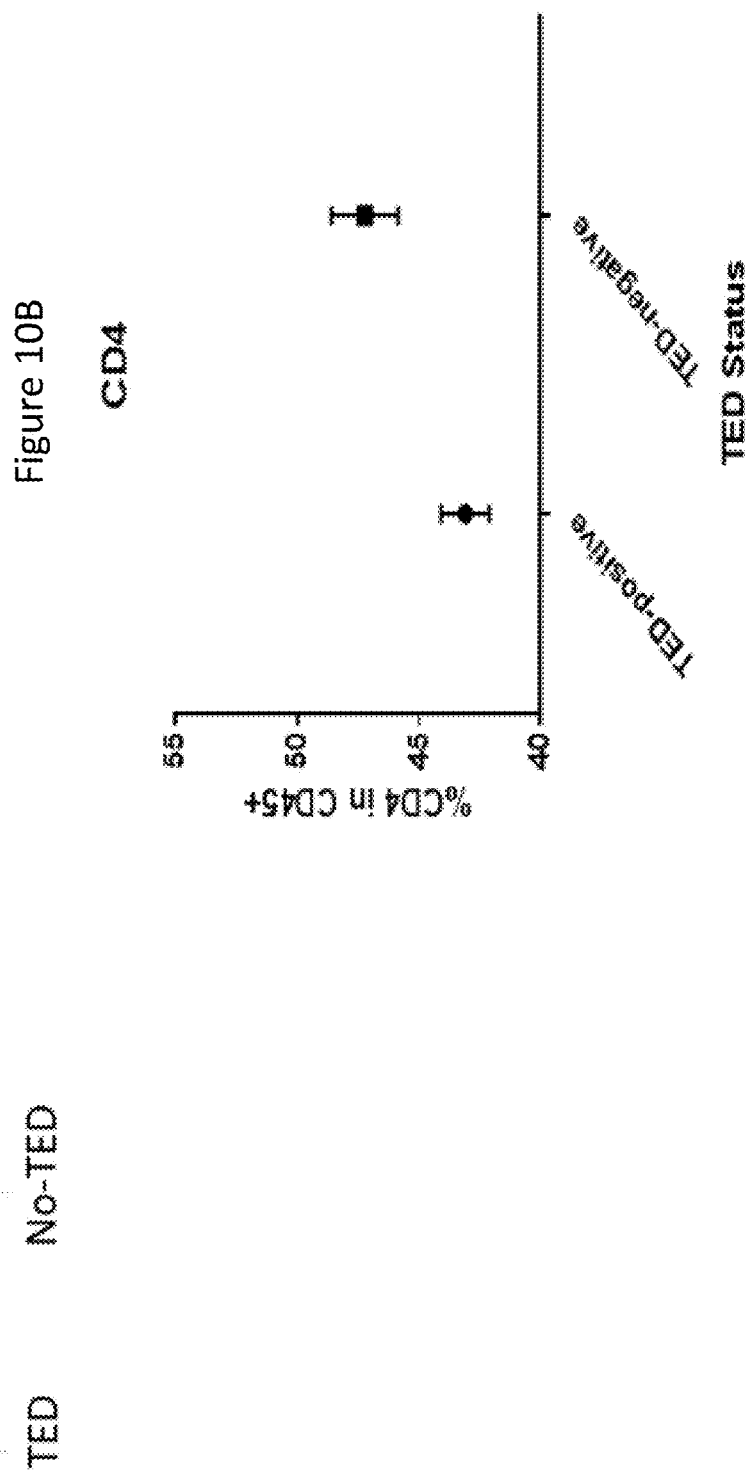
Figure 10A
Figure 10B

TERMINAL ERYTHROID DIFFERENTIATION AS A BIOMARKER FOR PROGNOSIS AND TREATMENT, AND THERAPEUTIC TARGET IN MYELOID MALIGNANCIES

CROSS REFERENCE TO RELATED APPLICATION

The present application claims priority to U.S. patent application Ser. No. 62/608,070 filed Dec. 20, 2017, which is hereby incorporated by reference in its entirety.

STATEMENT OF GOVERNMENT SUPPORT

This invention was made with government support under grant numbers DK100810 and DK32094 awarded by the National Institutes of Health. The government has certain rights in this invention.

FIELD OF THE INVENTION

The present invention relates to utilizing terminal erythroid differentiation (TED) as a biomarker for prognosis and as a therapeutic target in myeloid malignancies, in particular myelodyplastic syndromes. The present invention relates to identifying patients with myelodysplastic syndromes at risk for poor survival/outcomes who would benefit from aggressive treatment, by characterizing their TED profile.

BACKGROUND OF THE INVENTION

In a healthy person, bone marrow makes new, immature blood cells that mature over time. Myelodysplastic syndromes (MDS) occur when something disrupts this process so that the blood cells do not develop normally, look abnormal in shape, and die in the bone marrow or just after entering the bloodstream. Over time, there are not enough mature cells leading to problems such as fatigue caused by anemia, infections caused by leukopenia, and bleeding caused by thrombocytopenia.

Some myelodysplastic syndromes have no known cause. Others are caused by exposure to cancer treatments, such as chemotherapy and radiation, or to toxic chemicals, such as tobacco, benzene and pesticides, or to heavy metals, such as lead.

MDS are essentially incurable primary hematopoietic stem cell disorders except for the patients who receive allogeneic transplants (Raza and Galili 2012). The natural history of MDS is highly variable with survival ranging from months to decades. Moreover, a third of the patients progress to acute myeloid leukemia. Thus, several prognostic scoring systems were developed to predict clinical outcomes and to guide with treatment strategies. A combination of some or all of the several known patho-biologic features such as percentage of marrow blasts, degree of cytopenia, cytogenetic abnormalities, ringsideroblasts, and red cell transfusion requirement, were used to develop the most widely used prognostic scoring systems including the International Prognostic Scoring System (IPSS), the International Prognostic Scoring System-Revised (IPSS-R), and the WHO Prognostic Scoring System-Revised (WPSS). Identification of accurate prognostic variables is important and the IPSS-R is the most universally utilized prognostic classification (Greenberg et al. 2012). Other known factors, like age, transfusion dependence, serum ferritin levels, and beta-2 microglobulin concentration, were found to improve the prognostic value of the current widely used systems but they are not in practical use. Somatic mutations in several genes including SF3B1, SRSF2, U2AF1, TP53, EZH2, ETV6, or ASXL1 genes have been shown to have prognostic significance independent of the IPSS or IPSS-R but they are also of limited practical use.

Despite its general success, the IPSS-R has its limitations. For example, within the group of patients identified as having lower risk, MDS exists as at least three categories with distinct survival patterns ranging from 2.6 to 9.4 years and risk of transformation to acute myeloid leukemia (AML) ranging from 5% to 25% (Pomares et al. 2015). Hence, new biologic characteristics are needed that can independently predict outcome or improve the current prognostic scoring systems. Further refinement of the existing classification systems through the addition of mutational and gene expression profiling data is presently being attempted (Bejar et al. 2012; Shiozawa et al. 2017).

Thus, there is an urgent need for new markers and ways to identify patients with aggressive versus less severe myeloid malignancies.

SUMMARY OF THE INVENTION

The current invention solves the problem of identifying patients with MDS accurately as to prognosis and treatment strategies by identifying a terminal erythroid differentiation profile using a set of terminal erythroid differentiation (TED) biomarkers.

The TED biomarkers described herein provide not only a novel and unique way to definitively identify a MDS patient's prognosis, but provide targets for use in drug screening and basic research on MDS as well as other blood cancers, diseases, and disorders.

This study represents the first attempt to accurately quantify cells in various stages of TED from patients with MDS. Erythroid differentiation was profoundly abnormal across all MDS subtypes and absence of quantifiable cells undergoing TED by well-defined cell surface markers was strongly associated with inferior overall survival. Absence of quantifiable TED emerged as a powerful independent prognostic marker of poor overall survival across all IPSS-R categories in MDS. Thus, the ability to identify and stratify patients who are at risk for poor survival early in treatment will provide an opportunity for more aggressive course of treatment and will improve outcomes and overall survival.

Thus, in certain embodiments, the present invention relates to identifying patients at risk for poor survival/outcomes by characterizing or detecting their TED profile. Thus, the absence of, lack of and/or reduction of quantifiable TED in a patient MDS sample indicates a TED− or noTED profile and further indicates aggressive treatment options. In some embodiments, the TED profile is obtained from the patient early in treatment.

A TED profile can be obtained by assessing cells for at least one of the following or a combination of: protein cell surface markers including but not limited to glycophorin A (GPA), band 3 and α4 integrin; mutations in genes including but not limited to TET2, SF3B1, DNMT3A, SRSF2, and ASXL1; the downregulated expression of genes including but not limited to HBM, SCL2A1, SLC25A37, HEMGN, SLC4A1, TFRC, BLVRB, AHSP, PRDX2, HMBS, GATA1, KLF1, TAL1, ZFPM1, and LMO2; and the differential expression of genes including but not limited to those listed in Table 19.

A TED profile of a patient by assessing one of more of the above identifies a patient as having quantifiable TED denoted as TED+ or TED, or having the absence, lack of and/or reduction of quantifiable TED, denoted as TED− or noTED.

Thus, one embodiment of the current invention is a method and/or assay for detecting a terminal erythroid differentiation (TED) profile in a subject with myelodyplastic syndrome, comprising:

a. assaying a sample from the subject for one or more protein markers chosen from the group consisting of glycophorin A (GPA), band-3 and α4-integrin, and combinations thereof;

b. comparing the level of glycophorin A (GPA), band-3, and α4-integrin with a reference value of the same protein; and c. detecting that the subject has a TED profile associated with poor prognosis (TED−) when the level of glycophorin A (GPA) and band-3 is decreased from the subject as compared to the reference value and/or the level of α4-integrin is increased as compared to the reference value.

A further embodiment of the current invention is a method and/or assay for detecting a terminal erythroid differentiation (TED) profile in a subject with myelodyplastic syndrome, comprising:

a. anaylzing mutations in one or more genes chosen from the group consisting of TET2, SF3B1, DNMT3A, SRSF2, and ASXL1 in a sample from the subject with myelodyplastic syndrome;

b. comparing the mutations in the genes with mutations in the same genes that are indicative of a TED+ profile;

c. detecting mutations in the genes that is different from a TED+ profile and further detecting that the subject has MDS with a poor prognosis and/or lower survival outcome.

A further embodiment of the current invention is a method and/or assay for detecting a terminal erythroid differentiation (TED) profile in a subject with myelodyplastic syndrome, comprising:

a. assaying gene expression levels of one or more genes chosen from the group consisting of HBM, SCL2A1, SLC25A37, HEMGN, SLC4A1, TFRC, BLVRB, AHSP, PRDX2, HNBS, GATA1, KLF1, TAL1, ZFPM1, and LMO2 in a sample from the subject with myelodyplastic syndrome to obtain a test expression profile;

b. comparing the test expression profile of the genes with a reference expression profile of the same genes wherein the reference expression profile comprises gene expression levels of the same genes that are indicative of a TED+ profile;

c. detecting gene expression levels of the genes in the test expression profile are lower than the gene expression levels of the same genes in the reference expression profile that is indicative of a TED+ profile and further detecting that the subject has MDS with a poor prognosis and/or lower survival outcome.

Yet a further embodiment of the current invention is a method and/or assay for detecting a terminal erythroid differentiation (TED) profile in a subject with myelodyplastic syndrome, comprising:

a. assaying gene expression levels of one or more genes chosen from the genes listed in Table 19 in a sample from the subject with myelodyplastic syndrome to obtain a test expression profile;

b. comparing the test expression profile of the genes with a reference expression profile of the same genes wherein the reference expression profile comprises gene expression levels of the same genes that are indicative of either: i) a TED+ profile or a TED− profile;

c. detecting gene expression levels of the genes in the test expression profile are different than the gene expression levels of the same genes in the reference expression profile that is indicative of a TED+ profile and/or detecting gene expression levels of the genes in the test expression profile that are the same as the gene expression levels of the same genes in the reference expression profile that is indicative of a TED− profile and further detecting that the subject has MDS with a poor prognosis and/or lower survival outcome.

In some embodiments, the genes listed in Table 19 with fold change in average expression between TED+ and TED− profiles ranging from 1.9 to 9.7 chosen from the group consisting of MICA, SELPLG, SLCO3A1, SUPT1B1, TMOD2, WIPF1, YPEL2, ZYX, ANTXR2, and KLHL6 are used in the method.

In a further embodiment, the current invention provides for a method and/or assay for detecting a TED profile in a subject with MDS using a combination of one or more of the following: the protein biomarkers chosen from the group consisting of glycophorin A (GPA), band-3 and α4-integrin and combinations thereof; the gene expression levels of one or more genes chosen from the group consisting of HBM, SCL2A1, SLC25A37, HEMGN, SLC4A1, TFRC, BLVRB, AHSP, PRDX2, HNBS, GATA1, KLF1, TAL1, ZFPM1, and LMO2; the gene expression levels of one or more genes chosen from the genes listed in Table 19; and mutations in one or more genes chosen from the group consisting of TET2, SF3B1, DNMT3A, SRSF2, and ASXL1.

In some embodiments, the sample is from the bone marrow.

In some embodiments, the reference value is an amount or a quantity of a particular protein or nucleic acid in a sample from a healthy control. In some embodiments, a reference value is an amount or a quantity of a particular protein or nucleic acid in a sample from a patient with MDS who is TED+. In some embodiments, a reference value is an amount or a quantity of a particular protein or nucleic acid in a sample from a patient with MDS who is TED−.

In some embodiments, a subject is treated when a TED− or noTED profile is detected. In some embodiments, the subject is treated with aggressive treatment or therapy. In some embodiments, the subject is treated with hypomethylating agents; immunodulatory agents; hematopoietic growth factors; cytokines; and combinations thereof; and/or a stem cell transplant or bone marrow transplant. In some embodiments, aggressive treatment is a stem cell transplant, a bone marrow transplant, administration of chemotherapeutic agents, hypomethylating agents, and combinations thereof.

In some embodiments, the subject has been recently diagnosed with myelodyplastic syndrome (MDS). In some embodiments, the subject has been previously treated for MDS.

In further embodiments, the current invention provides for a method of monitoring treatment of a subject comprising:

a. assaying a sample from the subject prior to treatment for one or more of the following to obtain a reference profile:

i. protein markers chosen from the group consisting of glycophorin A (GPA), band-3 and α4-integrin and combinations thereof;

ii. gene expression levels of one or more genes chosen from the group consisting of HBM, SCL2A1, SLC25A37, HEMGN, SLC4A1, TFRC, BLVRB, AHSP, PRDX2, HNBS, GATA1, KLF1, TAL1, ZFPM1, and LMO2;

iii. gene expression levels of one or more genes in Table 19; and iv. mutations in one or more genes chosen from the group consisting of TET2, SF3B1, DNMT3A, SRSF2, and ASXL1;

b. assaying a sample from the subject after treatment for the same protein markers and/or gene expression levels and/or gene mutations to obtain a test profile;

c. comparing the test profile to the reference profile; and d. detecting that treatment has been effective if the test profile has changed from the reference profile and the test profile is more similar to a TED+ profile.

In some embodiments, a reference value may also mean an amount or a quantity of a particular protein or nucleic acid in a sample from a patient at another time point in the disease and/or treatment.

Detecting the level of any of the proteins can be done by any method known in the art, including, but not limited to, flow cytometry, quantitative Western blot, immunoblot, quantitative mass spectrometry, enzyme-linked immunosorbent assays (ELISAs), radioimmunoassays (RIA), immunoradiometric assays (IRMA), and immunoenzymatic assays (IEMA) and sandwich assays using monoclonal and polyclonal antibodies.

Detecting the expression of any of the genes can be done by any method known in the art, including, but not limited to, microarrays; Southern blots; Northern blots; dot blots; primer extension; nuclease protection; subtractive hybridization and isolation of non-duplexed molecules using, for example, hydroxyapatite; solution hybridization; filter hybridization; amplification techniques such as RT-PCR and other PCR-related techniques such as PCR with melting curve analysis, and PCR with mass spectrometry; fingerprinting, such as with restriction endonucleases; and the use of structure specific endonucleases. mRNA expression can also be analyzed using mass spectrometry techniques (e.g., MALDI or SELDI), liquid chromatography, and capillary gel electrophoresis. Any additional method known in the art can be used to detect the presence or absence of the transcripts.

The current invention also provides for kits.

BRIEF DESCRIPTION OF THE DRAWINGS

For the purpose of illustrating the invention, there are depicted in drawings certain embodiments of the invention. However, the invention is not limited to the precise arrangements and instrumentalities of the embodiments depicted in the drawings.

The patent or application file contains at least one drawing executed in color. Copies of this patent or patent application publication with color drawing(s) will be provided by the Office upon request and payment of the necessary fee.

FIG. 1 shows flow cytometry profiles of MDS patients.

FIG. 2 shows results showing TED is abnormal in patient samples.

FIG. 3 shows the percentage of various erythroid lineage cells undergoing terminal erythroid differentiation as identified based on their morphology. FIG. 3A is a plot of pronormoblasts in TED+ and TED− cells. FIG. 3B is a plot of basonormoblasts in TED+ and TED− cells. FIG. 3C is a plot of polychromatic in TED+ and TED− cells. FIG. 3D is a plot of orthochromatic in TED+ and TED− cells. Cells were identified based on their morphology and reported in the manual differential count by pathologist, were analyzed using two-tailed unpaired Mann-Whitney test. There was significant different with all the four cells types low in TED-negative (n=17) group compared to TED-positive (n=85).

FIG. 5 are Kaplan-Meier survival curves generated to calculate overall survival (OS) among patients on whom TED profile was obtained (TED) compared to patients in whom sample was adequate but no cells were found undergoing TED (No TED). FIG. 5A is a survival curve for all patients, MDA (n=108) and RARS-T (n=6) (P=0.0001). FIG. 5B is a survival curve for RCMD group of patients (P=0.0045). FIG. 5E is a survival curve for patients classified as IPSS-R very low and low categories (P=0.0278). FIG. 5F is a survival curve for patients classified as IPSS-R very low, low, and intermediate categories (P<0.0001).

FIG. 6 are Kaplan-Meier survival curves generated to calculate overall survival (OS) among additional patients on whom TED profile was obtained (TED) compared to patients in whom sample was adequate but no cells were found undergoing TED (No TED).

FIG. 8 shows the variability within the experiment. FIG. 8B shows the Principal Component Analysis (PCA) of Variance Stabilizing Transformation (VST) of count data show clustering of TED (blue) and NoTED samples (red).

FIG. 9 shows the differential gene expression analysis. FIG. 9B shows the edgeR programs used to find differentially expressed gene (up=>0.5, down=<-0.5; padj<0.05) in NoTED compared to TED.

FIG. 10 shows enrichment of mRNA representing CD4 on NoTED samples. FIG. 10A shows Cibersort analysis revealed an enrichment of mRNA representing CD4 gene signature in noTED samples. FIG. 10B shows the results of immunophenotyping using flow cytometry showed an enrichment of CD4+ cells in NoTED.

FIG. 11 are heatmaps.

FIG. 13 shows the use of 50 genes to classify TED.

DETAILED DESCRIPTION OF THE INVENTION

Figure 1A:
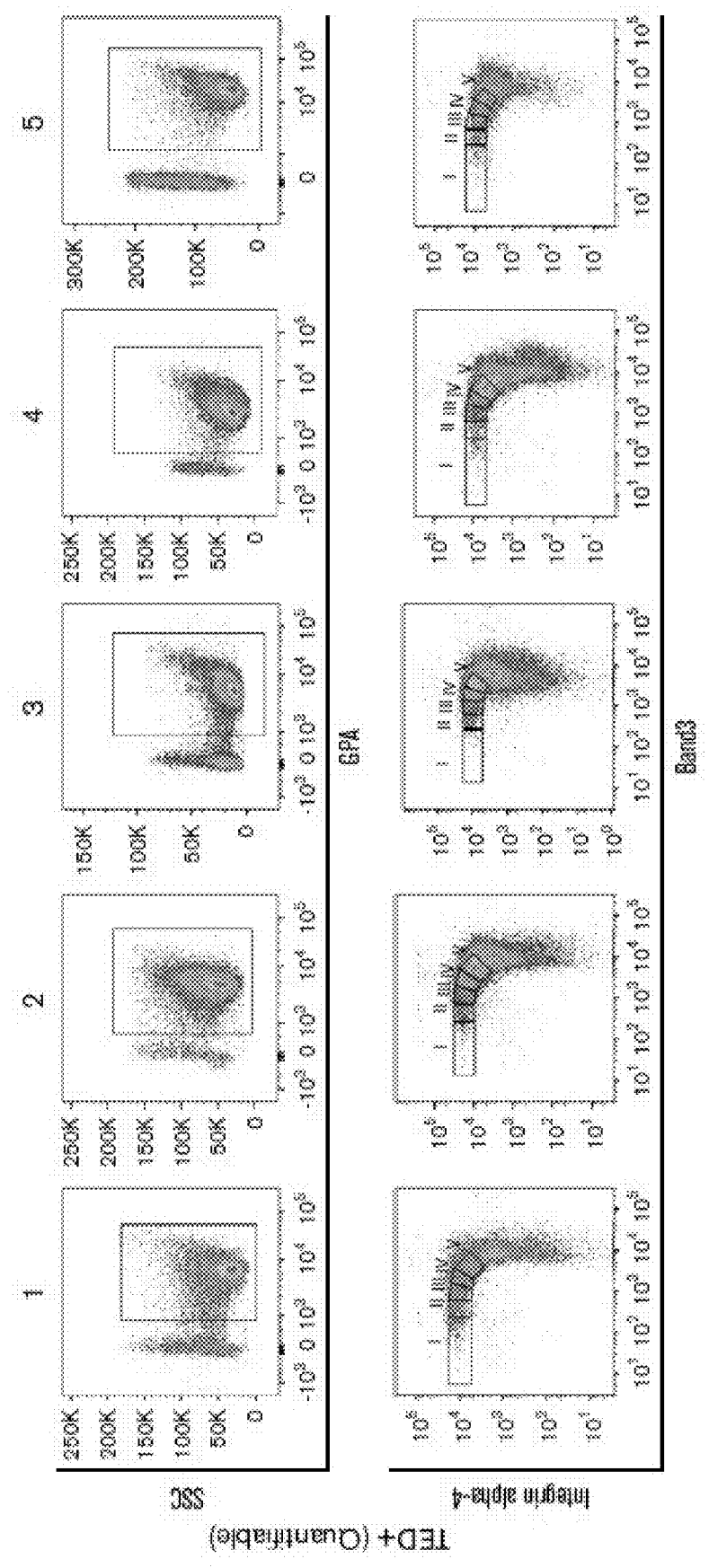
FIG. 1A are representative dot-plots of terminal erythroid differentiation profiles, as observed on flow cytometry, obtained from primary human bone marrow of MDS samples from five quantifiable samples.

This present disclosure identifies terminal erythroid differentiation (TED), the process by which precursor cells become mature red blood cells, as a clinically significant indicator for prognostic classification of MDS. Specifically, the proteins GPA, band-3 and α4-integrin can be used to track and quantify the number of cells undergoing TED, where the absence of TED is linked to worse patient outcomes. This technology associates TED with known mutations in MDS, and demonstrates that this marker can also serve as an indicator for bone marrow failure. Moreover, protein markers for TED, as well as their upstream and downstream protein clients, may also be promising therapeutic targets for treatment of anemia.

The present disclosure also identifies mutations in specific genes as well as the differential expression of specific genes as markers of the absence of TED.

This technology has the potential to improve MDS treatment by increasing the accuracy of MDS prognosis and facilitating the development of new targeted therapeutics.

Definitions

The terms used in this specification generally have their ordinary meanings in the art, within the context of this invention and the specific context where each term is used. Certain terms are discussed below, or elsewhere in the specification, to provide additional guidance to the practitioner in describing the methods of the invention and how to use them. Moreover, it will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of the other synonyms. The use of examples anywhere in the specification, including examples of any terms discussed herein, is illustrative only, and in no way limits the scope and meaning of the invention or any exemplified term. Likewise, the invention is not limited to its preferred embodiments.

The term "subject" as used in this application means an animal with an immune system such as avians and mammals. Mammals include canines, felines, rodents, bovine, equines, porcines, ovines, and primates. Avians include, but are not limited to, fowls, songbirds, and raptors. Thus, the invention can be used in veterinary medicine, e.g., to treat companion animals, farm animals, laboratory animals in zoological parks, and animals in the wild. The invention is particularly desirable for human medical applications.

The term "patient" as used in this application means a human subject. In some embodiments of the present invention, the "patient" is diagnosed with MDS.

The terms "identification", "identify", "identifying" and the like as used herein means to recognize a disease state or a clinical manifestation or severity of a disease state in a subject or patient. The term also is used in relation to test agents and their ability to have a particular action or efficacy.

The terms "prediction", "predict", "predicting" and the like as used herein means to tell in advance based upon special knowledge.

The term "reference value" as used herein can mean an amount or a quantity of a particular protein or nucleic acid in a sample from a healthy control. A "reference value" may also mean an amount or a quantity of a particular protein or nucleic acid in a sample from a patient at another time point in the disease and/or treatment. A "reference value" may also mean an amount or a quantity of a particular protein or nucleic acid in a sample from a patient with MDS who is TED+. A "reference value" may also mean an amount or a quantity of a particular protein or nucleic acid in a sample from a patient with MDS who is TED− or noTED.

The term "reference expression profile" as used herein can mean a gene expression profile from a sample from a healthy control. A "reference expression profile" may also mean a gene expression profile from a sample from a patient at another time point in the disease and/or treatment. A "reference expression profile" may also mean a gene expression profile from a sample from a patient with MDS who is TED+. A "reference expression profile" may also mean a gene expression profile from a sample from a patient with MDS who is TED− or noTED.

The term "healthy control" is a human subject who is not suffering from MDS.

The terms "treat", "treatment", and the like refer to a means to slow down, relieve, ameliorate or alleviate at least one of the symptoms of the disease, or reverse the disease after its onset.

The terms "prevent", "prevention", and the like refer to acting prior to overt disease onset, to prevent the disease from developing or minimize the extent of the disease or slow its course of development.

The term "agent" as used herein means a substance that produces or is capable of producing an effect and would include, but is not limited to, chemicals, pharmaceuticals, biologics, small organic molecules, antibodies, nucleic acids, peptides, and proteins.

The phrase "therapeutically effective amount" is used herein to mean an amount sufficient to cause an improvement in a clinically significant condition in the subject, or delays or minimizes or mitigates one or more symptoms associated with the disease, or results in a desired beneficial change of physiology in the subject.

As used herein, the term "isolated" and the like means that the referenced material is free of components found in the natural environment in which the material is normally found. In particular, isolated biological material is free of cellular components. In the case of nucleic acid molecules, an isolated nucleic acid includes a PCR product, an isolated mRNA, a cDNA, an isolated genomic DNA, or a restriction fragment. In another embodiment, an isolated nucleic acid is preferably excised from the chromosome in which it may be found. Isolated nucleic acid molecules can be inserted into plasmids, cosmids, artificial chromosomes, and the like. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated material may be, but need not be, purified.

The term "purified" and the like as used herein refers to material that has been isolated under conditions that reduce or eliminate unrelated materials, i.e., contaminants. For example, a purified protein is preferably substantially free of other proteins or nucleic acids with which it is associated in a cell; a purified nucleic acid molecule is preferably substantially free of proteins or other unrelated nucleic acid molecules with which it can be found within a cell. As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by chromatography, gel electrophoresis, immunoassay, composition analysis, biological assay, and other methods known in the art.

The terms "expression profile" or "gene expression profile" refers to any description or measurement of one or more of the genes that are expressed by a cell, tissue, or organism under or in response to a particular condition. Expression profiles can identify genes that are up-regulated, down-regulated, or unaffected under particular conditions. Gene expression can be detected at the nucleic acid level or at the protein level. The expression profiling at the nucleic acid level can be accomplished using any available technology to measure gene transcript levels. For example, the method could employ in situ hybridization, Northern hybridization or hybridization to a nucleic acid microarray, such as an oligonucleotide microarray, or a cDNA microarray. Alternatively, the method could employ reverse transcriptase-polymerase chain reaction (RT-PCR) such as fluorescent dye-based quantitative real time PCR (TaqMan® PCR). The expression profiling at the protein level can be accomplished using any available technology to measure protein levels, e.g., using peptide-specific capture agent arrays.

The terms "gene", "gene transcript", and "transcript" are used somewhat interchangeable in the application. The term "gene", also called a "structural gene" means a DNA sequence that codes for or corresponds to a particular sequence of amino acids which comprise all or part of one or more proteins or enzymes, and may or may not include regulatory DNA sequences, such as promoter sequences, which determine for example the conditions under which the gene is expressed. Some genes, which are not structural genes, may be transcribed from DNA to RNA, but are not translated into an amino acid sequence. Other genes may function as regulators of structural genes or as regulators of DNA transcription. "Transcript" or "gene transcript" is a sequence of RNA produced by transcription of a particular gene. Thus, the expression of the gene can be measured via the transcript.

The term "genomic DNA" as used herein means all DNA from a subject including coding and non-coding DNA, and DNA contained in introns and exons.

A "polynucleotide" or "nucleotide sequence" is a series of nucleotide bases (also called "nucleotides") in a nucleic acid, such as DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and anti-sense polynucleotide. This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases, for example thio-uracil, thio-guanine and fluoro-uracil.

"Nucleic acid" refers to deoxyribonucleotides or ribonucleotides and polymers thereof in either single- or double-stranded form.

The term "polypeptide" as used herein means a compound of two or more amino acids linked by a peptide bond. "Polypeptide" is used herein interchangeably with the term "protein."

The term "about" or "approximately" means within an acceptable error range for the particular value as determined by one of ordinary skill in the art, which will depend in part on how the value is measured or determined, i.e., the limitations of the measurement system, i.e., the degree of precision required for a particular purpose, such as a pharmaceutical formulation. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

Molecular Biology

In accordance with the present invention, there may be numerous tools and techniques within the skill of the art, such as those commonly used in molecular immunology, cellular immunology, pharmacology, and microbiology. See, e.g., Sambrook et al. (2001) Molecular Cloning: A Laboratory Manual. 3rd ed. Cold Spring Harbor Laboratory Press: Cold Spring Harbor, N.Y.; Ausubel et al. eds. (2005) Current Protocols in Molecular Biology. John Wiley and Sons, Inc.: Hoboken, N.J.; Bonifacino et al. eds. (2005) Current Protocols in Cell Biology. John Wiley and Sons, Inc.: Hoboken, N.J.; Coligan et al. eds. (2005) Current Protocols in Immunology, John Wiley and Sons, Inc.: Hoboken, N.J.; Coico et al. eds. (2005) Current Protocols in Microbiology, John Wiley and Sons, Inc.: Hoboken, N.J.; Coligan et al. eds. (2005) Current Protocols in Protein Science, John Wiley and Sons, Inc.: Hoboken, N.J.; and Enna et al. eds. (2005) Current Protocols in Pharmacology, John Wiley and Sons, Inc.: Hoboken, N.J.

ABBREVIATIONS

MDS—myelodysplastic syndrome
BM—bone marrow
OS—overall survival
TED—terminal erythroid differentiation
TED+—undergoing identifiable TED
TED- or noTED—not undergoing identifiable TED
RA—refractory anemia
RARS—refractory anemia with ringed sideroblasts
RCMD—refractory cytopenia with multilineage dyplasia
RCMD-RS—refractory cytopenia with multilineage dyplasia and ringed sideroblasts
RAEB—refractory anemia with excess blasts
RAEB-T—refractory anemia in transformation (RAEB-T).
MPN—myeloproliferative neoplasma
CMML—chronic myelomonocytic leukemia
IPSS—International Prognostic Scoring System
IPSS-R—International Prognostic Scoring System-Revised
WPSS—WHO Prognostic Scoring System-Revised Myelodysplastic Syndromes Myelodysplastic syndromes (MDS) as used herein, refers to a group of disorders caused by poorly formed blood cells or ones that do not work properly.

In certain embodiments, myelodysplastic syndrome or MDS is characterized by one or more of the following: ineffective blood cell production; progressive cytopenias; risk of progression to acute leukemia or cellular marrow with impaired morphology; and maturation (dysmyelopoiesis). The symptoms associated with MDS include, but are not limited to, anemia, thrombocytopenia, neutropenia, cytopenia, bicytopenia (two deficient cell types), and pancytopenia (three deficient cell types).

The World Health Organization divides myelodysplastic syndromes into subtypes based on the type of blood cells—red cells, white cells and platelets—involved. Myelodysplastic syndrome subtypes include:

Myelodysplastic syndrome with unilineage dysplasia. One blood cell type—white blood cells, red blood cells or platelets—is low in number and appears abnormal under the microscope.

Myelodysplastic syndrome with multilineage dysplasia. In this syndrome, two or three blood cell types are abnormal.

Myelodysplastic syndrome with ring sideroblasts. This type, which has two subtypes, involves a low number of one or more blood cell types. A characteristic feature is that existing red blood cells in the bone marrow contain a ring of excess iron called ring sideroblasts.

Myelodysplastic syndrome associated with isolated del chromosome abnormality. People with this syndrome have low numbers of red blood cells, and the cells have a specific mutation in their DNA.

Myelodysplastic syndrome with excess blasts—types 1 and 2. In both these syndromes, any of the three types of blood cells—red blood cells, white blood cells or platelets—might be low and appear abnormal under a microscope. Very immature blood cells (blasts) are found in the blood and bone marrow.

Myelodysplastic syndrome, unclassifiable. In this uncommon syndrome, there are reduced numbers of one of the three types of mature blood cells, and either the white blood cells or platelets look abnormal under a microscope.

Myelodysplastic syndromes may include refractory anemia (RA), RA with ringed sideroblasts (RARS), RA with excess blasts (RAEB), RAEB in transformation (RAEB-T), and chronic myelomonocytic leukemia (CMML).

Factors that can increase the risk of myelodysplastic syndromes include:

Older age. Most people with myelodysplastic syndromes are older than 60.

Treatment with chemotherapy or radiation. Chemotherapy or radiation therapy, both of which are commonly used to treat cancer, can increase your risk of myelodysplastic syndromes.

Exposure to certain chemicals. Chemicals linked to myelodysplastic syndromes include tobacco smoke, pesticides and industrial chemicals, such as benzene.

Exposure to heavy metals. Heavy metals linked to myelodysplastic syndromes include lead and mercury.

Complications of myelodysplastic syndromes include:

Anemia.

Recurrent infections.

Uncontrolled bleeding.

Increased risk of cancer.

Terminal Erythroid Differentiation (TED) is a Prognostic Marker in MDS

Erythroid differentiation is a complex cellular process that includes both early and terminal differentiation of erythroblasts. The early stage refers to a process by which pluripotent hematopoietic stem cells proliferate and differentiate into erythroid progenitors, erythroid burst-forming units (BFU-E) and then erythroid colony-forming units (CFU-E) that generate proerythroblasts. The proerythroblast undergoes 4-5 mitoses to produce reticulocytes by a process termed terminal erythroid differentiation (TED), consisting of five distinct phases-proerythroblasts (pros), early basophilic erythroblasts (EBs), late basophilic erythroblasts (LBs), polychromatic erythroblasts (polys), to orthochromatic erythroblasts (orthos) which upon enucleation generate reticulocytes (Hu et al. 2013). Each daughter cell is characterized by changes in expression of membrane proteins in that as the expression of major red cell membrane proteins increases, that of adhesion molecules decreases (Blikstad et al. 1983; Chang et al. 1976; Chen et al. 2009; Gronowicz et al. 1984; Hanspal et al. 1992; Liu and Mohandas 2011; Peter et al. 1992). By examining the dynamic changes in the expression of three salient marker proteins, glycophorin A (GPA), band 3 and α4 integrin, erythroblasts at distinct stages of their terminal differentiation were quantified in freshly obtained bone marrow (BM) samples, and successfully defined the stage-specific defects in morphologically and genetically well-defined subgroups of MDS patients. The resulting insights into the biology of MDS and the relationship of TED to mutational profiles and survival are reported here.

This study represents the first attempt to accurately quantify cells in various stages of TED from freshly obtained BM samples of patients with MDS and MDS/MPN overlap syndromes (RARS-T). One-third of the cases examined did not have quantifiable TED. TED-negative cases had a markedly shorter survival across all IPSS-R categories. In MDS patients, treatment choices, as well as the timing of intervention, are guided by an accurate assessment of prognosis, yet the risk of death, especially in the lower risk group, can be underestimated. The median survival for TED negative cases was significantly worse in both the lower (very low, low, and intermediate; median, 56 vs 126 months, P<0.0001) and higher risk (high and very high; median, 23 vs 48 months, P=0.0059) IPSS-R groups. Given that it remained a powerful independent variable for OS in a multivariable Cox regression model, assessment and quantification of TED by established erythroid cell surface markers can improve the prediction of prognosis within the various IPSS-R categories. Further striking associations emerged when these cases were found to be more frequently associated with mutations in SRSF2 and more profound anemia.

MDS patients with SRSF2 mutations have distinct clinical and biologic features in that they are older, more often male, and have an inferior OS (Wu et al. 2012). The inventors have previously reported that SRSF2 mutations cause subtle alterations in RNA-binding affinity and that the magnitude of splicing changes, as a result, is low consistent with the view that the pathogenesis of MDS is a slow process in which small effects of altered splicing gradually give rise to the disease phenotype by causing "death by a thousand cuts" (Zhang et al. 2015). In this study, a predominance of TED absence (7/23 unique patients) was identified in the SRSF2-mutated group.

Samples were collected over a period of 2.5 years; many patients during this time donated multiple marrow samples for TED studies. Although most patients (66%) showed a consistent TED outcome on repeat sampling, there were some inconsistent results. Variables influencing erythroid differentiation include treatment and natural evolution of the disease. Given that improvement in anemia and transfusion independence, among others, are two end points related to erythroid differentiation in any clinical trial on MDS patients, TED can be used to assess biological changes associated with response.

In conclusion, erythroid differentiation is profoundly abnormal across all MDS subtypes and absence of quantifiable cells undergoing TED by well-defined cell surface markers is strongly associated with inferior OS. Absence of quantifiable TED is more commonly associated with presence of SRSF2 mutations and emerged as a powerful independent prognostic marker of poor overall survival across all IPSS-R categories in MDS. Thus, the ability to identify and stratify patients who are at risk for poor survival early in treatment, will provide an opportunity for more aggressive course of treatment and will be expected to improve outcomes and overall survival.

The addition of this biologic marker to characterize hematopoietic defects in MDS has the potential to further refine the current prognostic classification systems.

The data presented herein shows that in 27% of MDS samples (56/205), there was no quantifiable TED (TED− or noTED) documented by surface expression of glycophorin A, α4 integrin and band 3 by terminally differentiating erythroblasts. Absence of quantifiable TED (TED− or noTED) was associated with a significantly worse overall survival (56 versus 103 months, P=0.0001) and SRSF2 mutations (7/23, P<0.05). In a multivariate Cox regression model, absence of TED (TED− or noTED) remained independently significant across International Prognostic Scoring System-Revised (IPSS-R) categories. In 149 of 205 MDS samples, the proportion of cells undergoing TED did not follow the expected 1:2:4:8:16 doubling pattern in successive stages.

Further data presented herein, shows mutations in certain genes in patients with a lack of TED (TED− or noTED), the downregulated expression of certain genes in patients with lack of TED (TED− or noTED) and the differential expression of certain genes in patients with a lack of TED (TED− or noTED).

Thus, in certain embodiments, the present invention relates to identifying patients at risk for poor survival/outcomes by characterizing or detecting their TED profile. Thus, the absence of, lack of and/or reduction of quantifiable TED in a patient MDS sample indicates a TED− or noTED profile and possible aggressive treatment options.

TED profile can be obtained by assessing cells for at least one of the following or a combination of: protein cell surface markers including but not limited to glycophorin A (GPA), band 3 and α4 integrin; mutations in gene including but not limited to HBM, SCL2A1, SLC25A37, HEMGN, SLC4A1, TFRC, BLVRB, AHSP, PRDX2, HNBS, TET2, SF3B1, DNMT3A, SRSF2, and ASXL1; the downregulated expression of GATA1, KLF1, TAL1, ZFPM1, and LMO2; and the differential expression of genes including but not limited to those listed in Table 19.

A TED profile of a patient by assessing one of more of the above identifies a patient as having quantifiable TED denoted as TED+ or TED, or having the absence, lack of and/or reduction of quantifiable TED, denoted as TED− or noTED.

Proteins Correlated to noTED and Assays and Methods to Detect Such Proteins

As stated above and shown in the Examples, certain protein markers are associated with the absence or lack of TED (TED− or NoTED) which in turn identifies a patient as having a more severe form of MDS. These markers include but are not limited to glycophorin A (GPA), band-3, and α4-integrin. The absence or reduced expression of the protein markers glycophorin A (GPA) and band-3, and increased expression of the protein marker α4-integrin denotes an absence or lack of TED (TED− or NoTED) and a more severe form of disease with worse outcomes.

By using these protein markers, important predictions and determinations can be made regarding the severity and treatment of a patient's disease. While tests for these biomarkers can be performed at any time after a diagnosis of MDS, preferably such tests would be performed as soon as possible after a positive diagnosis of MDS is made by a clinician. In that manner, the valuable insight into the disease can be utilized in choice of therapy.

The presence or amount of the protein markers can be compared to a reference value. In some embodiments, the reference value is from a healthy control. In some embodiments, the reference value is from a patient with MDS undergoing quantifiable TED. In some embodiments, the reference value is from a patient with MDS not undergoing quantifiable TED. In some embodiments, the reference value is from the subject themselves at another time point in the disease or treatment.

In certain embodiments, a sample of biological tissue or bodily fluid from a subject with MDS, is obtained.

In certain embodiments, the sample is tested for protein levels of one or more of the TED markers including but not limited to GPA, band-3, and α4-integrins. The protein sample can be obtained from any biological tissue. Preferred biological tissues include, but are not limited to, bone marrow, epidermal, whole blood, and plasma. The protein sample can be obtained from any biological fluid. Preferred fluids include, but are not limited to, plasma, serum, saliva, and urine.

The preferred biological tissue for the protein sample in bone marrow.

Protein can be isolated and/or purified from the sample using any method known in the art, including but not limited to immunoaffinity chromatography.

While any method known in the art can be used, preferred methods for detecting and measuring increase levels of the proteins in a protein sample include flow cytometry, quantitative Western blot, immunoblot, quantitative mass spectrometry, enzyme-linked immunosorbent assays (ELISAs), radioimmunoassays (RIA), immunoradiometric assays (IRMA), and immunoenzymatic assays (IEMA) and sandwich assays using monoclonal and polyclonal antibodies.

Antibodies are a preferred method of detecting and measuring target or desired proteins in a sample. Such antibodies are available commercially or can be made by conventional methods known in the art. Such antibodies can be monoclonal or polyclonal and fragments thereof, and immunologic binding equivalents thereof. The term "antibody" means both a homologous molecular entity as well as a mixture, such as a serum product made up of several homologous molecular entities.

In a preferred embodiment, such antibodies will immunoprecipitate the desired proteins from a solution as well as react with desired/target proteins on a Western blot, immunoblot, ELISA, and other assays listed above.

Antibodies for use in these assays can be labeled covalently or non-covalently with an agent that provides a detectable signal. Any label and conjugation method known in the art can be used. Labels, include but are not limited to, enzymes, fluorescent agents, radiolabels, substrates, inhibitors, cofactors, magnetic particles, and chemiluminescent agents. A number of fluorescent materials are known and can be utilized as detectable labels. These include, for example, fluorescein, rhodamine, auramine, Texas Red, AMCA blue and *Lucifer* Yellow. A particular detecting material is anti-rabbit antibody prepared in goats and conjugated with fluorescein through an isothiocyanate. Any desired targets or binding partner(s) can also be labeled with a radioactive element or with an enzyme. The radioactive label can be detected by any of the currently available counting procedures. The preferred isotope may be selected from $^{3}$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re. Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. In embodiments the enzymes can be are peroxidase, ß-glucuronidase, ß-D-glucosidase, ß-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

An alternative method for detection of the protein markers is to perform flow cytometry analysis on cells obtained from biological tissue or fluid from the subject. Preferred biological tissues include, but are not limited to, bone marrow, epidermal, whole blood, and plasma, with bone marrow most preferred. The protein sample can be obtained from any biological fluid. Preferred fluids include, but are not limited to, plasma, saliva, and urine. Again, the absence or reduced expression of protein markers band-3 and increased expression of α4-integrin denotes an absence or lack of TED (TED– or NoTED) and a more severe form of disease with worse outcomes.

Genetic Mutations Correlated to noTED and Assays and Methods to Detect Such Mutations As described herein, mutations in certain genes are correlated with a lack or absence of TED (TED– or NoTED) which in turn which in turn identifies a patient as having a more severe form of MDS. Mutations in genes including but not limited to TET2, SF3B1, DNMT3A, SRSF2, and ASXL1 denotes an absence or lack of TED and a more severe form of disease with worse outcomes.

By using the differential mutations in these genes, important predictions and determinations can be made regarding the severity and treatment of a patient's disease. While tests for these biomarkers can be performed at any time after a diagnosis of MDS, preferably such tests would be performed as soon as possible after a positive diagnosis of MDS is made by a clinician. In that manner, the valuable insight into the disease can be utilized in choice of therapy.

The presence of the gene mutations can be compared to a reference value. In some embodiments, the reference value is from a healthy control. In some embodiments, the reference value is from a patient with MDS undergoing quantifiable TED. In some embodiments, the reference value is from the subject themselves at another time point in the disease or treatment.

In certain embodiments, a sample of biological tissue or bodily fluid from a subject with MDS, is obtained.

Preferred biological tissues include, but are not limited to, bone marrow, whole blood, and plasma. The DNA protein sample can be obtained from any biological fluid. Preferred fluids include, but are not limited to, plasma, saliva, and urine.

The nucleic acid is extracted, isolated and purified from the cells of the tissue or fluid by methods known in the art.

If required, a nucleic acid sample are prepared using known techniques. For example, the sample can be treated to lyse the cells, using known lysis buffers, sonication, electroporation, with purification and amplification occurring as needed, as will be understood by those in the skilled in the art. In addition, the reactions can be accomplished in a variety of ways. Components of the reaction may be added simultaneously, or sequentially, in any order. In addition, the reaction can include a variety of other reagents which can be useful in the methods and assays and would include but is not limited to salts, buffers, neutral proteins, such albumin, and detergents, which may be used to facilitate optimal hybridization and detection, and/or reduce non-specific or background interactions. Also reagents that otherwise improve the efficiency of the assay, such as protease inhibitors, nuclease inhibitors, and anti-microbial agents, can be used, depending on the sample preparation methods and purity.

Once prepared, mRNA or other nucleic acids are analyzed by methods known to those of skill in the art. Mutational analysis is then performed for the genes. Mutational analysis can be done by any method known in the art including but not limited to polymerase chain reaction (PCR), DNA microarray, DNA sequencing, single stran conformational polymorphism, restriction length polymorphism, and next-generation sequencing.

Genes Correlated to noTED and Assays and Methods to Detect Such Genes

Also as described herein, differential expression in certain genes are correlated with a lack or absence of TED (TED– or NoTED) which in turn identifies a patient as having a more severe form of MDS.

By using the differential expression of these genes, important predictions and determinations can be made regarding the severity and treatment of a patient's disease. While tests for these biomarkers can be performed at any time after a diagnosis of MDS, preferably such tests would be performed as soon as possible after a positive diagnosis of MDS is made by a clinician. In that manner, the valuable insight into the disease can be utilized in choice of therapy.

Thus, one embodiment of the present invention, a test for the expression of one or more genes in Table 16 which include GATA1, KLF1, TAL1, ZFPM1, and LMO2 could be done. If one or more of the genes is downregulated, then the patient is identified as a TED– or noTED indicating a more severe disease and more aggressive treatment.

Figure 11A:
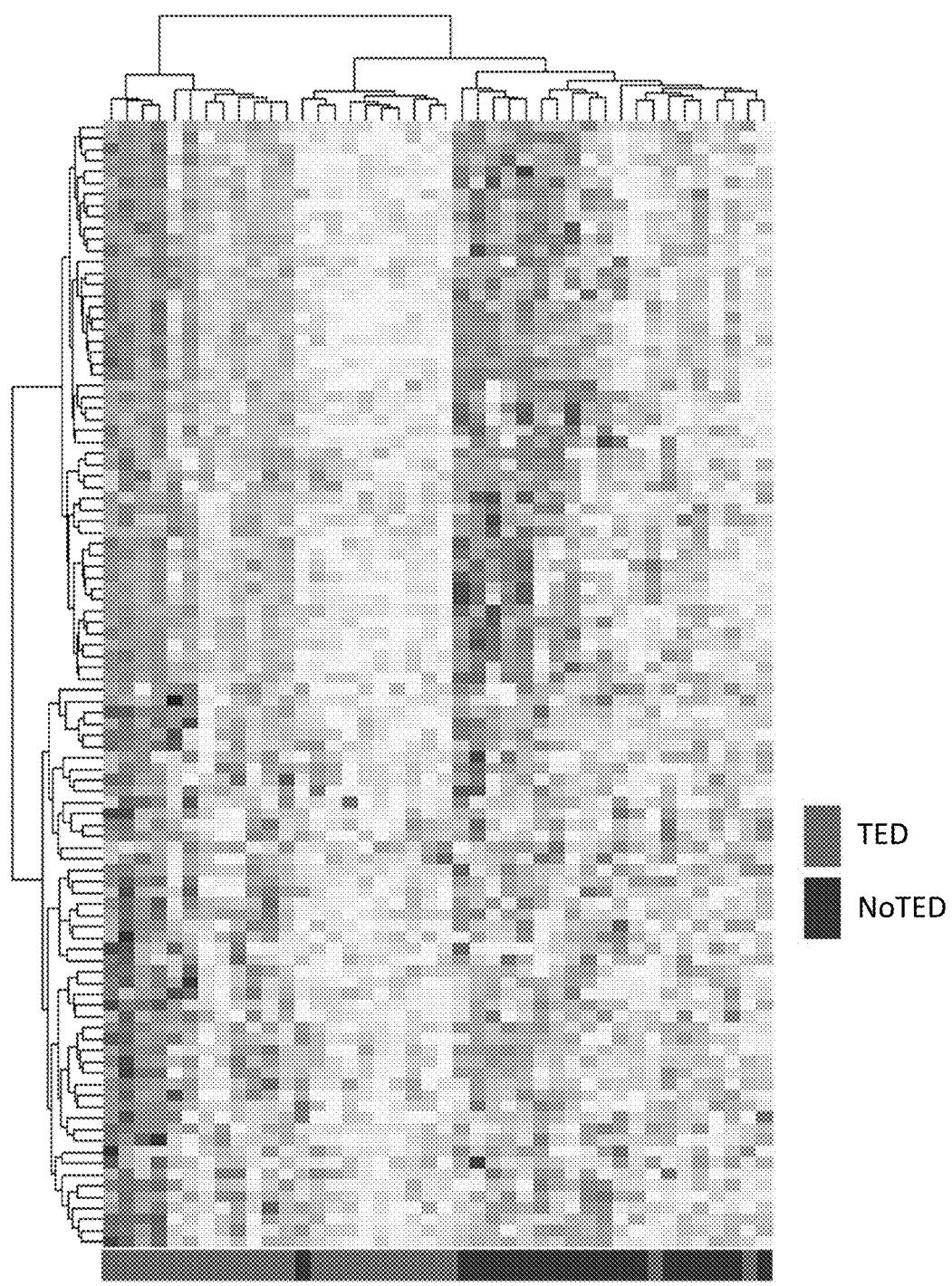
FIG. 11A is a heatmap of the top 50 up and 50 down expressed genes used to generated a heatmap and cluster the samples. The top 100 genes clustered TED and NoTED cases in two groups.
Figure 11B:
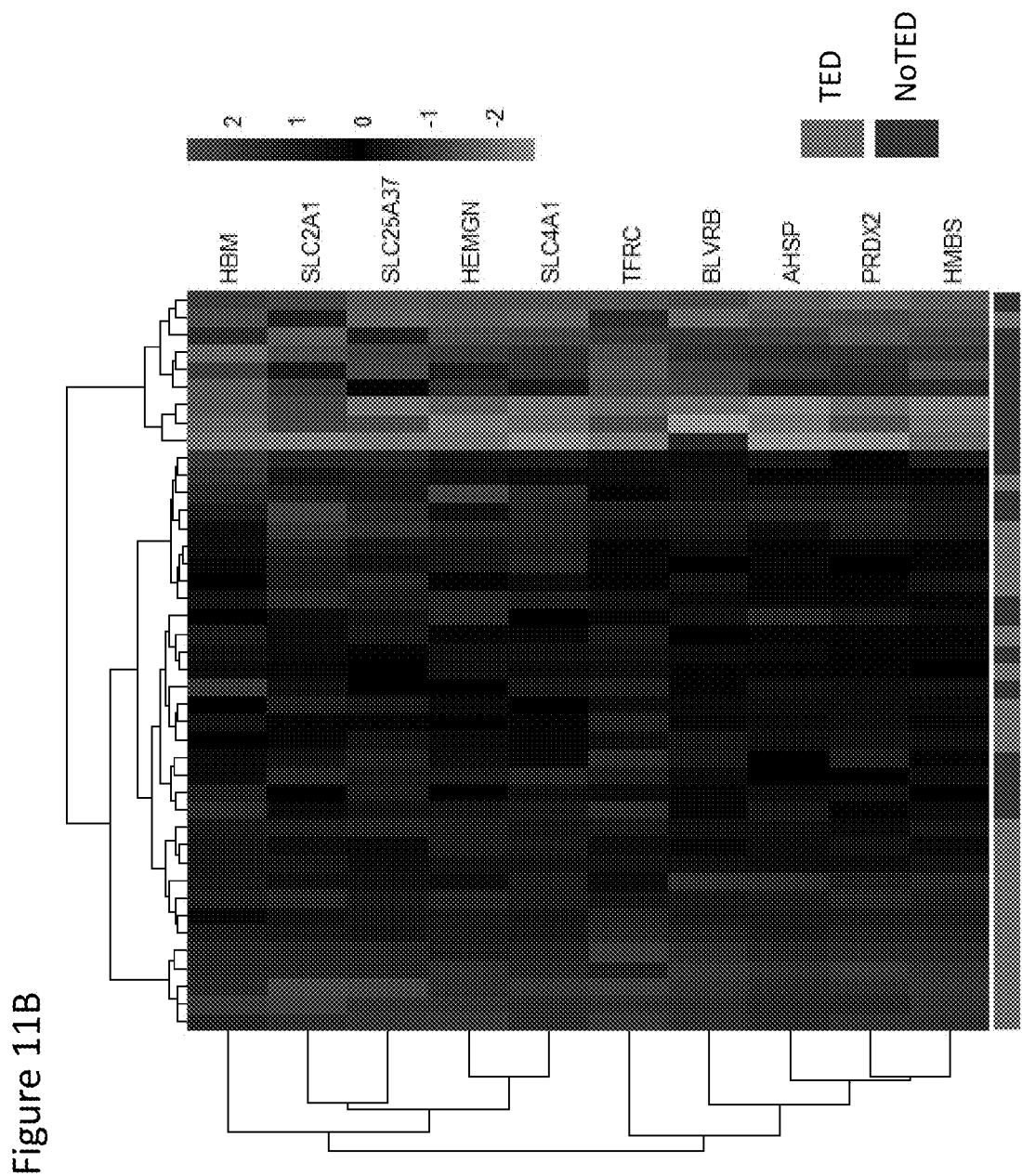
FIG. 11B is a heatmap of a 10 gene panel of genes that are highly expressed during TED that also cluster TED and NoTED samples.

A further embodiment of the present invention is a test for the expression of one or more genes in FIG. 11B which include HBM, SCL2A1, SLC25A37, HEMGN, SLC4A1, TFRC, BLVRB, AHSP, PRDX2, and HNBS could be done. If one or more of the genes is downregulated, then the patient is identified as a TED– or noTED indicating a more severe disease and more aggressive treatment.

A further embodiment of the present invention is a test for the expression of one or more of the 79 genes in Table 19. If one or more of the genes is differentially expressed from the average expression of the gene in the TED+ group or is expressed similarly to the gene in the TED– group, then the patient is identified as a TED– or NoTED indicating a more severe disease and more aggressive treatment.

Of the 76 gene listed in Table 19, 10 genes in particular have higher fold changes in average expression between TED+ and TED– profiles ranging from 1.9 to 9.7 (see Table 19). Thus in a further embodiment, the one or more of the genes chosen from the group consisting of MICA, SELPLG, SLCO3A1, SUPT1B1, TMOD2, WIPF1, YPEL2, ZYX, ANTXR2, and KLHL6 are used in the method.

The presence or amount of the gene expressions can be compared to a reference value. In some embodiments, the reference value is from a healthy control. In some embodiments, the reference value is from a patient with MDS undergoing quantifiable TED. In some embodiments, the reference value is from a patient with MDS not undergoing quantifiable TED. In some embodiments, the reference value is from the subject themselves at another time point in the disease or treatment.

In some embodiments, the reference value is set forth in Table 16. In some embodiments, the reference value is set forth in Table 19.

In certain embodiments, a sample of biological tissue or bodily fluid from a subject with MDS, is obtained.

Preferred biological tissues include, but are not limited to, bone marrow, epidermal, whole blood, and plasma, with bone marrow being the most preferred. The protein sample can be obtained from any biological fluid. Preferred fluids include, but are not limited to, plasma, saliva, and urine.

The nucleic acid is extracted, isolated and purified from the cells of the tissue or fluid by methods known in the art.

If required, a nucleic acid sample are prepared using known techniques. For example, the sample can be treated to lyse the cells, using known lysis buffers, sonication, electroporation, with purification and amplification occurring as needed, as will be understood by those in the skilled in the art. In addition, the reactions can be accomplished in a variety of ways. Components of the reaction may be added simultaneously, or sequentially, in any order. In addition, the reaction can include a variety of other reagents which can be useful in the methods and assays and would include but is not limited to salts, buffers, neutral proteins, such albumin, and detergents, which may be used to facilitate optimal hybridization and detection, and/or reduce non-specific or background interactions. Also reagents that otherwise improve the efficiency of the assay, such as protease inhibitors, nuclease inhibitors, and anti-microbial agents, can be used, depending on the sample preparation methods and purity.

Once prepared, mRNA or other nucleic acids are analyzed by methods known to those of skill in the art. In addition, when nucleic acids are to be detected preferred methods utilize cutting or shearing techniques to cut the nucleic acid sample containing the target sequence into a size that will facilitate handling and hybridization to the target. This can be accomplished by shearing the nucleic acid through mechanical forces, such as sonication, or by cleaving the nucleic acid using restriction endonucleases, or any other methods known in the art. However, in most cases, the natural degradation that occurs during archiving results in "short" oligonucleotides. In general, the methods and assays of the invention can be done on oligonucleotides as short as 20-100 base pairs, with from 20 to 50 being preferred, and between 40 and 50, including 44, 45, 46, 47, 48 and 49 being the most preferred.

Methods for examining gene expression, are often hybridization based, and include, Southern blots; Northern blots; dot blots; primer extension; nuclease protection; subtractive hybridization and isolation of non-duplexed molecules using, for example, hydroxyapatite; solution hybridization; filter hybridization; amplification techniques such as RT-PCR and other PCR-related techniques such as PCR with melting curve analysis, and PCR with mass spectrometry; fingerprinting, such as with restriction endonucleases; and the use of structure specific endonucleases. mRNA expression can also be analyzed using mass spectrometry techniques (e.g., MALDI or SELDI), liquid chromatography, and capillary gel electrophoresis. Any additional method known in the art can be used to detect the presence or absence of the transcripts.

For a general description of these techniques, see also Sambrook et al. 1989; Kriegler 1990; and Ausebel et al. 1990.

A preferred method for the detection of gene expression is the use of arrays or microarrays. These terms are used interchangeably and refer to any ordered arrangement on a surface or substrate of different molecules, referred to herein as "probes." Each different probe of any array is capable of specifically recognizing and/or binding to a particular molecule, which is referred to herein as its "target" in the context of arrays. Examples of typical target molecules that can be detected using microarrays include mRNA transcripts, cRNA molecules, cDNA, PCR products, and proteins.

Microarrays are useful for simultaneously detecting the presence, absence and quantity of a plurality of different target molecules in a sample. The presence and quantity, or absence, of the probe's target molecule in a sample may be readily determined by analyzing whether and how much of a target has bound to a probe at a particular location on the surface or substrate.

In a preferred embodiment, arrays used in the present invention are "addressable arrays" where each different probe is associated with a particular "address."

The arrays used in the present invention are preferable nucleic acid arrays that comprise a plurality of nucleic acid probes immobilized on a surface or substrate. The different nucleic acid probes are complementary to, and therefore can hybridize to, different target nucleic acid molecules in a sample. Thus, each probe can be used to simultaneously detect the presence and quantity of a plurality of different genes, e.g., the presence and abundance of different mRNA molecules, or of nucleic acid molecules derived therefrom (for example, cDNA or cRNA).

The arrays are preferably reproducible, allowing multiple copies of a given array to be produced and the results from each easily compared to one another. Preferably microarrays are small, and made from materials that are stable under binding conditions. A given binding site or unique set of binding sites in the microarray will specifically bind to the target. It will be appreciated that when cDNA complementary to the RNA of a cell is made and hybridized to a microarray under suitable conditions, the level or degree of hybridization to the site in the array corresponding to any particular gene will reflect the prevalence in the cell of mRNA transcribed from that gene. For example, when detectably labeled (e.g., with a fluorophore) cDNA complementary to the total cellular mRNA is hybridized to a microarray, the site on the array corresponding to a gene (i.e., capable of specifically binding a nucleic acid product of the gene) that is not transcribed in the cell will have little or no signal, while a gene for which mRNA is highly prevalent will have a relatively strong signal.

By way of example, GeneChip® (Affymetrix, Santa Clara, Calif.), generates data for the assessment of gene expression profiles and other biological assays. Oligonucleotide expression arrays simultaneously and quantitatively "interrogate" thousands of mRNA transcripts. Each transcript can be represented on a probe array by multiple probe pairs to differentiate among closely related members of gene families. Each probe contains millions of copies of a specific oligonucleotide probe, permitting the accurate and sensitive detection of even low-intensity mRNA hybridization patterns. After hybridization data is captured, using a scanner or optical detection systems, software can be used to automatically calculate the intensity values for each probe cell. Probe cell intensities can be used to calculate an average intensity for each gene, which correlates with mRNA abundance levels. Expression data can be quickly sorted based on any analysis parameter and displayed in a variety of graphical formats for any selected subset of genes.

Further examples of microarrays that can be used in the assays and methods of the invention are microarrays synthesized in accordance with techniques sometimes referred to as VLSIPS™ (Very Large Scale Immobilized Polymer Synthesis) technologies as described, for example, in U.S. Pat. Nos. 5,324,633; 5,744,305; 5,451,683; 5,482,867; 5,491,074; 5,624,711; 5,795,716; 5,831,070; 5,856,101; 5,858,659; 5,874,219; 5,968,740; 5,974,164; 5,981,185; 5,981,956; 6,025,601; 6,033,860; 6,090,555; 6,136,269; 6,022,963; 6,083,697; 6,291,183; 6,309,831; 6,416,949; 6,428,752 and 6,482,591.

Other exemplary arrays that are useful for use in the invention include, but are not limited to, Sentrix® Array or Sentrix® BeadChip Array available from Illumina®, Inc. (San Diego, Calif.) or others including beads in wells such as those described in U.S. Pat. Nos. 6,266,459; 6,355,431; 6,770,441; and 6,859,570. Arrays that have particle on the surface can also be used and include those described in U.S. Pat. Nos. 6,489,606; 7,106,513; 7,126,755; and 7,164,533.

An array of beads in a fluid format, such as a fluid stream of a flow cytometer or similar device, can also be used in methods for the invention. Exemplary formats that can be used in the invention to distinguish beads in a fluid sample using microfluidic devices are described, for example, in U.S. Pat. No. 6,524,793. Commercially available fluid formats for distinguishing beads include, for example, those used in XMAP™ technologies from Luminex or MPSS™ methods from Lynx Therapeutics.

A spotted microarray can also be used in a method of the invention. An exemplary spotted microarray is a CodeLink™ Array available from Amersham Biosciences.

Another microarray that is useful in the invention is one that is manufactured using inkjet printing methods such as SurePrint™ Technology available from Agilent Technologies. Other microarrays that can be used in the invention include, without limitation, those described in U.S. Pat. Nos. 5,429,807; 5,436,327; 5,561,071; 5,583,211; 5,658,734; 5,837,858; 5,919,523; 6,287,768; 6,287,776; 6,288,220; 6,297,006; 6,291,193; and 6,514,751.

Screening and diagnostic method of the current invention may involve the amplification of the target loci. A preferred method for target amplification of nucleic acid sequences is using polymerases, in particular polymerase chain reaction (PCR). PCR or other polymerase-driven amplification methods obtain millions of copies of the relevant nucleic acid sequences which then can be used as substrates for probes or sequenced or used in other assays.

Amplification using polymerase chain reaction is particularly useful in the embodiments of the current invention. PCR is a rapid and versatile in vitro method for amplifying defined target DNA sequences present within a source of DNA. Usually, the method is designed to permit selective amplification of a specific target DNA sequence(s) within a heterogeneous collection of DNA sequences (e.g. total genomic DNA or a complex cDNA population). To permit such selective amplification, some prior DNA sequence information from the target sequences is required. This information is used to design two oligonucleotide primers (amplimers) which are specific for the target sequence and which are often about 15-25 nucleotides long.

Methods of Treatment and Monitoring Treatment

Treatment for myelodysplastic syndromes usually focuses on reducing or preventing complications of the disease and its treatments. In some cases, treatment might involve chemotherapy or a bone marrow transplant.

A patient with MDS or at risk for MDS may be treated by therapies including, but not limited to, surgery, chemotherapy, immunotherapy (e.g., using monoclonal and/or polyclonal antibodies), biological therapy, radiation therapy, or other non-drug based therapy.

Agents for the treatment of MDS include: hypomethylating agents, including, but not limited to, 5-azacytidine, decitabine, and lenalidomide; other chemotherapeutic agents including but not limited to lenalidomide, cytarabine, daunorubicin, and idarubicin; hematopoietic growth factors and/or cytokines including but not limited to erythropoietin (EPO), granulocyte macrophage colony stimulating factor (GM-CSF), and granulocyte colony stimulating factor (G-CSF); hematopoietic cell dysplasia inhibitors; and immunotherapy including but not limited to monoclonal and polyclonal antibodies, particularly, therapeutic antibodies to cancer antigens and non-specific immunotherapies including but not limited to interferons and interleukins. Proteins that are particularly useful in the methods and compositions provided herein include proteins that stimulate the survival and/or proliferation of hematopoietic precursor cells and immunologically active poietic cells in vitro or in vivo. Other useful proteins stimulate the division and differentiation of committed erythroid progenitors in cells in vitro or in vivo. Particular proteins include, but are not limited to: interleukins, such as IL-2 (including recombinant IL-II ("rIL2") and canarypox IL-2), IL-10, IL-12, and IL-18; interferons, such as interferon α-2a, interferon α-2b, interferon α-n1, interferon α-n3, interferon β-Ia, and interferon γ-Ib; G-CSF and GM-CSF; and EPO.

The current invention provides methods for providing treatment based upon valid predictions as to the severity of MDS. In this manner, a subject diagnosed with MDS can be treated more effectively with agents that target the severity of the disease. Using the biomarkers provided herein for the first time allows clinicians and health care providers to tailor treatment more specifically based upon the profile of the patient.

A patient who has one or more markers associated with the lack of quantifiable TED (TED– or NoTED) be it a protein or gene marker or combination, would be treated with more aggressive treatment.

In certain embodiments, the aggressive course of treatment is stem cell transplantation.

In certain embodiments, the aggressive course of treatment is the administration of one or more chemotherapeutic agents combined with one or more hypomethylaing agents.

In certain embodiments, the aggressive course of treatment comprises bone marrow transplant.

In certain embodiments, the aggressive course of treatment is the administration of one or more hypomethylating agents, including, but not limited to, 5-azacytidine, decitabine, and lenalidomide.

In certain embodiments, the aggressive course of treatment is the administration of one or more chemotherapeutic agents including but not limited to lenalidomide, cytarabine, daunorubicin, and idarubicin.

In other embodiments, a patient found to have TED markers similar to a healthy control would be treated with less aggressive course of treatments including but not limited to platelet and/or blood transfusions, treatment with blood products and hematopoietic growth factors (e.g., erythropoietin) and/or one or more cytokines to stimulate blood cell development.

The current invention also provides methods for monitoring subjects and their responses to treatment, e.g, administration of agents, life style alterations such as diet and exercise, and non-traditional treatment. This is useful in both patient care as well as clinical trials. Such a method comprises obtaining the expression of at least one protein marker or gene or gene mutation that is a marker for TED in a subject prior to any treatment. After a course of treatment at a particular time period that a person of skill in the art can determine, the measurement of expression of the same protein marker or gene or gene mutation is measured, and a change of the measurement towards a reference value associated with quantifiable TED would indicate the agent is effectively treating or ameliorating the subject's MDS.

The present invention also provides a method for determining target genes or proteins for drug development.

Kits

It is contemplated that all of the methods and/or assays disclosed herein (e.g. components for determining the TED profile of a sample) can be in kit form for use by a health care provider and/or a diagnostic laboratory.

In certain embodiments, the present disclosure provides for a kit comprising one or more probes and/or one or more antibodies for detecting expression levels of one or more terminal erythroid differentiation (TED) markers as described herein.

Assays for the detection and quantitation of one or more of the protein biomarkers for TED can be incorporated into kits. Such kits may include antibodies that recognize the peptide of interest, reagents for isolating and/or purifying protein from a biological tissue or bodily fluid, reagents for performing assays on the isolated and purified protein, instructions for use, and reference values or the means for obtaining reference values for the quantity or level of peptides in a control sample.

Assays for the detection and quantitation of one or more of the gene biomarkers for TED can be incorporated into kits. Such kits may include probes for one or more of the genes from FIG. 11B, Table 16 and/or Table 19, as described herein, reagents for isolating and purifying nucleic acids from biological tissue or bodily fluid, reagents for performing assays on the isolated and purified nucleic acid, instructions for use, and reference values or the means for obtaining reference values in a control sample for the included genes.

A preferred embodiment of these kits would have the probes attached to a solid state. A most preferred embodiment would have the probes in a microarray format wherein nucleic acid probes for one or more of the genes from Table 16 and/or Table 19 would be in an ordered arrangement on a surface or substrate.

In some embodiments, a kit includes component to test both gene and protein markers of TED.

In a further embodiment of this invention, commercial test kits suitable for use by a medical specialist may be prepared to determine the presence or amount of a desired gene or protein activity, expression or gene amplification in samples from MDS patients.

In accordance with the above, an assay system for screening potential drugs effective to modulate the activity or expression of the target proteins or genes may be prepared and is provided. The target may be introduced into a test system, and the prospective drug may also be introduced into the resulting cell culture, and the culture thereafter examined to observe any changes in the target activity of the cells, or in the proliferation or division of the cells, due either to the addition of the prospective drug alone, or due to the effect of added quantities of the known target.

As referenced herein "target" can include any of the following: protein cell surface markers including but not limited to glycophorin A (GPA), band 3 and α4 integrin; mutations in gene including but not limited to TET2, SF3B1, DNMT3A, SRSF2, and ASXL1; the genes HBM, SCL2A1, SLC25A37, HEMGN, SLC4A1, TFRC, BLVRB, AHSP, PRDX2, HNBS, GATA1, KLF1, TAL1, ZFPM1, and LMO2; and differentially expressed genes including but not limited to those listed in Table 19.

EXAMPLES

This invention will be better understood from the Experimental Details, which follow. However, one skilled in the art will readily appreciate that the specific methods and results discussed are merely illustrative of the invention as described more fully in the claims that follow thereafter.

Example 1—Materials and Methods for Example 2-9

Informed consent was obtained from subjects who participated in the study approved by the Institutional Review Board of Columbia University and is in accordance with the Declaration of Helsinki. Samples were obtained from patients seen at New York Presbyterian Hospital/Columbia University Medical Center (NYP/CUMC) and from 16 normal individuals (The New York Presbyterian Cornell Hospital). World Health Organization (WHO) 2008 and IPSS-R were used in the classification of MDS patients. Ring sideroblasts (RS) were detected by Prussian Blue staining and counted by two clinicians. Cytogenetics were analyzed using standard G-banding. Clinical data were obtained via Columbia University Crown EMR and clinic records by researchers blinded to study results.

The details of age, sex, WHO, IPSS-R, myeloblast, RS, hemoglobin, platelets, absolute neutrophil count, myeloid/erythroid (M:E) ratio, and percentage of cells quantified in various stages of TED in patients are described in Table 1. Percentage of cells quantified in various stages of TED in normal individuals is provided in Table 2.

Sample Collection and Preparation for TED

BM aspirates were assayed for TED using a previously published method (Hu et al. 2013; Chen et al. 2009). Briefly, BM cells were separated on a Ficoll density gradient and incubated with CD45 microbeads for negative selection. $CD45^-$ cells were stained, analyzed and quantified as previously described. Each component of TED at distinct stages of development was evaluated using GPA, band 3 and α4 integrin. The selection of these three markers was based on a comprehensive analysis of membrane proteins that established the utility of these markers as necessary and sufficient for identifying various stages of TED in normal samples (Hu et al. 2013; Chang et al. 1976; Chen et al. 2009; Gronowicz et al. 1984; Hanspal et al. 1992). The plot of band 3 vs α4 integrin of GPA positive cells revealed two distinct populations in normal controls: an α4 $integrin^+$ population that contained nucleated erythroid cells, and an α4 $integrin^-$ population that contained enucleated erythroid cells as previously reported (Hu et al. 2013; Chen et al. 2009). Five populations were gated on the α4 $integrin^+$ cells based on the expression levels of α4 integrin and band 3 (FIG. 1). The gated cell populations were sorted using fluorescence-activated cell sorter (FACS). Populations I, II, III, IV, and V, represented pro, EB, LB, poly and ortho respectively (Shiozawa et al. 2017). Values from the 16 normal donors were subsequently compared to the patient samples.

Genetic Profiling

Genomic DNA was extracted from BM MNCs using Qiagen's DNAeasy Blood and Tissue kit. In total, 54 genes (Table 3) that are part of the myeloid/lymphoid/acute leukemia panel at Cancer Genetics Inc. were screened for mutations. All sequencing data were analyzed using Cartagenia pipeline (Agilent Technologies). Mutations were confirmed using Sanger sequencing for a subset of genes and patients.

Statistics

All statistical tests were performed using either GraphPad Prism version 7 or MedCalc version 17.8 statistical software. For continuous variables, non-parametric two-tailed tests were used as described in the legends of corresponding figures. For categorical data, patient characteristics were compared using the Fisher's exact test where appropriate. Overall survival analysis was done using Kaplan-Meier method. OS was calculated from the date of diagnosis to date of death and censoring data at the time patients were last known to be alive. Survival curves were compared using log-rank test. Cox-proportional hazards regression analysis was used for univariate and multivariate analyses. In survival analysis, for grouping patients in TED or noTED groups, the result of TED analysis on first sample analyzed was used irrespective of TED status in subsequent samples. Where appropriate, more details on statistical tests are described in the legends of corresponding figures.

TABLE 1

Age, sex, disease subtype, IPSS-R risk category, and other clinical details of samples analyzed for TED

| Sl. No | Sample ID | Unique Patient ID - repeat order | Age [1] | Sex | WHO | Risk Cat.[2] | Myeloblast | Ring Sideroblast (%) |
|---|---|---|---|---|---|---|---|---|
| 1 | CUMC-125 | 2-1 | 75 | M | RCMD | N/A | 3 | 4 |
| 2 | CUMC-178 | 2-2 | 75 | M | RAEB-1 | Low | 7 | No record |
| 3 | CUMC-228 | 2-3 | 76 | M | RCMD | I | 3 | 6 |
| 4 | CUMC-261 | 2-4 | 76 | M | RCMD | I | 3 | Not present |
| 5 | CUMC-049 | 3-1 | 70 | M | RARS | Low | 1 | 22 |
| 6 | CUMC-312 | 4-1 | 72 | M | MDS/MPN (RARS-T) | N/A | 1 | 6/11 |
| 7 | CUMC-052 | 5-1 | 61 | F | RAEB-2 | Very high | 15 | 100 |
| 8 | CUMC-110 | 6-1 | 77 | M | RCMD | I | 3 | Not present |
| 9 | CUMC-251 | 6-2 | 78 | M | RCMD | Low | 2 | Not present |
| 10 | CUMC-175 | 7-1 | 77 | F | RA | Low | 1 | Not present |
| 11 | CUMC-292 | 7-2 | 78 | F | RARS | Low | 1 | 28 |
| 12 | CUMC-210 | 9-1 | 66 | M | RA | Very low | 2 | Not present |
| 13 | CUMC-211 | 10-1 | 82 | M | RAEB-2 | High | 15 | 3 |
| 14 | CUMC-148 | 11-1 | 60 | M | RCMD | I | 1 | 10 |
| 15 | CUMC-309 | 12-1 | 90 | M | RAEB-1 | I | 6 | No record |
| 16 | CUMC-144 | 13-1 | 55 | F | RCMD-RS | Low | 1 | 50 |
| 17 | CUMC-213 | 14-1 | 72 | M | RAEB-1 | N/A | 6 | 9 |
| 18 | CUMC-104 | 15-1 | 69 | F | RCMD-RS | Very low | 1 | 51 |
| 19 | CUMC-071 | 16-1 | 54 | M | RCMD | I | <5 | No record |
| 20 | CUMC-226 | 16-2 | 55 | M | RCMD | I | 1 | Not present |
| 21 | CUMC-078 | 17-1 | 76 | F | RAEB-1 | Low | 5 | 50 |
| 22 | CUMC-229 | 17-2 | 77 | F | RAEB-2 | High | 13 | Inadequate |
| 23 | CUMC-264 | 17-3 | 77 | F | RAEB-2 | AML | 10-25 | Not present |
| 24 | CUMC-305 | 18-1 | 85 | M | RCMD | N/A | 3 | Not present |
| 25 | CUMC-072 | 19-1 | 62 | M | RCMD | I | 1 | 10 |
| 26 | CUMC-198 | 19-2 | 63 | M | RCMD | I | 1 | Mildly above 15 |
| 27 | CUMC-075 | 20-1 | 74 | M | RAEB-1 | Low | 9 | Not present |
| 28 | CUMC-233 | 21-1 | 83 | M | RARS | Very low | 1 | 80 |
| 29 | CUMC-044 | 22-1 | 75 | F | RCMD | I | 4 | Not present |
| 30 | CUMC-139 | 22-2 | 75 | F | RCMD | I | 1 | No record |
| 31 | CUMC-086 | 24-1 | 69 | M | RCMD | Very low | 0 | 6 |
| 32 | CUMC-224 | 24-2 | 70 | M | RCMD | I | 3 | 10 |
| 33 | CUMC-094 | 25-1 | 50 | F | RAEB-1 | Very high | 9 | 12 |
| 34 | CUMC-093 | 26-1 | 79 | M | RCMD | Low | 1 | 7 |
| 35 | CUMC-040 | 27-1 | 78 | F | RAEB-1 | High | 8 | 9 |
| 36 | CUMC-064 | 27-2 | 78 | F | RAEB-2 | Very high | 12 | 15 |
| 37 | CUMC-249 | 28-1 | 79 | M | RCMD-RS | Low | 2 | 61 |
| 38 | CUMC-284 | 31-1 | 60 | F | RCMD | I | 1 | Present but unable to count |
| 39 | CUMC-174 | 32-1 | 82 | M | RAEB-2 | I | 16 | Not present |
| 40 | CUMC-202 | 32-2 | 82 | M | RAEB-2 | I | 15 | Not present |
| 41 | CUMC-230 | 32-3 | 82 | M | RAEB-2 | High | 16 | Not present |

TABLE 1-continued

Age, sex, disease subtype, IPSS-R risk category, and
other clinical details of samples analyzed for TED

| | | | | | | | | |
|---|---|---|---|---|---|---|---|---|
| 42 | CUMC-053 | 34-1 | 87 | M | RCMD | Low | 1 | Not present |
| 43 | CUMC-156 | 34-2 | 88 | M | RCMD | Low | 1 | Not present |
| 44 | CUMC-115 | 35-1 | 76 | F | RAEB-2 | Low | 10 | 20 |
| 45 | CUMC-165 | 35-2 | 77 | F | RAEB-2 | I | 10 | 25 |
| 46 | CUMC-214 | 35-3 | 77 | F | RAEB-1 | I | 9 | >15 |
| 47 | CUMC-262 | 35-4 | 78 | F | RAEB-1 | N/A | 5 | No record |
| 48 | CUMC-154 | 36-1 | 74 | M | RAEB-1 | High | 6 | 40 |
| 49 | CUMC-171 | 36-2 | 74 | M | RARS | I | 4 | 80 |
| 50 | CUMC-218 | 36-3 | 74 | M | RCMD | Low | 2 | Not present |
| 51 | CUMC-103 | 37-1 | 83 | F | RCMD-RS | Very high | 3 | 15 |
| 52 | CUMC-151 | 37-2 | 84 | F | RCMD-RS | Very high | 4 | 95 |
| 53 | CUMC-167 | 38-1 | 84 | F | MDS/MPN (RARS-T) | N/A | 1 | 85 |
| 54 | CUMC-186 | 38-2 | 85 | F | MDS/MPN (RARS-T) | Low | 1 | 68 |
| 55 | CUMC-215 | 38-3 | 85 | F | MDS/MPN (RARS-T) | Low | 2 | 96 |
| 56 | CUMC-157 | 39-1 | 95 | F | RCMD-RS | Low | 3 | 35 |
| 57 | CUMC-318 | 40-1 | 66 | F | RAEB-2 | N/A | No Info | Not present |
| 58 | CUMC-301 | 41-1 | 78 | M | RAEB-2 | High | 11 | Not present |
| 59 | CUMC-313 | 41-2 | 78 | M | RAEB-1 | High | 9 | Not present |
| 60 | CUMC-276 | 42-1 | 64 | M | RCUD-RN | N/A | 1 | Not present |
| 61 | CUMC-140 | 43-1 | 71 | M | RCMD | Low | <5 | Not present |
| 62 | CUMC-236 | 43-2 | 72 | M | RCMD-RS | I | 4 | 20 |
| 63 | CUMC-098 | 45-1 | 52 | M | RCMD | Very low | 1 | Not present |
| 64 | CUMC-290 | 45-2 | 53 | M | RCMD | Very low | 1-2 | Not present |
| 65 | CUMC-285 | 46-1 | 71 | M | RCMD | N/A | 1 | Not present |
| 66 | CUMC-162 | 47-1 | 75 | M | RCMD | I | 4 | 1 |
| 67 | CUMC-179 | 47-2 | 75 | M | RCMD | I | 3 | 5 |
| 68 | CUMC-111 | 48-1 | 76 | M | RARS | Low | 1 | 95 |
| 69 | CUMC-283 | 48-2 | 77 | M | RARS | N/A | 1 | 50 |
| 70 | CUMC-113 | 49-1 | 68 | F | RCMD | N/A | No Info | No record |
| 71 | CUMC-170 | 49-2 | 68 | F | RCMD | I | 4.5 | Not present |
| 72 | CUMC-073 | 50-1 | 78 | M | RCMD | Low | 0 | Not present |
| 73 | CUMC-149 | 51-1 | 73 | M | RAEB-1 | I | 6 | 100 |
| 74 | CUMC-188 | 51-2 | 73 | M | RAEB-2 | High | 15 | >15 |
| 75 | CUMC-240 | 51-3 | 74 | M | RCMD-RS | Low | 2 | >15 |
| 76 | CUMC-267 | 51-4 | 74 | M | RAEB-1 | N/A | 10 | 50 |
| 77 | CUMC-287 | 51-5 | 74 | M | RAEB-2 | N/A | No Info | Unable to asses |
| 78 | CUMC-081 | 52-1 | 50 | F | RCMD | Very low | 1 | 50 |
| 79 | CUMC-106 | 54-1 | 73 | M | RCMD-RS | Low | 1 | 85 |
| 80 | CUMC-243 | 54-2 | 74 | M | RCMD-RS | Low | 1 | 70 |
| 81 | CUMC-056 | 55-1 | 79 | F | RARS | Low | 0 | 80 |
| 82 | CUMC-067 | 55-2 | 80 | F | RARS | Very low | 1 | 90 |
| 83 | CUMC-147 | 55-3 | 80 | F | RARS | Low | 0 | 80 |
| 84 | CUMC-266 | 55-4 | 81 | F | RARS | Low | 1 | 80 |
| 85 | CUMC-316 | 56-1 | 71 | F | RCMD | N/A | 2 | Not present |
| 86 | CUMC-070 | 57-1 | 74 | F | RAEB-1 | I | 7 | Not present |
| 87 | CUMC-181 | 57-2 | 75 | F | RAEB-2 | High | 13 | Not present |
| 88 | CUMC-176 | 58-1 | 67 | M | RAEB-2 | I | 10 | 72 |
| 89 | CUMC-231 | 58-2 | 67 | M | RAEB-2 | High | 14 | 60 |
| 90 | CUMC-255 | 58-3 | 67 | M | RAEB-2 | I | 10 | 75 |
| 91 | CUMC-288 | 58-4 | 68 | M | RARS | Very low | 2 | 35 |

TABLE 1-continued

Age, sex, disease subtype, IPSS-R risk category, and other clinical details of samples analyzed for TED

| # | Sample | ID | Age | Sex | Subtype | IPSS-R | Score | Value |
|---|---|---|---|---|---|---|---|---|
| 92 | CUMC-046 | 59-1 | 66 | F | RCMD-RS | Very low | 1 | 85 |
| 93 | CUMC-054 | 59-2 | 66 | F | RCMD-RS | Very low | 1 | 100 |
| 94 | CUMC-069 | 59-3 | 66 | F | RCMD-RS | Low | 2 | 90 |
| 95 | CUMC-100 | 59-4 | 66 | F | RAEB-1 | I | 5 | 82 |
| 96 | CUMC-158 | 59-5 | 67 | F | RARS | I | 1 | 16 |
| 97 | CUMC-269 | 60-1 | 72 | M | RCMD-RS | I | 2 | 20 |
| 98 | CUMC-306 | 60-2 | 72 | M | RAEB-2 | Very high | 13 | Not present |
| 99 | CUMC-065 | 61-1 | 61 | M | RARS | Low | 1 | 90 |
| 100 | CUMC-307 | 61-2 | 63 | M | RA | Very low | 1 | 10 |
| 101 | CUMC-295 | 62-1 | 67 | M | RA | Low | 1 | Not present |
| 102 | CUMC-185 | 63-1 | 82 | F | RARS | Very low | 0 | 80 |
| 103 | CUMC-090 | 65-1 | 73 | M | RARS | Very low | 0 | 65 |
| 104 | CUMC-238 | 65-2 | 74 | M | RCMD-RS | Very low | 0 | 65 |
| 105 | CUMC-135 | 66-1 | 76 | M | RCMD | N/A | 1 | Not present |
| 106 | CUMC-220 | 66-2 | 77 | M | RCMD | I | 2 | Not present |
| 107 | CUMC-112 | 67-1 | 67 | M | RCMD | I | 5 | 3 |
| 108 | CUMC-195 | 67-2 | 68 | M | RAEB-2 | Very high | 11 | 3 |
| 109 | CUMC-066 | 69-1 | 73 | F | RARS | Low | 1 | 65 |
| 110 | CUMC-271 | 69-2 | 75 | F | RCMD-RS | Low | 3 | 14 |
| 111 | CUMC-085 | 70-1 | 70 | M | RCMD | High | 1 | 5 |
| 112 | CUMC-241 | 70-2 | 72 | M | RCMD | Low | 2 | Not present |
| 113 | CUMC-273 | 70-3 | 72 | M | RCMD | I | 3 | Not present |
| 114 | CUMC-095 | 71-1 | 83 | F | RA | Very low | 0 | Not present |
| 115 | CUMC-227 | 71-2 | 84 | F | RA | Low | 0 | Not present |
| 116 | CUMC-289 | 71-3 | 84 | F | RA | Very low | 0 | Not present |
| 117 | CUMC-057 | 72-1 | 80 | F | RAEB-2 | High | 14 | Not present |
| 118 | CUMC-153 | 72-3 | 80 | F | RAEB-2 | Very high | 19 | 7 |
| 119 | CUMC-275 | 72-5 | 81 | F | RAEB-2 | N/A | 19 | Inadequate |
| 120 | CUMC-092 | 73-1 | 82 | M | RCMD-RS | Very low | 1 | 40 |
| 121 | CUMC-253 | 73-2 | 84 | M | RCMD-RS | Very low | 2 | 50 |
| 122 | CUMC-108 | 74-1 | 64 | M | RA | Very low | 0 | Not present |
| 123 | CUMC-256 | 74-2 | 66 | M | RA | Very low | 1 | Not present |
| 124 | CUMC-068 | 75-1 | 74 | F | RCMD-RS | Very low | 1 | 80 |
| 125 | CUMC-234 | 75-2 | 76 | F | RCMD-RS | Low | 1 | 45 |
| 126 | CUMC-270 | 76-1 | 81 | M | RAEB-1 | N/A | 6 | 30 |
| 127 | CUMC-302 | 77-1 | 82 | M | RAEB-1 | Very high | 7 | Not present |
| 128 | CUMC-105 | 78-1 | 60 | M | RCMD | Very low | 1 | Not present |
| 129 | CUMC-159 | 79-1 | 82 | M | RCMD | Low | 4 | Not present |
| 130 | CUMC-247 | 79-2 | 83 | M | RCMD | Low | <5 | No information |
| 131 | CUMC-263 | 79-3 | 83 | M | RCMD | N/A | <5 | No information |
| 132 | CUMC-177 | 80-1 | 79 | F | MDS/MPN (RARS-T) | N/A | 1 | 90 |
| 133 | CUMC-299 | 80-2 | 80 | F | MDS/MPN (RARS-T) | I | <5 | 80 |
| 134 | CUMC-155 | 81-1 | 74 | M | RAEB-1 | Very high | 6 | 1 |
| 135 | CUMC-225 | 81-2 | 75 | M | RCMD | I | 4 | 8 |
| 136 | CUMC-130 | 82-1 | 72 | F | RCMD-RS | N/A | 4 | 54 |
| 137 | CUMC-122 | 83-1 | 79 | M | RCMD-RS | I | 1 | 15 |

TABLE 1-continued

Age, sex, disease subtype, IPSS-R risk category, and other clinical details of samples analyzed for TED

| | | | | | | | | |
|---|---|---|---|---|---|---|---|---|
| 138 | CUMC-083 | 84-1 | 74 | M | RARS | N/A | 4 | 50 |
| 139 | CUMC-216 | 84-2 | 82 | M | RCMD-RS | Low | 0 | 50 |
| 140 | CUMC-250 | 84-3 | 76 | M | RCMD-RS | Low | 3 | 30 |
| 141 | CUMC-203 | 86-1 | 72 | M | RCMD | I | 2 | 9 |
| 142 | CUMC-132 | 88-1 | 72 | F | RCMD | Very low | 1 | Not present |
| 143 | CUMC-145 | 89-1 | 65 | F | RCMD | High | 4 | Not present |
| 144 | CUMC-217 | 89-2 | 65 | F | RCMD-RS | Very high | 2 | 70 |
| 145 | CUMC-254 | 89-3 | 65 | F | RAEB-2 | Very high | 11 | 7 |
| 146 | CUMC-050 | 90-1 | 62 | M | RA | Low | 1 | Not present |
| 147 | CUMC-183 | 90-2 | 64 | M | RA | Low | 2 | No record |
| 148 | CUMC-314 | 90-3 | 65 | M | RCMD | I | 1 | Not present |
| 149 | CUMC-252 | 91-1 | 66 | F | RCMD | Low | 1 | Not present |
| 150 | CUMC-173 | 92-1 | 78 | M | RAEB-2 | Very high | 18 | Not present |
| 151 | CUMC-308 | 93-1 | 74 | M | RCMD-RS | Low | 2 | 90 |
| 152 | CUMC-055 | 95-1 | 70 | M | RCMD-RS | Low | 4 | 65 |
| 153 | CUMC-079 | 95-2 | 70 | M | RCMD-RS | Low | 4 | 95 |
| 154 | CUMC-205 | 95-3 | 71 | M | RCMD-RS | Low | 3 | 19 |
| 155 | CUMC-260 | 95-4 | 71 | M | RARS | Very low | 2 | 9 |
| 156 | CUMC-109 | 97-1 | 66 | F | MDS/MPN (RARS-T) | N/A | 3 | 50 |
| 157 | CUMC-258 | 97-2 | 68 | F | RARS | N/A | No Info | Unable to asses |
| 158 | CUMC-045 | 98-1 | 37 | F | RCMD | Low | 0 | Not present |
| 159 | CUMC-248 | 99-1 | 67 | M | RCMD | Low | 1 | Not present |
| 160 | CUMC-116 | 100-1 | 86 | M | RCMD | Low | 1 | Not present |
| 161 | CUMC-150 | 100-2 | 86 | M | RCMD | Low | 1 | Not present |
| 162 | CUMC-197 | 100-3 | 87 | M | RCMD | Low | 0 | No record |
| 163 | CUMC-223 | 100-4 | 87 | M | RCMD | I | <5 | No record |
| 164 | CUMC-237 | 100-5 | 87 | M | RCMD | I | 3 | No record |
| 165 | CUMC-296 | 100-6 | 88 | M | RCMD | Low | 2 | Not present |
| 166 | CUMC-060 | 101-1 | 59 | F | RA | Very low | 0 | Not present |
| 167 | CUMC-190 | 101-2 | 60 | F | RA | Very low | 1 | Not present |
| 168 | CUMC-051 | 102-1 | 70 | F | RAEB-1 | High | 8 | 35 |
| 169 | CUMC-123 | 103-1 | 71 | M | RCMD-RS | N/A | 1 | 82 |
| 170 | CUMC-097 | 104-1 | 81 | M | RCMD-RS | I | 1 | 83 |
| 171 | CUMC-232 | 104-2 | 82 | M | RARS | I | 0 | 60 |
| 172 | CUMC-300 | 104-3 | 83 | M | RARS | I | 1 | 80 |
| 173 | CUMC-182 | 105-1 | 83 | F | RAEB-1 | I | 7 | Present (Unable to asses) |
| 174 | CUMC-222 | 105-2 | 84 | F | RCMD-RS | Low | 4 | 50 |
| 175 | CUMC-244 | 105-3 | 84 | F | RCMD-RS | I | 4 | 60 |
| 176 | CUMC-196 | 106-1 | 69 | M | RCMD-RS | Low | 2 | 93 |
| 177 | CUMC-212 | 106-2 | 69 | M | RCMD-RS | Low | 2 | 93 |
| 178 | CUMC-206 | 107-1 | 66 | M | RAEB-2 | I | 12 | Not present |
| 179 | CUMC-048 | 108-1 | 74 | M | RCMD | I | 5 | Not present |
| 180 | CUMC-126 | 110-1 | 62 | M | RAEB-1 | High | 7 | Not present |
| 181 | CUMC-194 | 111-1 | 59 | F | MDS/MPN (RARS-T) | N/A | 2 | 70 |
| 182 | CUMC-239 | 111-2 | 59 | F | MDS/MPN (RARS-T) | Very low | 1 | 50 |
| 183 | CUMC-279 | 112-1 | 83 | F | RCMD | N/A | 1 | Not present |
| 184 | CUMC-304 | 113-1 | 89 | M | RARS | Low | 1 | 45 |

TABLE 1-continued

Age, sex, disease subtype, IPSS-R risk category, and other clinical details of samples analyzed for TED

| | | | | | | | | |
|---|---|---|---|---|---|---|---|---|
| 185 | CUMC-280 | 114-1 | 79 | M | RCMD-RS | N/A | 1 | 70 |
| 186 | CUMC-114 | 115-1 | 65 | F | RCMD | N/A | No Info | Not present |
| 187 | CUMC-152 | 115-2 | 65 | F | RCMD | High | 3 | No record |
| 188 | CUMC-319 | 116-1 | 68 | M | RCMD | I | 1 | Not present |
| 189 | CUMC-191 | 117-1 | 86 | M | RCMD | Low | 1 | Not present |
| 190 | CUMC-163 | 118-1 | 68 | F | RCMD | Low | 1 | Unable to asses |
| 191 | CUMC-076 | 122-1 | 71 | F | RCMD | N/A | No Info | Not present |
| 192 | CUMC-168 | 122-2 | 72 | F | RCMD | I | 2 | Not present |
| 193 | CUMC-246 | 122-3 | 72 | F | RCMD | I | 1 | Not present |
| 194 | CUMC-259 | 122-4 | 72 | F | RCMD | I | 2 | Inadequate |
| 195 | CUMC-164 | 123-1 | 67 | F | RAEB-2 | Very high | 17 | No record |
| 196 | CUMC-200 | 123-2 | 68 | F | RAEB-2 | Very high | 15 | Not present |
| 197 | CUMC-242 | 123-3 | 68 | F | RAEB-2 | Very high | 15 | Not present |
| 198 | CUMC-131 | 124-1 | 78 | M | RAEB-2 | High | 11 | Not present |
| 199 | CUMC-062 | 125-1 | 72 | M | RA | Very low | 1 | Not present |
| 200 | CUMC-303 | 126-1 | 79 | M | RA | Low | 1 | Not present |
| 201 | CUMC-208 | 128-1 | 81 | F | RAEB-2 | Very high | 15 | Not present |
| 202 | CUMC-265 | 129-1 | 79 | F | RCMD-RS | Very low | 2 | 25 |
| 203 | CUMC-189 | 130-1 | 55 | F | RCMD | Low | 2 | Not present |
| 204 | CUMC-286 | 131-1 | 67 | F | RARS | N/A | 1 | 25 |
| 205 | CUMC-272 | 133-1 | 70 | F | RCMD | Very low | 2 | Not present |

| Sl. No | Hg (g/dL) | Platelets (10^9/L) | ANC (10^9/L) | M:E Ratio | Pro[3] | EB | LB | Poly | Ortho |
|---|---|---|---|---|---|---|---|---|---|
| 1 | No Data | No Data | No Data | 1:1 | 2.78 | 6.50 | 15.50 | 51.50 | 23.73 |
| 2 | 10.3 | 193 | 0.84 | 1:2 | No TED detected (No TED) | | | | |
| 3 | 8.5 | 98 | 0.13 | 1:1 | 1.32 | 3.19 | 10.25 | 48.26 | 36.99 |
| 4 | 9 | 188 | 0.69 | 1:1 | 0.78 | 2.01 | 11.38 | 45.68 | 40.16 |
| 5 | 7.6 | 154 | 6.73 | 1.5:1 | 2.55 | 5.06 | 10.14 | 26.83 | 55.42 |
| 6 | 9.6 | 534 | 3.55 | 4:1 | 3.60 | 5.57 | 8.25 | 27.27 | 55.30 |
| 7 | 10.4 | 78 | 0.31 | 1:2 | 0.70 | 4.21 | 12.68 | 27.71 | 54.70 |
| 8 | 8.7 | 279 | 0.54 | 4:1 | No TED detected (No TED) | | | | |
| 9 | 8.3 | 207 | 0.61 | 2:1 | No TED detected (No TED) | | | | |
| 10 | 8.1 | 391 | 3.99 | 1.5:1 | 7.44 | 17.18 | 41.00 | 19.02 | 15.35 |
| 11 | 7.7 | 331 | 3.93 | 2.5:1 | 7.97 | 12.88 | 9.83 | 38.50 | 30.83 |
| 12 | 12 | 204 | 2.91 | 1-2:1 | 2.26 | 7.39 | 13.40 | 36.49 | 40.46 |
| 13 | 10.7 | 21 | 1.61 | 1-2:1 | 0.72 | 2.02 | 9.95 | 40.03 | 47.28 |
| 14 | 6.5 | 10 | 1.47 | 2:1 | 3.32 | 5.05 | 17.03 | 44.98 | 29.22 |
| 15 | 10 | 16 | 0.71 | | 6.90 | 12.76 | 15.74 | 19.72 | 44.88 |
| 16 | 8.7 | 107 | 1.88 | 32:1 | No TED detected (No TED) | | | | |
| 17 | No Data | No Data | No Data | 3:1 | 0.19 | 1.82 | 14.48 | 37.85 | 45.66 |
| 18 | 10.6 | 71 | 1.76 | 4:1 | 4.23 | 12.38 | 20.69 | 45.35 | 17.35 |
| 19 | 8.5 | 139 | 0.31 | Not calculated | No TED detected (No TED) | | | | |
| 20 | 6.1 | 74 | 0.41 | 1:1 | No TED detected (No TED) | | | | |
| 21 | 12.2 | 243 | 5.96 | 1:1 | 1.61 | 4.12 | 13.89 | 43.38 | 36.99 |
| 22 | 7.9 | 105 | 0.66 | 1.2:1 | 0.95 | 1.33 | 4.47 | 26.61 | 66.63 |
| 23 | 11.6 | 111 | 1.88 | 2.5:1 | No TED detected (No TED) | | | | |
| 24 | 9.6 | 65 | 1.5 | 2:1 | 1.55 | 3.42 | 6.51 | 36.94 | 51.59 |
| 25 | 9.7 | 121 | 0.33 | 1:1 | 2.42 | 4.10 | 7.95 | 22.59 | 62.95 |
| 26 | 9.6 | 118 | 0.29 | 1:1.4 | 2.72 | 5.46 | 12.03 | 26.13 | 53.66 |
| 27 | 10.2 | 169 | 1.01 | 1:2 | 3.01 | 3.54 | 16.87 | 36.85 | 39.74 |
| 28 | 10.2 | 280 | 0.93 | 1.4:1 | 1.01 | 1.74 | 5.36 | 25.71 | 66.18 |
| 29 | 13 | 63 | 0.7 | 1:1 | 1.84 | 3.93 | 16.82 | 49.88 | 27.54 |
| 30 | 12.3 | 50 | 1.01 | 1:2 | No TED detected (No TED) | | | | |
| 31 | 12.5 | 88 | 3.17 | 3:1 | 1.85 | 6.54 | 20.93 | 47.50 | 23.18 |

TABLE 1-continued

Age, sex, disease subtype, IPSS-R risk category, and other clinical details of samples analyzed for TED

| | | | | | | | | | |
|---|---|---|---|---|---|---|---|---|---|
| 32 | 14.8 | 64 | 2.32 | 2:1 | 1.40 | 2.84 | 14.42 | 40.37 | 40.96 |
| 33 | 11 | 60 | 0.2 | 2:1 | 0.10 | 1.56 | 10.34 | 71.20 | 16.81 |
| 34 | 9.6 | 86 | 2.69 | 9:1 | 2.88 | 5.84 | 14.70 | 38.01 | 38.57 |
| 35 | 9 | 38 | 1.25 | 5:1 | 3.86 | 5.81 | 11.91 | 25.34 | 53.07 |
| 36 | 8.4 | 76 | 3.5 | 3:1 | 0.72 | 2.92 | 13.62 | 32.15 | 50.60 |
| 37 | 9.7 | 207 | 1.19 | 1:2 | 1.85 | 2.03 | 6.35 | 30.36 | 59.40 |
| 38 | 10.7 | 167 | 1.27 | 2:1 | No TED detected (No TED) | | | | |
| 39 | 13.1 | 117 | 0.67 | 3.5:1 | 1.78 | 2.72 | 17.26 | 52.04 | 26.20 |
| 40 | 12.3 | 106 | 0.91 | 1.5:1 | 1.80 | 3.52 | 9.64 | 33.10 | 51.95 |
| 41 | 11.9 | 93 | 0.49 | 1:1.2 | 1.17 | 3.24 | 4.94 | 21.53 | 69.11 |
| 42 | 10.4 | 9 | 2.14 | 2:1 | 3.65 | 8.16 | 14.86 | 25.49 | 47.84 |
| 43 | 9.9 | 12 | 3.52 | 2.75:1 | 1.78 | 4.58 | 14.07 | 31.52 | 48.05 |
| 44 | 10.4 | 137 | 1.33 | 1:2 | 0.86 | 1.59 | 8.94 | 32.42 | 56.19 |
| 45 | 8.4 | 200 | 4.79 | 4:1 | No TED detected (No TED) | | | | |
| 46 | 8.8 | 166 | 7.84 | >5:1 | 1.38 | 2.34 | 9.79 | 38.61 | 47.88 |
| 47 | 7.7 | 174 | No Data | >10:1 | 0.41 | 0.82 | 5.32 | 29.73 | 63.73 |
| 48 | 8.9 | 37 | 0.66 | 1:5 | 4.17 | 10.74 | 19.19 | 41.24 | 24.66 |
| 49 | 9.4 | 25 | 0.76 | 1:3 | 2.22 | 3.33 | 16.51 | 42.32 | 35.63 |
| 50 | 8.7 | 33 | 1.88 | 1.5:1 | 2.17 | 8.53 | 28.95 | 39.41 | 20.94 |
| 51 | 9.1 | 62 | 1.95 | 5:1 | No TED detected (No TED) | | | | |
| 52 | 7.8 | 50 | 1.45 | 2.5:1 | No TED detected (No TED) | | | | |
| 53 | 9.3 | 614 | 6.95 | 1.5:1 | 2.00 | 3.65 | 7.99 | 27.58 | 58.78 |
| 54 | 8.9 | 586 | 4.9 | 1:1 | 3.56 | 6.01 | 15.11 | 29.57 | 45.74 |
| 55 | 9.6 | 505 | 4.49 | 1:1 | 2.35 | 3.78 | 12.85 | 27.04 | 53.98 |
| 56 | 8.7 | 230 | 3.28 | 2:1 | 0.40 | 2.27 | 13.48 | 53.28 | 30.56 |
| 57 | 8.6 | 179 | 0.2 | Not calculated | No TED detected (No TED) | | | | |
| 58 | 9.6 | 38 | 5.05 | >5:1 | No TED detected (No TED) | | | | |
| 59 | 8.7 | 13 | 0.38 | 7:1 | No TED detected (No TED) | | | | |
| 60 | 14.9 | 170 | No Data | 2.8:1 | 1.85 | 4.97 | 12.17 | 48.52 | 32.50 |
| 61 | 10.7 | 11 | 2.4 | 2:1 | No TED detected (No TED) | | | | |
| 62 | 10.6 | 9 | 2.2 | 1:2 | No TED detected (No TED) | | | | |
| 63 | 15.7 | 254 | 0.85 | 1:1 | 2.68 | 5.76 | 11.70 | 26.75 | 53.11 |
| 64 | 19.4 | 291 | 1.38 | 1:1 | 5.83 | 11.13 | 19.29 | 49.56 | 14.19 |
| 65 | 10.6 | 285 | No Data | 3.5:1 | No TED detected (No TED) | | | | |
| 66 | 10.2 | 28 | 4.83 | 5:1 | 1.28 | 2.18 | 17.38 | 24.85 | 54.36 |
| 67 | 10 | 44 | 15.99 | 50:1 | 2.76 | 4.81 | 12.53 | 59.80 | 22.86 |
| 68 | 8.4 | 303 | 2.22 | 2:1 | 3.70 | 7.49 | 10.45 | 25.68 | 52.67 |
| 69 | 8.8 | 350 | No Data | 3.6:1 | 3.56 | 6.78 | 10.61 | 46.93 | 32.12 |
| 70 | 11.8 | 443 | 3.56 | Not calculated | No TED detected (No TED) | | | | |
| 71 | 7.1 | 152 | 0.72 | 5:1 | No TED detected (No TED) | | | | |
| 72 | 9.8 | 11 | 1.83 | 1:1 | 2.06 | 2.20 | 6.23 | 33.45 | 56.06 |
| 73 | 9.7 | 281 | 2.25 | 1:1 | 1.10 | 2.14 | 10.65 | 28.22 | 57.89 |
| 74 | 8.3 | 224 | 1.78 | 1-2:1 | 1.55 | 2.47 | 15.34 | 33.95 | 46.70 |
| 75 | 8.5 | 43 | 0.91 | 3.5:1 | No TED detected (No TED) | | | | |
| 76 | 9.4 | 16 | No Data | Increased | 1.22 | 2.74 | 8.04 | 28.60 | 59.41 |
| 77 | 8.6 | 30 | No Data | Not calculated | 3.47 | 4.53 | 9.26 | 30.32 | 52.42 |
| 78 | 14.2 | 61 | 3.55 | 2-3:1 | 3.37 | 6.94 | 13.39 | 50.74 | 25.55 |
| 79 | 9.1 | 189 | 1.71 | 1:1-1.5 | 3.08 | 9.36 | 12.97 | 26.71 | 47.88 |
| 80 | 8.3 | 171 | 0.86 | 1:1 | 3.27 | 5.66 | 15.02 | 29.43 | 46.61 |
| 81 | 7.9 | 237 | 5.31 | 1:1 | 2.89 | 2.81 | 12.62 | 34.18 | 53.20 |
| 82 | 11.6 | 201 | 3.6 | 2:1 | 6.18 | 6.72 | 12.74 | 38.69 | 35.67 |
| 83 | 9.8 | 164 | 2.69 | 4:1 | 0.56 | 2.24 | 9.35 | 31.97 | 55.87 |
| 84 | 9.2 | 191 | 2.26 | 1.5:1 | 2.59 | 2.63 | 10.75 | 32.66 | 51.37 |
| 85 | No Data | No Data | No Data | 2:1 | 3.53 | 5.44 | 6.36 | 47.53 | 37.14 |
| 86 | 9.5 | 180 | 0.31 | 3:1 | No TED detected (No TED) | | | | |
| 87 | 11.2 | 14 | 0.07 | 59:1 | No TED detected (No TED) | | | | |
| 88 | 9.3 | 145 | 4.56 | 2:1 | 1.17 | 2.88 | 15.23 | 36.89 | 43.82 |
| 89 | 7.2 | 94 | 1.81 | 1.8:1 | 0.85 | 1.88 | 7.25 | 26.97 | 63.06 |
| 90 | 9.8 | 217 | 1.77 | 1:1 | 0.46 | 0.92 | 3.41 | 31.47 | 63.74 |
| 91 | 12.7 | 281 | 4.17 | 1:1 | 2.11 | 4.49 | 10.82 | 37.47 | 45.12 |
| 92 | 10.1 | 280 | 4.88 | 1:1 | 2.52 | 3.65 | 21.75 | 27.49 | 44.59 |
| 93 | 10.2 | 368 | 6.09 | 2:1 | No TED detected (No TED) | | | | |
| 94 | 8.4 | 222 | 3.36 | 1:2 | 2.30 | 3.59 | 11.11 | 26.88 | 56.12 |
| 95 | 8 | 183 | 3.66 | 2:1 | 2.50 | 5.57 | 12.25 | 24.17 | 55.51 |
| 96 | 8.7 | 69 | 2.83 | 11:1 | 1.80 | 1.55 | 12.07 | 34.22 | 50.36 |
| 97 | 8.5 | 95 | 1.29 | 1.3:1 | No TED detected (No TED) | | | | |
| 98 | 8.1 | 23 | 0.33 | Markedly increased | No TED detected (No TED) | | | | |

TABLE 1-continued

Age, sex, disease subtype, IPSS-R risk category, and
other clinical details of samples analyzed for TED

| | | | | | | | | | |
|---|---|---|---|---|---|---|---|---|---|
| 99 | 9.6 | 422 | 4.33 | 1:1 | 2.43 | 5.98 | 16.70 | 37.44 | 37.44 |
| 100 | 12.1 | 249 | 2.14 | 1:1 | 4.21 | 5.71 | 9.08 | 50.94 | 30.06 |
| 101 | 8.8 | 406 | 3.45 | | No TED detected (No TED) | | | | |
| 102 | 8 | 301 | 3.73 | 1:2 | 1.80 | 4.10 | 20.44 | 31.85 | 41.82 |
| 103 | 11.7 | 176 | 2.39 | 1.5:1 | 3.21 | 5.63 | 11.66 | 25.67 | 53.83 |
| 104 | 10.4 | 190 | 1.82 | 1:1 | 1.11 | 2.16 | 4.87 | 25.00 | 66.85 |
| 105 | No Data | No Data | No Data | 1.1:1 | No TED detected (No TED) | | | | |
| 106 | 9.2 | 171 | 0.66 | 1:1.5 | No TED detected (No TED) | | | | |
| 107 | 6.4 | 123 | 0.84 | 5:1 | 0.62 | 2.33 | 13.00 | 39.83 | 44.23 |
| 108 | 7.8 | 123 | 1.14 | 3.2:1 | No TED detected (No TED) | | | | |
| 109 | 9.7 | 255 | 4.2 | 3:1 | 12.88 | 12.93 | 14.58 | 31.01 | 28.61 |
| 110 | 9.6 | 125 | 1.85 | 3.5:1 | 0.98 | 3.15 | 6.34 | 40.61 | 48.92 |
| 111 | 11.9 | 98 | 0.68 | 1.5:1 | 1.45 | 2.19 | 6.73 | 60.97 | 28.66 |
| 112 | 12.3 | 60 | 0.56 | 1.4:1 | 0.92 | 1.33 | 4.20 | 29.05 | 64.50 |
| 113 | 12.3 | 54 | 5.46 | 2:1 | No TED detected (No TED) | | | | |
| 114 | 10.6 | 184 | 4.84 | 2.5:1 | 3.87 | 6.83 | 12.36 | 24.92 | 52.03 |
| 115 | 9.5 | 243 | 4.74 | 3:2 | No TED detected (No TED) | | | | |
| 116 | 11.5 | 236 | 3.49 | 2:1 | No TED detected (No TED) | | | | |
| 117 | 9.9 | 122 | 0.68 | 1.5:1 | 2.83 | 4.93 | 19.71 | 42.22 | 30.31 |
| 118 | 8.4 | 132 | 0.17 | 1.3:1 | 0.40 | 2.41 | 18.24 | 41.52 | 37.43 |
| 119 | 7.7 | 90 | No Data | 1:1 | No TED detected (No TED) | | | | |
| 120 | 9 | 167 | 0.81 | 1:1-2 | 2.35 | 4.59 | 10.51 | 29.81 | 52.74 |
| 121 | 11.3 | 170 | 1.62 | 1:1 | 1.27 | 1.73 | 9.67 | 26.49 | 60.84 |
| 122 | 13.9 | 178 | 2.55 | 2:1 | 1.67 | 4.77 | 9.16 | 26.51 | 57.89 |
| 123 | 13.2 | 177 | 2.45 | 2:1 | 2.19 | 3.36 | 13.23 | 38.27 | 42.94 |
| 124 | 11.8 | 289 | 3.33 | 2-1:1 | 7.40 | 17.05 | 28.08 | 22.90 | 24.57 |
| 125 | 9.2 | 239 | 1.92 | 2.3:1 | 2.13 | 3.85 | 8.14 | 25.15 | 60.73 |
| 126 | 8.6 | 208 | No Data | 1:2 | No TED detected (No TED) | | | | |
| 127 | 8.7 | 73 | 0.39 | 2:1 | 1.45 | 4.70 | 6.91 | 38.62 | 48.33 |
| 128 | 15.2 | 81 | 1.32 | 1.5:1 | 2.65 | 7.75 | 15.98 | 51.22 | 22.40 |
| 129 | 11.1 | 232 | 3.58 | 2:1 | 1.79 | 5.92 | 23.57 | 40.96 | 27.75 |
| 130 | 9.4 | 162 | 2.98 | | No TED detected (No TED) | | | | |
| 131 | 8.8 | 69 | No Data | | No TED detected (No TED) | | | | |
| 132 | 6.9 | 494 | 2 | 1:2.9 | No TED detected (No TED) | | | | |
| 133 | 7.2 | 452 | 2.66 | | No TED detected (No TED) | | | | |
| 134 | 8.1 | 31 | 0.58 | 2:1 | 0.36 | 4.91 | 22.72 | 37.16 | 34.85 |
| 135 | 8.7 | 58 | 1.89 | 1:3-4 | 1.84 | 3.39 | 9.26 | 43.91 | 41.61 |
| 136 | 7.7 | 46 | No Data | 1-2:1 | 3.92 | 3.76 | 10.31 | 26.97 | 55.04 |
| 137 | 9.7 | 40 | 2.6 | 1.5:1 | 2.95 | 4.89 | 20.10 | 45.08 | 26.98 |
| 138 | 8 | 451 | No Data | Not calculated | 3.05 | 7.20 | 19.67 | 29.89 | 40.18 |
| 139 | 12.3 | 79 | 0.78 | 1.5:1 | 3.44 | 8.13 | 16.42 | 39.31 | 32.69 |
| 140 | 12.2 | 145 | 1 | 1:1 | 1.83 | 2.94 | 9.75 | 32.55 | 52.94 |
| 141 | 12.8 | 70 | 5.03 | 1:1.3 | 5.05 | 14.75 | 24.56 | 31.85 | 23.79 |
| 142 | 13 | 86 | 1.43 | 1-2:1 | 0.99 | 2.34 | 14.35 | 41.56 | 40.76 |
| 143 | 10.4 | 126 | 1.96 | 1:3 | 1.09 | 2.70 | 9.38 | 27.18 | 59.66 |
| 144 | 7.8 | 94 | 0.36 | <1:10 | 0.34 | 1.03 | 12.84 | 41.84 | 43.94 |
| 145 | 8.8 | 26 | 0.03 | 1:5 | 0.19 | 0.47 | 4.25 | 28.69 | 66.40 |
| 146 | 13.1 | 47 | 1.29 | 1.5:1 | 3.58 | 7.51 | 17.75 | 54.86 | 16.30 |
| 147 | 10.2 | 70 | 0.73 | 1/1-2 | 2.85 | 6.40 | 16.78 | 45.86 | 28.11 |
| 148 | 9.4 | 30 | 0.41 | 1.5:1 | 1.41 | 3.13 | 8.17 | 38.75 | 48.54 |
| 149 | 11.8 | 36 | 1.03 | 3:1 | 0.69 | 2.69 | 5.37 | 36.13 | 55.12 |
| 150 | 7.9 | 35 | 2.85 | 7:1 | No TED detected (No TED) | | | | |
| 151 | 5.1 | 98 | 1.68 | 1.5:1 | 9.35 | 15.97 | 21.28 | 23.30 | 30.10 |
| 152 | 8.8 | 324 | 2.23 | 2-3:1 | 2.06 | 5.95 | 19.10 | 40.52 | 32.36 |
| 153 | 8.5 | 350 | 4.83 | 1.5:1 | 2.05 | 6.74 | 18.96 | 34.18 | 38.06 |
| 154 | 11.3 | 256 | 11.65 | 2.7:1 | 2.43 | 6.56 | 19.78 | 43.35 | 27.88 |
| 155 | 10.3 | 254 | 4.57 | 3:1 | 1.62 | 3.28 | 11.72 | 30.45 | 52.92 |
| 156 | 9 | 781 | 1.2 | 1:1 | 2.13 | 3.88 | 17.25 | 31.59 | 51.17 |
| 157 | 6.4 | 241 | 0.84 | Not calculated | No TED detected (No TED) | | | | |
| 158 | 10.4 | 42 | 1.83 | 1.5:1 | 0.79 | 1.95 | 9.09 | 36.42 | 51.75 |
| 159 | 14.4 | 25 | 0.54 | 2:1 | 1.88 | 5.36 | 18.66 | 44.27 | 29.84 |
| 160 | 8.4 | 137 | 1.46 | 20:1 | 0.19 | 0.47 | 6.02 | 33.17 | 60.19 |
| 161 | 6.9 | 127 | 1.48 | 105:1 | No TED detected (No TED) | | | | |
| 162 | 7.9 | 159 | 1.77 | >5:1 | 1.32 | 1.76 | 6.08 | 31.30 | 59.54 |
| 163 | 7.5 | 110 | 1.61 | >10:1 | No TED detected (No TED) | | | | |
| 164 | 6 | 188 | 2.08 | 20:1 | No TED detected (No TED) | | | | |
| 165 | 8.4 | 182 | 1.85 | >10:1 | No TED detected (No TED) | | | | |
| 166 | 10.8 | 59 | 0.8 | 1:2 | No TED detected (No TED) | | | | |
| 167 | 12.7 | 122 | 1.63 | 1:1 | 0.12 | 5.15 | 15.26 | 49.91 | 29.57 |
| 168 | 10 | 96 | 0.4 | 1.3:1 | 0.57 | 13.22 | 13.79 | 59.68 | 29.93 |

TABLE 1-continued

Age, sex, disease subtype, IPSS-R risk category, and other clinical details of samples analyzed for TED

| | | | | | | | | | |
|---|---|---|---|---|---|---|---|---|---|
| 169 | 9.6 | 307 | 2.12 | 1:2 | 0.60 | 2.27 | 20.69 | 36.07 | 40.38 |
| 170 | 7.7 | 145 | 2.75 | 1:1 | 4.36 | 7.23 | 11.18 | 25.81 | 51.42 |
| 171 | 7.5 | 243 | 3.01 | 1:1 | 1.57 | 3.40 | 10.28 | 35.89 | 48.85 |
| 172 | 7.9 | 314 | 4.38 | 1:1 | 2.69 | 4.26 | 8.11 | 48.17 | 36.76 |
| 173 | 7.3 | 131 | 0.99 | 3:1 | No TED detected (No TED) | | | | |
| 174 | 10.55 | 88 | 0.92 | 1:2 | 1.51 | 4.31 | 10.17 | 35.07 | 48.93 |
| 175 | 7 | 75 | 0.85 | 1.3:1 | 3.29 | 4.68 | 15.08 | 34.49 | 42.46 |
| 176 | 6.3 | 222 | 2.53 | 1:1.9 | 3.87 | 6.58 | 19.12 | 28.61 | 41.82 |
| 177 | 7.9 | 227 | 1.8 | | No TED detected (No TED) | | | | |
| 178 | 13.7 | 132 | 1.15 | 1:1 | 2.74 | 5.98 | 9.84 | 48.65 | 32.78 |
| 179 | 10.7 | 88 | 4.74 | 9:1 | No TED detected (No TED) | | | | |
| 180 | 9 | 18 | 2.88 | 2:1 | 3.24 | 3.31 | 24.62 | 37.84 | 31.00 |
| 181 | 8.6 | 797 | 4.09 | 1.9:1 | 5.52 | 6.58 | 10.43 | 24.19 | 53.29 |
| 182 | 10.9 | 497 | 2.99 | 3:1 | No TED detected (No TED) | | | | |
| 183 | 7.3 | 41 | No Data | <1:1 | No TED detected (No TED) | | | | |
| 184 | 9.1 | 237 | 2 | 2:1 | 1.34 | 3.38 | 9.42 | 50.43 | 35.43 |
| 185 | 8.7 | 254 | No Data | 10:1 | 4.07 | 8.41 | 16.99 | 33.60 | 36.92 |
| 186 | 8.9 | 191 | 1.23 | Not calculated | No TED detected (No TED) | | | | |
| 187 | 6.3 | 252 | 2.51 | 15:1 | No TED detected (No TED) | | | | |
| 188 | 8.5 | 60 | 1.23 | 1.5:1 | 0.95 | 2.15 | 5.25 | 34.37 | 57.28 |
| 189 | 10.2 | 29 | 1.51 | 2.4:1 | 0.73 | 3.78 | 17.13 | 32.22 | 46.15 |
| 190 | 9.9 | 108 | 2.37 | 36:1 | No TED detected (No TED) | | | | |
| 191 | 9.7 | 52 | 2.08 | Not calculated | 1.91 | 2.61 | 11.20 | 36.98 | 47.29 |
| 192 | 9.5 | 60 | 2.13 | 7:1 | 0.46 | 1.29 | 6.22 | 41.00 | 51.03 |
| 193 | 8.8 | 27 | 2.24 | 1.5:1 | 0.63 | 0.66 | 7.73 | 26.34 | 64.64 |
| 194 | 9.3 | 28 | 1.4 | 2:1 | 1.22 | 2.87 | 12.15 | 28.95 | 54.81 |
| 195 | 11 | 82 | 0.61 | 2:1 | 2.91 | 3.33 | 10.15 | 35.94 | 47.67 |
| 196 | 9.9 | 76 | 0.69 | 2:1 | 1.58 | 3.01 | 15.78 | 41.88 | 37.75 |
| 197 | 8.2 | 95 | 1.16 | Unable to assess | No TED detected (No TED) | | | | |
| 198 | 10.8 | 42 | 1.94 | >5:1 | 0.44 | 3.83 | 14.02 | 43.04 | 38.67 |
| 199 | 12.1 | 51 | 2.94 | 1.5-2:1 | 4.92 | 5.15 | 17.30 | 42.36 | 30.28 |
| 200 | 8.8 | 254 | 3.94 | 2.5:1 | 1.50 | 4.28 | 9.95 | 40.28 | 43.98 |
| 201 | 7.8 | 484 | 1 | 4:1 | 2.79 | 6.22 | 14.11 | 37.95 | 38.93 |
| 202 | 13.9 | 163 | 0.8 | 2:1 | 0.98 | 2.27 | 13.92 | 33.23 | 50.59 |
| 203 | 8 | 430 | 0.83 | 2:1 | 3.55 | 10.88 | 32.54 | 29.79 | 23.24 |
| 204 | 11.6 | 197 | No Data | 3:1 | No TED detected (No TED) | | | | |
| 205 | 11.9 | 236 | 2.13 | 3:1 | 1.40 | 5.89 | 23.23 | 35.05 | 34.42 |

[1] Age at sample collection in years
[2] IPSS-R is calculated for each sample, N/A = not enough information to calculate IPSS-R or it was RARS-T sample, I = Intermediate
[3] Adequate cells with GPA expression present but not enough cells to accurately quantify cells in various stages of TED

TABLE 2

Percentage of cells at each distinct stage of maturation in normal individuals. Data after normalization based on total nucleated erythroid cells as 100%.

| Normal Samples | Pro | EB | LB | Poly | Ortho |
|---|---|---|---|---|---|
| 1 | 4.3 | 8.5 | 15.1 | 25.5 | 46.8 |
| 2 | 2.8 | 5.5 | 13.1 | 27.4 | 51.2 |
| 3 | 4.6 | 10.1 | 22.8 | 29.4 | 33.1 |
| 4 | 2.3 | 6.2 | 13.2 | 28.9 | 49.4 |
| 5 | 3.9 | 8 | 14.2 | 30.4 | 43.8 |
| 6 | 5 | 7.1 | 14.3 | 26.8 | 46.8 |
| 7 | 2.3 | 5.3 | 13 | 27.2 | 51.3 |
| 8 | 4.1 | 7.6 | 11.7 | 26.8 | 49.8 |
| 9 | 5.3 | 7.7 | 14 | 24.5 | 48.5 |
| 10 | 3.7 | 7 | 16.6 | 35.7 | 37 |
| 11 | 2.1 | 3.1 | 10.9 | 29 | 54.9 |
| 12 | 3.9 | 6.4 | 12.1 | 25.3 | 52.4 |
| 13 | 3.5 | 8.4 | 12.4 | 24.3 | 51.5 |
| 14 | 3 | 4.8 | 10.9 | 31 | 50.3 |
| 15 | 2.4 | 4.1 | 12 | 28.2 | 53.3 |
| 16 | 4.6 | 7.7 | 14.5 | 25.5 | 47.6 |

TABLE 3

List of genes and the exon numbers analyzed by targeted sequencing

| Sl. No. | Gene Name | Target Exons |
|---|---|---|
| 1 | ABL1 | 4 to 6 |
| 2 | ASXL1 | 12 |
| 3 | BCOR | Full |
| 4 | CALR | 9 |
| 5 | CBL | 8 to 9 |
| 6 | CEBPA | Full |
| 7 | CUX1 | Full |
| 8 | DNMT3A | Full |
| 9 | ETV6 | Full |
| 10 | EZH2 | Full |
| 11 | GATA2 | 2 to 6 |
| 12 | IDH1 | 4 |
| 13 | IDH2 | 4 |
| 14 | JAK2 | 12, 14 |
| 15 | KIT | 2, 8-11, 13, 17 |
| 16 | KMT2A | 5 to 8 |
| 17 | KRAS | 2 to 3 |
| 18 | MPL | 10 |
| 19 | NPM1 | 12 |
| 20 | NRAS | 2 to 3 |

TABLE 3-continued

List of genes and the exon numbers analyzed by targeted sequencing

| Sl. No. | Gene Name | Target Exons |
|---|---|---|
| 21 | PDGFRA | 12, 14, 18 |
| 22 | PTPN11 | 3, 13 |
| 23 | RUNX1 | Full |
| 24 | SETBP1 | 4 partial |
| 25 | SF3B1 | 13-16 |
| 26 | SMC1A | 2, 11, 16, 17 |
| 27 | SRSF2 | 1 |
| 28 | STAG2 | Full |
| 29 | TET2 | 3 to 11 |
| 30 | TP53 | 2 to 11 |
| 31 | U2AF1 | 2, 6 |
| 32 | ZRSR2 | Full |
| 33 | CSF3R | 14 to 17 |
| 34 | ATRX | 8 to 10, 17 to 31 |
| 35 | BCORL1 | Full |
| 36 | BRAF | 15 |
| 37 | CBLB | 9 to 10 |
| 38 | CBLC | 9 to 10 |
| 39 | CDKN2A | Full |
| 40 | FBXW7 | 9 to 11 |
| 41 | FLT3 | 14, 15, 20 |
| 42 | GATA1 | 2 |
| 43 | GNAS | 8 to 9 |
| 44 | HRAS | 2 to 3 |
| 45 | IKZF1 | Full |
| 46 | JAK3 | 13 |
| 47 | KDM6A | Full |
| 48 | MYD88 | 3 to 5 |
| 49 | NOTCH1 | 26-28, 34 |
| 50 | PHF6 | Full |
| 51 | PTEN | 5, 7 |
| 52 | RAD21 | Full |
| 53 | SMC3 | 10, 13, 19, 23, 25, 28 |
| 54 | WT1 | 7, 9 |

Example 2—Results of TED Analysis—TED Profiles of MDS Samples

A total of 221 samples were analyzed for TED, 16 normal controls and 205 BM samples (196 MDS including 9 MDS/myeloproliferative neoplasm [MPN] overlap) were from 113 unique patients with myeloid malignancies. A breakdown by disease type and WHO classification is provided in Table 4. Successively obtained samples during a given period were studied and do not represent patients at any particular point in their disease.

Number of samples analyzed and distribution of samples

TABLE 4 in each WHO 2008 disease subtype

| | All samples |
|---|---|
| Samples analyzed for TED | 205 |
| Control samples | 16 |
| Samples with myeloid malignancies (113 unique patients) | 221 |
| Samples with TED (TED) | 149 |
| Adequate samples but No TED detected (No TED) | 56 |

| | TED (%) | No TED (%) |
|---|---|---|
| MDS | | |
| RCUD | 1 (100%) | 0 (0%) |
| RA | 11 (73%) | 4 (27%) |
| RCMD | 73 (70%) | 32 (30%) |
| RARS | 21 (91%) | 2 (9%) |

TABLE 4-continued in each WHO 2008 disease subtype

| RAEB-1 | 16 (76%) | 5 (24%) |
|---|---|---|
| RAEB-2 | 21 (68%) | 10 (32%) |
| MDS/MPN | | |
| RARS-T | 6 (66%) | 3 (34%) |
| TOTAL | 149 | 56 |

Figure 1B:
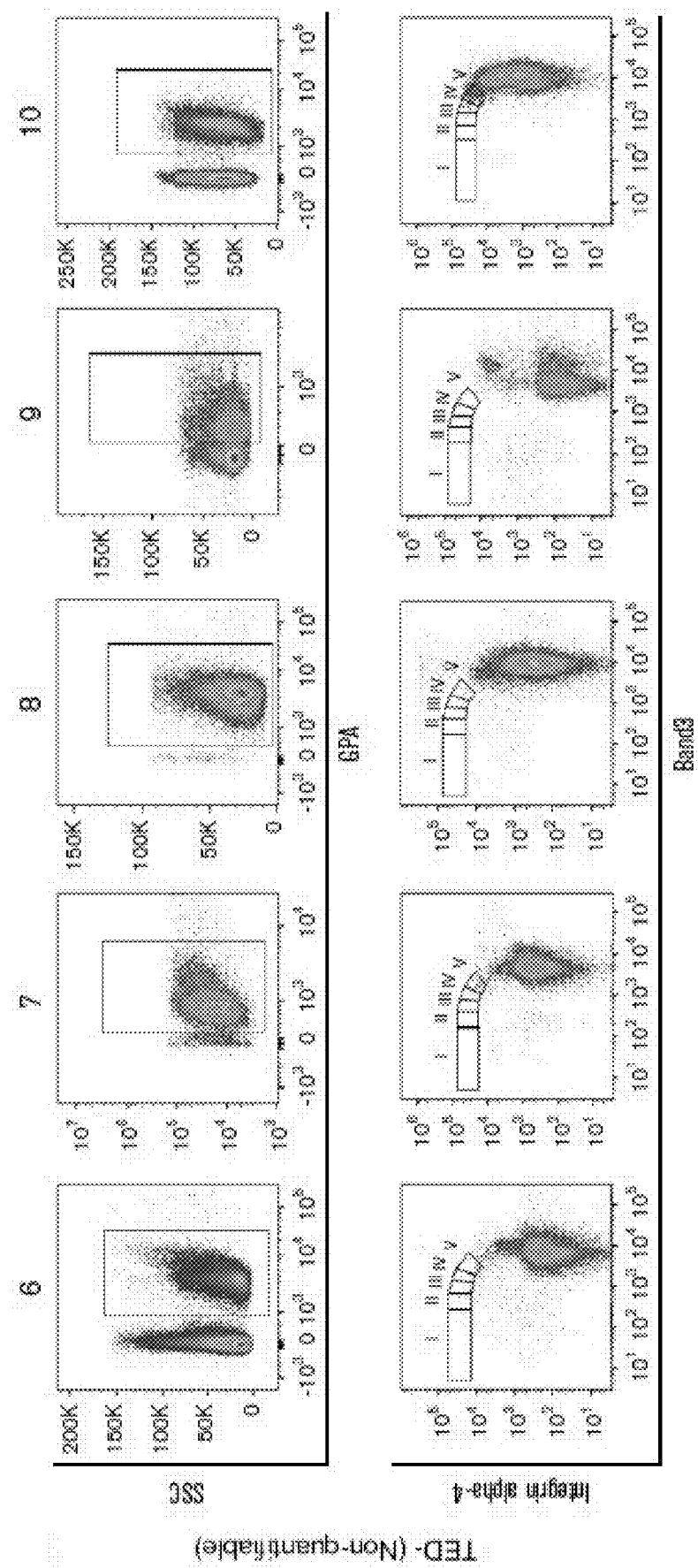
FIG. 1B are representative dot-plots of terminal erythroid differentiation profiles, as observed on flow cytometry, obtained from primary human bone marrow of MDS samples from five non-quantifiable samples. GPA positive cells (top panel in both FIGS. 1A and 1B) were found in both quantifiable and non-quantifiable samples but the non-quantifiable samples were characterized by low GPA expression (FIG. 1B, top panel) and absence of cells undergoing TED (FIG. 1B, lower panel). Gates I, II, III, IV, and V represent Pro, EB, LB, Poly and Ortho stages of TED.

RAEB, refractory anemia with excess blasts;
RCMD, refractory cytopenia with multilineage dysplasia As proerythroblasts (GPA+ cells) undergo TED through four successive mitoses, surface expression of band 3 increases and integrin α-4 decreases. Using flow cytometry, cells in pro, EB, LB, poly and ortho stages of TED were measured. Of 205 BM samples, 149 exhibited quantifiable TED profile (referred to as TED-positive or simply TED). FIG. 1 shows 5 representative MDS patients in whom TED was quantifiable (FIG. 1A) or not (FIG. 1B). The top panels in both 1A and 1B show that a sufficient number of cells were marked by expression of GPA, integrin alpha-4 and band 3. The bottom panel in FIG. 1A shows the number of cells increasing from pro to ortho stage in all 5 cases. On the other hand, 56/205 (27%) samples (FIG. 1B shows five such representative MDS patients) did not yield a reliable estimation of TED because too few cells were positive for both integrin alpha-4 and band 3.

FIG. 2 and Table 2 shows the percentage of cells in various TED stages in normal as well as MDS samples. TED followed an expected doubling pattern with little variation between samples from normal individuals (Table 2). When all MDS samples were grouped together, it was clear that TED did not follow the expected doubling pattern from the start showing significantly fewer cells in pro ($P \leq 0.01$) and EB ($P \leq 0.05$). At LB stage, an equal number of cells appeared in normal and MDS samples, but in the poly stage, a significantly higher percentage of cells were detected ($P < 0.001$), with a sudden drop-off in ortho (FIG. 2A, Table 5).

Figure 2A:
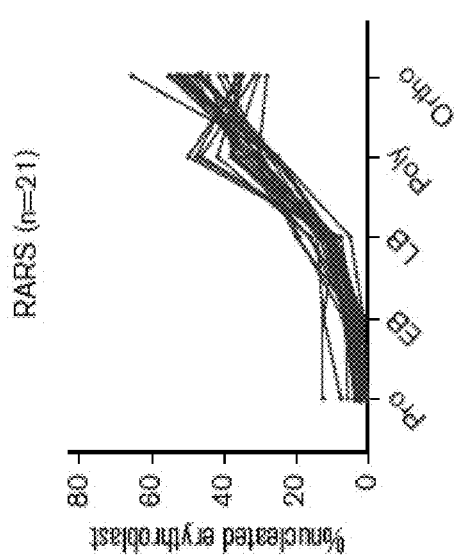
FIG. 2A is a bar diagram showing percentage of nucleated erythroid cells in each stage of TED. When compared to normal (n=16), MDS samples (n=95) were characterized by a significant decrease in percentage of cells in Pro and EB stages and a significantly abnormal increase of cells in poly stage, and a decrease in ortho stage. Data in bar diagram is presented as mean+S.E.M. Each TED stage was compared between normal and MDS samples using unpaired, two-tailed, non-parametric t-test (Mann Whitney).
Figure 2B:
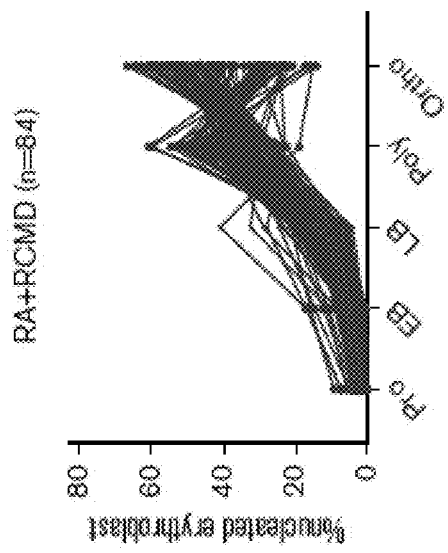
FIG. 2B is a line plot showing percentage of cells quantified in each TED stage in individual samples in the RA and RCMD WHO subgroup.
Figure 2C:
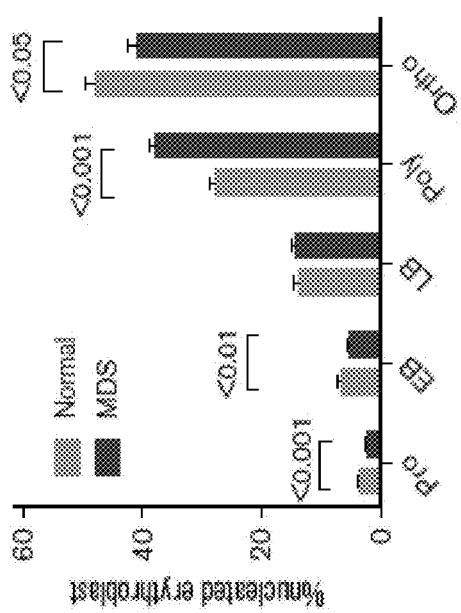
FIG. 2C is a line plot showing percentage of cells quantified in each TED stage in individual samples in the RARS WHO subgroup.
Figure 2D:
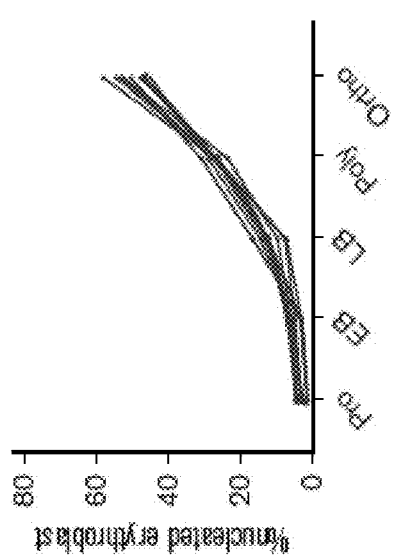
FIG. 2D is a line plot showing percentage of cells quantified in each TED stage in individual samples in the RAEB-1 WHO subgroup.
Figure 2E:
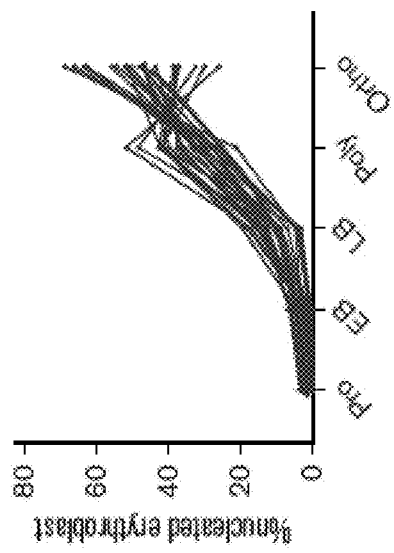
FIG. 2E is a line plot showing percentage of cells quantified in each TED stage in individual samples in the RAEB-2 WHO subgroup.
Figure 2F:
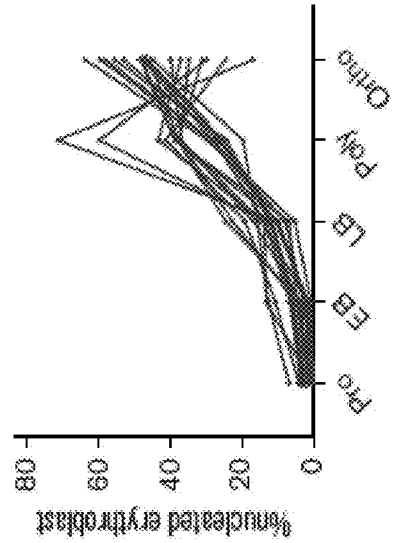
FIG. 2F is a line plot showing percentage of cells quantified in each TED stage in individual samples in the RARS-T WHO subgroups. The red line in FIGS. 2B-2F is mean percentage of cells observed in normal individual.
Figure 2H:
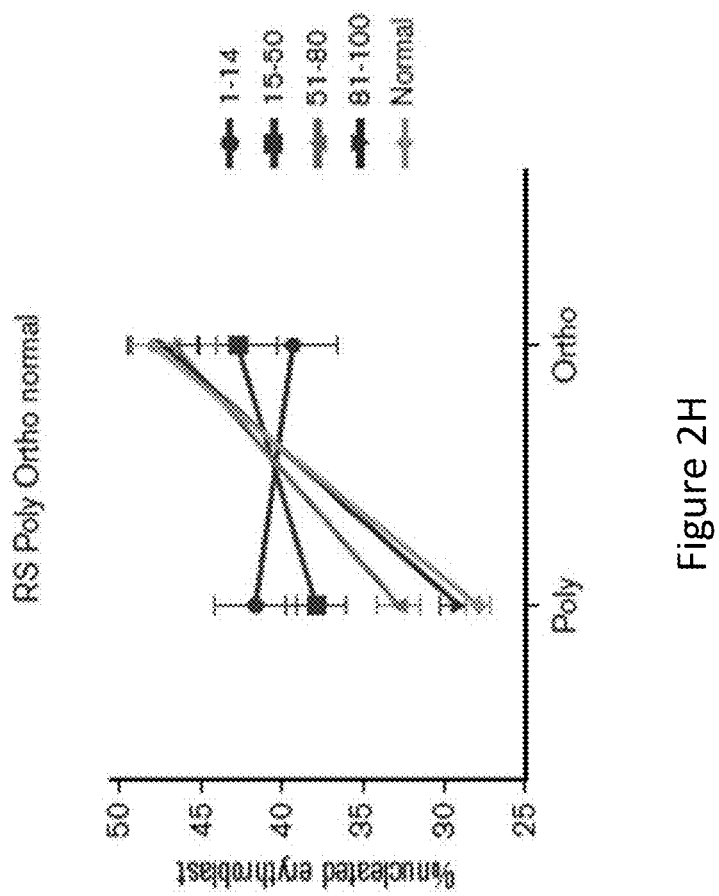
FIG. 2H is a graph showing inverse relation between poly and ortho stages within various RS groups and normal. A less arrest in poly is translated into more ortho stages.
Figure 2G:
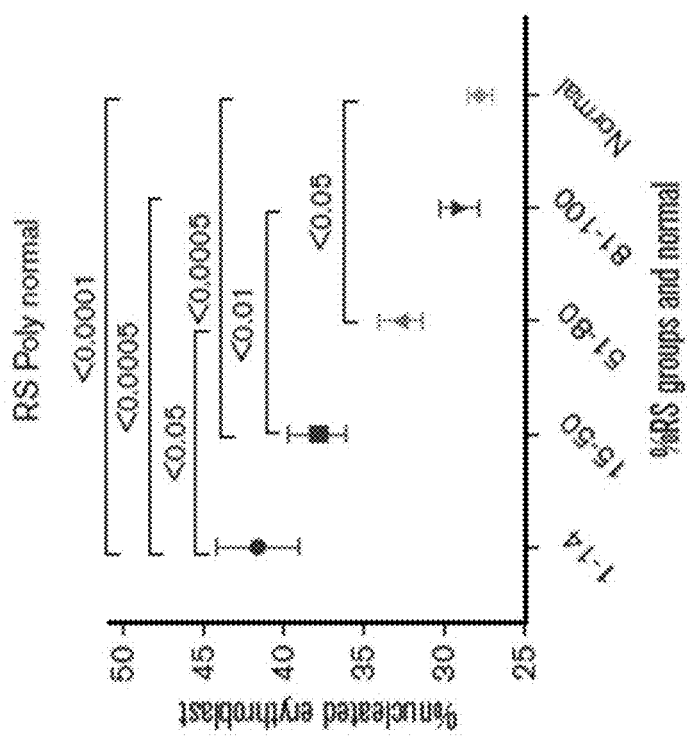
FIG. 2G is a plot showing percentage of nucleated erythroblast cells in poly stage within various RS subgroups and normal samples. There was significant difference in poly stage between different RS subgroups; less cells arrest was observed in poly stage as RS increased. All data is presented as mean+S.E.M. Samples were compared using One Way ANOVA (Kruskal-Wallis test), multiple comparison was done using Uncorrected Dunn's test.
Figure 2I:
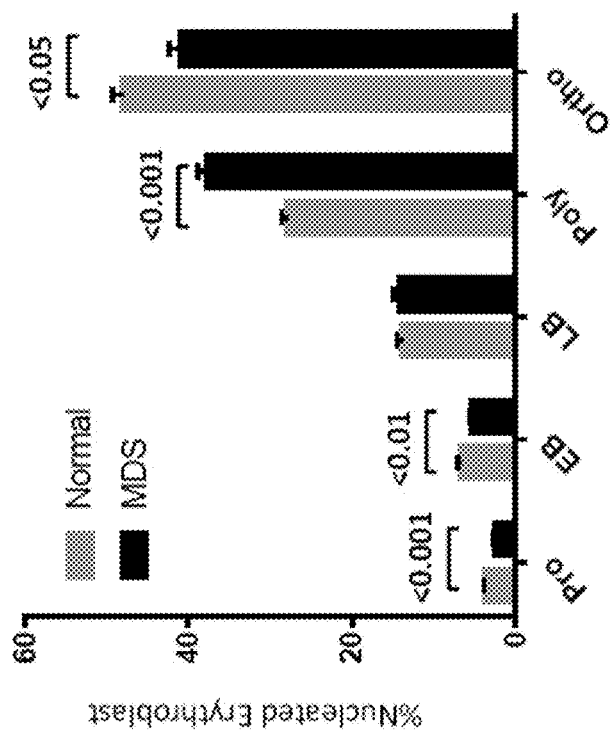
FIG. 2I is a bar diagram showing percentage of nucleated erythroid cells in each stage of TED when compared to normal (n=16). MDS samples (n=85) were characterized by a significant decrease in percentage of cells in Pro and EB stages and a significantly abnormal increase of cells in poly stage, and a decrease in ortho stage.
Figure 2J:
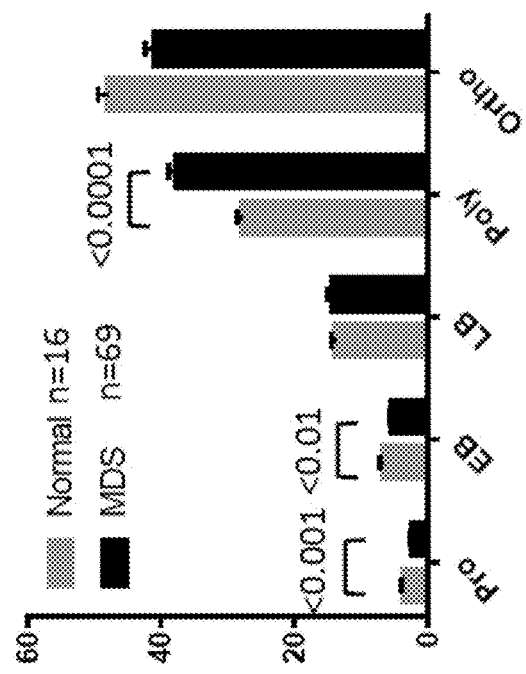
FIG. 2J is a bar diagram showing percentage of nucleated erythroid cells in each stage of TED of a subset of MDS patients (n=69), after removing inconsistent TED on repeat sampling at other times, as compared with normal. A significant decrease in percentage of cells in Pro and EB stages and a significantly abnormal increase of cells in poly stage was observed. Data in FIGS. 2I and 2J are presented as mean+S.E.M. Each TED stage was compared between normal and MDS samples using unpaired, two-tailed, non-parametric t-test (Mann Whitney).

These differences persisted when refractory anemia with ring sideroblasts associated with thrombocytosis (RARS-T) samples were excluded (FIG. 2I) or patients whose samples showed a different TED outcome on repeat sampling at later time in their disease history were excluded and only patients whose samples consistently showed TED on repeat sampling were analyzed (FIG. 2J). This increased number of cells in poly and a decrease in ortho in MDS samples suggested a loss of cells either by apoptosis somewhere between poly and ortho stages or cells normally destined for progression to ortho remained poly either because of cell-cycle and/or maturation arrest.

TABLE 5

Descriptive statistics for each TED stage in all samples from MDS and MDS-MPN (RARS-T) including sample obtained from same patients at different time-point and normal samples

| | MDS (n = 149) | | Normal (n = 16) | |
|---|---|---|---|---|
| | Mean | Median | Mean | Median |
| Pro | 2.3 | 1.9 | 3.6 | 3.8 |
| EB | 4.8 | 4.0 | 6.7 | 7.1 |
| LB | 13.2 | 12.4 | 13.8 | 13.2 |
| Poly | 36.1 | 35.1 | 27.9 | 27.3 |
| Ortho | 43.7 | 45.4 | 48.0 | 49.6 |

Example 3—Results of TED Analysis—TED Relationship with RS and WHO Subtypes

Except RARS-T, the significant differences observed in pro, EB, and poly stages in all MDS samples were retained in other MDS subtypes (FIGS. 2B to 2E). Given a near normal TED in RARS-T subgroup (n=6) (FIG. 2F), all MDS samples with any ring sideroblast were analyzed next (FIGS. 2G and 2H). There were 104 samples in the cohort with accurate quantification of RS ranging from 1-100%, irrespective of WHO classification (Table 1). These samples were divided in four groups: 1-14%, 15-50%, 51-80%, and 81-100%. No significant differences were observed between the four RS groups in pro, EB, LB, and ortho stages but a significant difference was observed in poly stage (P=0.0003) with a strong negative correlation between poly and RS (r=−0.505, P<0.0001) (FIGS. 2G and 2H). Patients with RS between 1-14% showed higher poly than patients with 51-80% and 81-100% RS (P=0.0414 and P=0.0007 respectively). Patients with 15-50% RS had higher number of polys than 81-100% RS (P=0.0096). In general, there was a striking reduction in polys as RS increased, especially remarkable in cases with >50% RS (FIGS. 2G and 2H). Interestingly while the percent of poly stage erythrobalsts was lower, the percent of ortho stage cells increased with increasing RS. This implied that RS exhibit lower cell arrest at poly stage with resulting near normal TED progression.

No significant differences were observed in all 5 TED stages when compared within the five IPSS-R categories or the four categories of blasts <5%, 5-9%, 10-19% and ≥20% blasts.

Example 4—Results of TED Analysis—MDS/sAML Samples with noTED

Despite adequate cells for flow analysis, 56 samples had too few erythroid cells undergoing TED as defined by expression patterns of integrin α-4 and band 3 to be accurately quantified (Table 4). Since all the patients assayed for TED using flow cytometry were also analyzed by pathologists at Columbia University Medical Center as part of routine care, the manual differential cell count data from bone marrow specimens was analyzed. It was reasoned that if the "too few erythroid cells" observed on flow cytometry in these 56 samples, named "noTED group" was an artifact, then the manual differential count data on erythroid cell lineage from pathology reports should not be significantly different between the TED and noTED groups. The manual differential count data on bone marrow specimen reported percentage of at least 16 different cells types, a count made from 500 cells, identifying pronormoblast, basonormoblast, polychromatic, and orthochromatic cells of erythroid lineage among others, based on their morphology. Interestingly, a significantly low number of all four cell types of erythroid lineage in noTED group was seen (FIGS. 3A-3D). Taken together, these data suggested that the flow cytometry method was accurately quantifying the various TED stages and that there was not a complete absence of TED but there are too few cells undergoing TED.

The myeloid:erythroid (M:E) ratio from the pathology reports was also analyzed and found that samples with noTED had a higher M:E ratio (mean 5.7:1) compared to samples with TED (mean 2:1, P=0.0506).

Most important, the proportion of patients with a >0.5:1 ME ratio were statistically more significant (P=0.012) in NoTED (30%) compared with TED (8%). Also, a more pronounced anemia was observed in NoTED patients, with lower hemoglobin in NoTED (median, 8.9 g/dL) compared with TED (median, 9.75 g/dL), a trend that narrowly fell short of significance (P=0.0643). No statistically significantly differences were observed in absolute neutrophil count, blast, and serum EPO levels between TED and NoTED patients (data not shown).

When separated based on their disease subtype, 84% RARS-Tshowed TED and 16% did not, whereas 70% RCMD showed TED and 30% did not. In RAEB-1/2 cases, 70% showed TED and 30% did not (Table 4). As the severity of IPSS-R risk increased, the proportion of TED-negative cases increased (Table 6).

Some patients were studied more than once. In 20 patients, repeat sampling gave different results at least at 1 time point. Appearance or disappearance of quantifiable TED in multiple studied cases was not related to any apparent clinical/pathologic change, and exclusion of these 22 cases did not change the overall statistics related to the clinical significance of TED (raw data provided in Tables 1-12).

TABLE 6

Number of samples of each IPSS-R subtype between TED-postive and TED-negative samples

|  | TED | No TED |
|---|---|---|
| Very Low | 27 (87%) | 4 (13%) |
| Low | 47 (80%) | 12 (20%) |
| Intermediate | 33 (66%) | 17 (33%) |
| High | 13 (76%) | 5 (24%) |
| Vert High | 12 (63%) | 7 (37%) |

Example 5—Results of TED Analysis—TED Versus Treatment Status

Treatments, both approved or experimental, can affect gene expression profiles of cells which in turn may alter protein expression and/or localization, presumably, including the surface markers analyzed for TED in this study. The proportions of TED and noTED patients within each treatment group was analyzed (Table 7). The majority of patients were not on any treatment at the time of sample collection (70/113) yet 23% (16/70) patients had noTED. Between TED (60%) and noTED (66%), the proportions of untreated patients were equal. Of 113 MDS patients, 27 were treated (either ongoing or in the past) with hypomethylating agents (HMA), and 21 had TED while 6 did not. Among the 7 patients who were on HMA at the time of sample collection, 5 were TED and 2 were noTED. Given that more HMA-treated patients were TED-positive, the TED-negative outcome is not related to HMA therapy, thus alleviating the concern that the treatment did not alter the markers used in the study.

For other treatments, such as an erythropoiesis-stimulating agent and rigosertib, more patients were seen in the TED group than in the NoTED group (Table 7). Although it is tempting to suggest that treatment may have a role in improving TED, the study was not sufficiently powered to analyze this effect. For example, as noted previously, there were only 7 patients on HMA treatment, but the time of sample collection from the start of treatment was different for each. Similarly, change in repeat sampling from NoTED to TED or vice versa in individual cases could be due to therapeutic interventions.

Taken together, these data suggested that the TED outcome was not related to any current or prior therapies.

TABLE 7

Number of patients in each group on different therapies.

| Drug/Therapy | TED (n = 89) | NoTED (n = 24) |
|---|---|---|
| Erythrocyte stimulating agent | 10 | 0 |
| Revlimid | 2 | 3 |
| Rigosertib | 7 | 1 |
| Hypomethylating agent | 5 | 2 |
| No therapy | 54 | 16 |
| Other/no information | 11 | 2 |

Example 6—Results of TED Analysis—TED Versus Mutational Profiles in MDS/sAML

Figure 4:
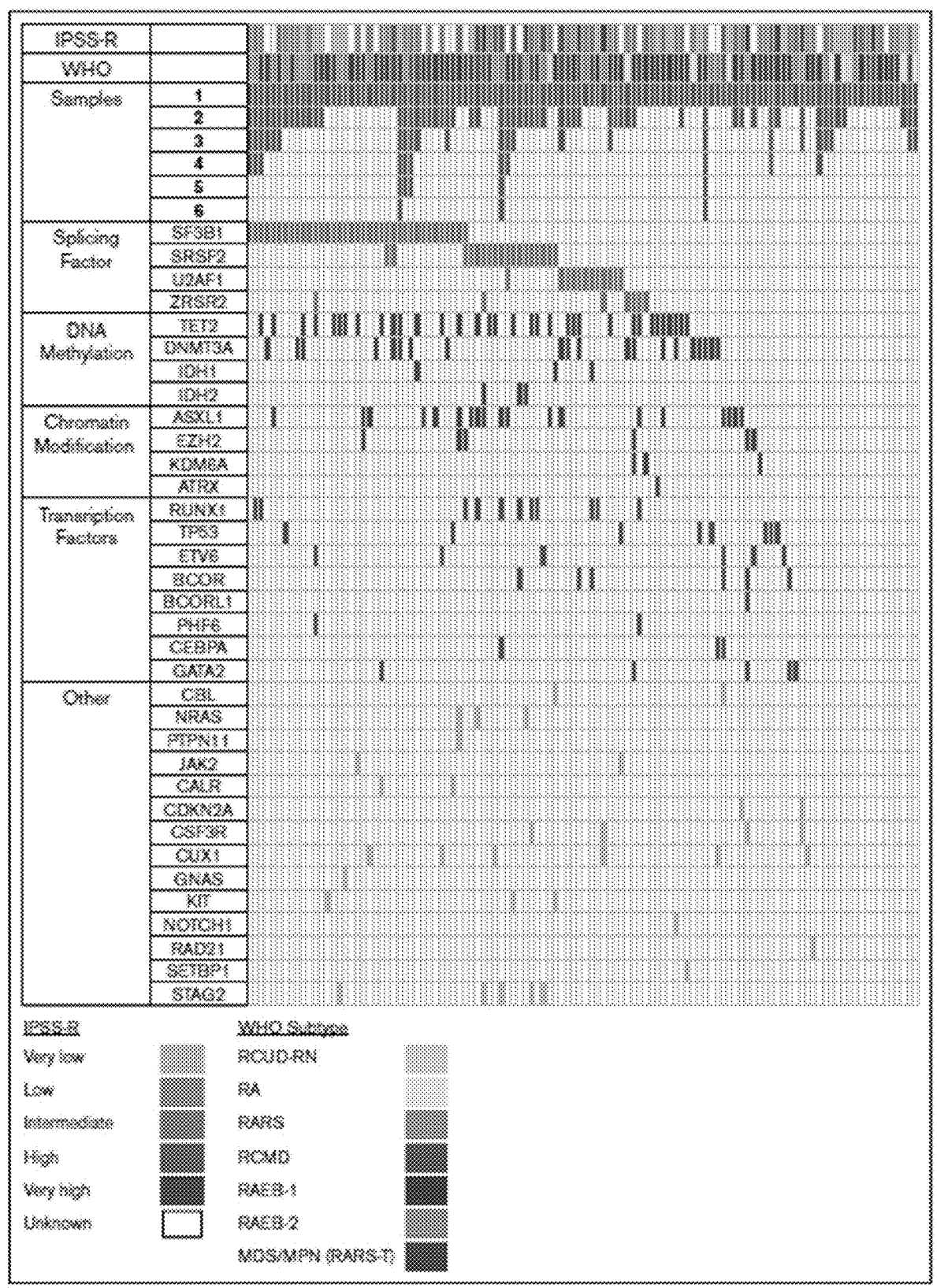
FIG. 4 is a graphic representation of number of samples analyzed for each patient (N=112) and mutations observed in the first sample analyzed. A green box represents a sample on whom TED profile was obtained and a red box indicate that the sample was adequate but no cells were found undergoing TED. Each column represents one unique patient. While on some patients every sample analyzed at different time point showed TED, whereas there were others who failed to show cells in TED at every point analyzed, and some samples who failed to show cells in TED at one or more point. A colored box, colored according to their functional group, in mutation panels show presence of mutation in that gene and patient. Splicing factor mutations were more common followed by DNA methylation. The bottom panel show color codes for the IPSSR and WHO categories.

FIG. 4 is a graphic representation of each sample examined for TED and the mutational profile (n=112). Table 8 lists all the mutations. No mutations were detected in 16% patients, and TED-negative cases had more mutations than TED-positive cases (2.3 vs 2.0). The most frequently mutated individual gene in the cohort was TET2 followed by SF3B1, DNMT3A, SRSF2 and ASXL1 (FIG. 4). The most common mutations were in splicing factor (SF) genes (61%) followed by TET2 (30%). SF mutations were present in 45/89 samples (50%) with TED and 12/24 (50%) without TED, however the distribution of specific SF genes was highly skewed. The proportion of SRFS2 mutations were significantly more in the NoTED (30%) compared with TED (12%) groups (P=0.0497). On the other hand, SF3B1 mutation was more common in the TED (35%) compared with NoTED (13%) groups, but the difference was not statistically significant (P=0.0701). SF3B1 mutation was seen in 75% samples with >15% RS and was associated with quantifiable TED.

TABLE 8

Mutation identified in 119 out 126 patients screened for mutations

| Sl. No. | Unique ID | Gene (Mutation) |
|---|---|---|
| 1 | 2 | ASXL1 (p.Y700X); SRSF2 (p.Y92N); U2AF1 (p.Q157P); |
| 2 | 3 | U2AF1 (c.C101T: p.S34F); |
| 3 | 4 | KIT (c.145C > T; p.R49C); SF3B1 (c.1986C > A; p.H662Q); |
| 4 | 5 | CSF3R (c.2326C > T; p.Q776*); CUX1 (c.2536_2537delAC; p.T846Gfs*40\|c.2542G > A; p.G848S\|c.2548_2556delAAAGAGAAG; p.K850_K852del\|c.2556G > T; p.K852N); U2AF1 (c.470A > C; p.Q157P); ZRSR2 (c.1338_1343dupGAGCCG; p.S447_R448dup); |
| 5 | 6 | TET2 (p.G1861R); |
| 6 | 7 | DNMT3A (c.547C > T; p.R183W); ZRSR2 (c.1338_1343dupGAGCCG; p.S447_R448dup); |
| 7 | 9 | None |
| 8 | 10 | None |
| 9 | 11 | None |
| 10 | 12 | BCOR (c.4618_4619insCA; p.L1540Pfs*7); BCOR (c.4618_4619insCA; p.L1540Pfs*7); IDH1 (c.257T > C; p.F86S); RUNX1 (c.317G > A; p.W106*); U2AF1 (c.101C > T; p.S34F); |
| 11 | 13 | RAD21 (c.121C > A: p.V41L); |
| 12 | 14 | BCOR (c.1005dupC; p.S336Lfs*45); BCOR (c.1005dupC; p.S336Lfs*45); IDH2 (c.419G > A; p.R140Q); RUNX1 (c.958C > T; p.R320*\|c.610C > T; p.R204*\|c.327_328dupCA; p.K110Tfs*13); SRSF2 (c.284C > A; p.P95H); |
| 13 | 15 | SF3B1 (c.1874G > T; p.R625L); TET2 (c.3646C > T; p.R1216*); |
| 14 | 16 | ASXL1 (c.3498C > G; p.S1166R); CDKN2A (c.379G > T; p.A127S); |
| 15 | 17 | IDH1 (c.395G > A; p.R132H); SF3B1 (c.2225G > A; p.G742D); TET2 (c.2599T > C; p.Y867H\|c.5167C > T; p.P1723S); |
| 16 | 18 | ASXL1 (c.3306G > T; p.E1102D); PHF6 (c.90dupG; p.L31Vfs*5); RUNX1 (c.281G > T; p.S94I); TET2 (c.651delC; p.V218Wfs*32); ZRSR2 (c.827C > A; p.S276*); |
| 17 | 19 | DNMT3A (c.939G > A; p.W313*); TET2 (c.3384T > A; p.Y1128*\|c.3823G > T; p.G1275W); U2AF1 (c.101C > T; p.S34F); |
| 18 | 20 | None |
| 19 | 21 | SF3B1 (c.2098A > G; p.K700E); STAG2 (c.1027G > A; p.V343I); TET2 (c.651delC; p.V218Wfs*32\|c.3953A > C; p.E1318A\|c.4635C > C; p.Q1545H); |
| 20 | 22 | ASXL1 (Frameshift); |
| 21 | 24 | ASXL1 (c.C1210T: p.R404X); SRSF2 (c.C284T: p.P95L); |
| 22 | 25 | None |
| 23 | 26 | None |
| 24 | 27 | ASXL1 (c.2694G > A; p.W898*); NRAS (c.179G > A; p.G60E); RUNX1 (c.958C > T; p.R320*); SRSF2 (c.284C > A; p.P95H); TET2 (p.H1792Qfs*29c.4011T > A; p.Y1337*\|c.5319delC; p.F1773Lfs*47\|c.5375_5376insAA;); |
| 25 | 28 | SF3B1 (c.1866G > C; p.E622D); SRSF2 (c.284C > G; p.P95N); |
| 26 | 31 | BCOR (c.3763G > A; p.G1255S); BCOR (c.3763G > A; p.G1255S); GATA2 (c.481C > G; p.P161A); |
| 27 | 32 | None |
| 28 | 34 | TET2 (c.845_846delCT; p.S282*\|c.5482C > T; p.Q1828*); U2AF1 (c.101C > T; p.S34F); |
| 29 | 35 | SF3B1 (p.K666T); |
| 30 | 36 | ASXL1 (c.T844I; c.2531C > Tp.L1395V; c.4183C > G); DNMT3A (c.1852-1G > A); U2AF1 (c.A470C: p.Q157P); |
| 31 | 37 | TP53 (c.T310G: p.Y104D); |
| 32 | 38 | DNMT3A (p.Y546C); SF3B1 (p.K700E); |
| 33 | 39 | TP53 (c.G422A: p.R141H; c.G347A: p.R116Q); |
| 34 | 40 | DNMT3A (c.2645G > A; p.R882H); TP53 (c.743G > A; p.R248Q); |
| 35 | 41 | ETV6 (c.602T > C; p.L201P\|c.1193T > A; p.L398Q); SRSF2 (c.284_307delCCCCGGACTCACACCACAGCCGC; p.P95_R102del); STAG2 (c.3223_3227delTCAAA; p.S1075Tfs*11); |
| 36 | 42 | Not sequenced |
| 37 | 43 | RUNX1 (c.G530A: p.R177Q); SRSF2 (c.C284G: p.P95R); TET2 (c.4045-1G > T); |
| 38 | 45 | None |
| 39 | 46 | CBL (c.1211G > A; p.C404Y); IDH1 (c.395G > A; p.R132H); KIT (c.1588G > A; p.V530I); SRSF2 (c.284C > G; p.P95R); |
| 40 | 47 | DNMT3A (c.2281A > G; p.M761V\|c.1802G > A; p.W601*); EZH2 (c.2084C > A; p.S695*); GATA2 (c.1160_1165delCCATGA; p.T387_M388del); KDM6A (c.2331T > A; p.N777K); TET2 (c.3378_3379delTC; p.Q1127Ifs*2); ZRSR2 (c.853delT; p.S285Lfs*20); |
| 41 | 48 | SF3B1 (p.D781G); TP53 (p.G266R); |

TABLE 8-continued

Mutation identified in 119 out 126 patients screened for mutations

| Sl. No. | Unique ID | Gene (Mutation) |
|---|---|---|
| 42 | 49 | JAK2 (c.G1849T: p.V617F); TP53 (c.G347A: p.R116Q); U2AF1 (c.A470G: p.Q157R); |
| 43 | 50 | TET2 (c.3637dupG; p.V1213Gfs*10\|c.4393C > T; p.R1465*); |
| 44 | 51 | DNMT3A (c.1903C > G; p.R635G); SF3B1 (c.2098A > G; p.K700E); |
| 45 | 52 | ETV6 (c.77G > C; p.S26T); |
| 46 | 54 | SF3B1 (p.H662D); |
| 47 | 55 | SF3B1 (p.H662Q); |
| 48 | 56 | None |
| 49 | 57 | CSF3R (c.2087T > C; p.M696T); RUNX1 (c.472T > C; p.F158L); SRSF2 (c.284C > A; p.P95H); STAG2 (c.1644dupT; p.T549Yfs*11); TET2 (c.3748delG; p.E1250Rfs*3); |
| 50 | 58 | RUNX1 (c.292delC; p.L98Sfs*24); SF3B1 (c.2098A > G; p.K700E); |
| 51 | 59 | DNMT3A (c.2311C > T; p.R771*); SF3B1 (c.2098A > G; p.K700E); TET2 (c.4100C > A; p.P1367Q); |
| 52 | 60 | U2AF1 (c.101C > T; p.S34F); |
| 53 | 61 | DNMT3A (c.930G > G; p.I310M); SF3B1 (c.2098A > G; p.K700E); |
| 54 | 62 | ASXL1 (c.1934delG; p.G645Vfs*58\|c.2385delC; p.W796Gfs*22\|c.4189G > A; p.G1397S); SRSF2 (c.284C > A; p.P95H); TET2 (c.1648C > T; p.R550*\|c.3268_3269delAA; p.K1090Dfs*13\|c.3409 + 1G > A\|c.3782G > A; p.R1261H\|c.5618T > C; p.I1873T); |
| 55 | 63 | GNAS (c.602G > A; p.R201H); SF3B1 (c.2098A > G; p.K700E); TET2 (c.2599T > C; p.Y867H\|c.3142delC; p.L1048Sfs*7\|c.5167C > T; p.P1723S); |
| 56 | 65 | DNMT3A (c.1712_1719delCTGCCCAG; p.A571Gfs*4); SF3B1 (c.2098A > G; p.K700E); TET2 (c.1664dupC; p.T556Nfs*11\|c.4597A > T; p.K1533*); |
| 57 | 66 | ASXL1 (c.1934_1935insG; p.G646WfsX12); ETV6 (c.1015A > G; p.R339G); EZH2 (c.1769_1772delGTCT; p.C590Lfs*84); |
| 58 | 67 | CUX1 (p.R158*); ETV6 (p.R160+); SF3B1 (p.K700E); TET2 (p.Q1191*); |
| 59 | 69 | SF3B1 (c.2347G > A; p.E783K); |
| 60 | 70 | KIT (c.200C > G; p.T67S); SRSF2 (c.284C > G; p.P95R); TET2 (c.1955dupA; p.F653Vfs*28\|c.2871dupA; p.Q958Tfs*14); |
| 61 | 71 | None |
| 62 | 72 | ASXL1 (c.1919_1929del11; p.A640fs); CEBPA (c.1021A > G; p.I341V); RUNX1 (c.484A > G; p.R162G); SRSF2 (c.284C > A; p.P95H); STAG2 (c.852dupG; p.M285Dfs*6); |
| 63 | 73 | ETV6 (c.629G > A; p.R210H); PHF6 (c.242S); SF3B1 (p.E622D); TET2 (p.Y1693*); ZRSR2 (p.Q127-); |
| 64 | 74 | None |
| 65 | 75 | SF3B1 (p.K700E); |
| 66 | 76 | EZH2 (c.392T > A; p.I131N); RUNX1 (c.601C > T; p.R201*); SF3B1 (c.2098A > G; p.K700E); SRSF2 (c.284C > A; p.P95H); |
| 67 | 77 | ASXL1 (c.2083C > T; p.Q695*); IDH2 (c.419G > A; p.R140Q); SRSF2 (c.284C > G; p.P95R); STAG2 (c.646C > T; p.R216*); ZRSR2 (c. 1338_1343dupGAGCCG; p.S447_R448dup); |
| 68 | 78 | ATRX (c.5579A > G; p.N1860S); TET2 (c.4100C > G; p.P1367R\|c.4609C > T; p.Q1537*); |
| 69 | 79 | TET2 (c.2599T > C; p.Y867H\|c.5167C > T; p.S34F); U2AF1 (c.101C > T; p.S34F); |
| 70 | 80 | CALR (c.1092_1143del52; p.L367Tfs*46; c.1137G > C; p.E379D); SF3B1 (c.2098A > G; p.K700E); TP53 (c.743G > A; p.R248Q); |
| 71 | 81 | BCOR (c.4717 + 2T > C); BCOR (c.4717 + 2T > C); DNMT3A (c.2645G > A; p.R882H\|c.185G > A; p.S62N); TET2 (c.2599T > C; p.Y867H\|c.5167C > T; p.P1723S); U2AF1 (c.101C > A; p.S34Y); |
| 72 | 82 | SF3B1 (p.K700E); |
| 73 | 83 | ASXL1 (c.4189G > A; p.G1397S); DNMT3A (c.2645G > A; p.R882H); TET2 (c.1894C > T; p.Q632*\|c.3322_3323delCC; p.P1108Ffs*21); |
| 74 | 84 | ASXL1 (p.G646WfsX12; c.1934_1935insG); SF3B1 (p.K700E); TET2 (p.K201-); |
| 75 | 86 | KDM6A (c.2331T > A; p.N777K); ZRSR2 (c.541T > A; p.C181S); |
| 76 | 88 | TET2 (c.1176_1177delTT; p.S393Cfs*49\|c.5100delT; p.N1700Kfs*19); |
| 77 | 89 | TP53 (p.V157F); |
| 78 | 90 | None |
| 79 | 91 | |
| 80 | 92 | IDH2 (c.419G > A; p.R140Q); NRAS (c.190T > G; p.Y64D); SRSF2 (c.284C > A; p.P95H); |
| 81 | 93 | JAK2 (c.1849G > T; p.V617F); SF3B1 (c.1986C > G; p.H662Q); TET2 (c.4282delG; p.E1428Sfs*20\|c.5618T > C; p.I1873T); |
| 82 | 95 | RUNX1 (p.Q247-); SF3B1 (p.K700E); TET2 (p.R1455-; ML (1456-1457); -); |
| 83 | 97 | ASXL1 (c.2060_2061delGT; Frameshiftc.2957A > G; p.N986S); SF3B1 (p.E622D); |
| 84 | 98 | KDM6A (c.1960C > A; p.P654T); |
| 85 | 99 | SRSF2 (c.284C > A; p.P95H); TET2 (c.5473C > T; p.Q1825*); |
| 86 | 100 | DNMT3A (p.F1259L); |
| 87 | 101 | None |
| 88 | 102 | DNMT3A (c.2339T > C; p.I780T\|c.1474 + 1G > C); SF3B1 (c.2098A > G; p.K700E); SRSF2 (c.284C > T; p.P95L); TET2 (c.3986T > A; p.L1329Q\|c.4011T > A; p.Y1337*); |
| 89 | 103 | ASXL1 (c.1900_1922delAGAGAGGCGGCCACCACTGCCAT; p.E635Rfs*15); EZH2 (c.786dupC; p.N263Qfs*8); SF3B1 (c.2098A > G; p.K700E); |
| 90 | 104 | SF3B1 (p.R625C); |
| 91 | 105 | None |
| 92 | 106 | SF3B1 (c.2098T > C p.K700E); |
| 93 | 107 | GATA2 (c.481C > G; p.P161A); |
| 94 | 108 | ASXL1 (c.2077C > T; p.R693*); EZH2 (c.2061G > A; p.N687K); NRAS (c.182A > C; p.Q61P\|c.35G > A; p.G12D); PTPN11 (c.1472C > T; p.P491L); SF3B1 (c.1997A > C; p.K666T); TET2 (c.1337delT; p.L446*); |
| 95 | 110 | ASXL1 (c.2131dupA; p.T711Nfs*7\|c.2133dupT; p.A712Cfs*6); BCOR (c.4021C > T; p.R1341W\|c.3987C > A; p.C1329*); BCOR (c.4021C > T; p.R1341W\|c.3987C > A; p.C1329*); CBL (c.1259G > A; p.R420G); CEBPA (c.878_880delACA; p.N293del); ETV6 (c.1138T > G; p.W380G); |
| 96 | 111 | ASXL1 (c.3426G > C; p.Q1142H); SF3B1 (p.K700E); |
| 97 | 112 | SETBP1 (c.2612T > C; p.I871T); TET2 (c.2599T > C; p.Y867H\|c.5167C > T; p.P1723S); |
| 98 | 113 | ASXL1 (c.3745A > G; p.M1249V); CUX1 (c.124A > T; p.K42*); SF3B1 (c.2098A > G; p.K700E); |
| 99 | 114 | DNMT3A (c.1126G > A; p.A376T\|c.918G > A; p.W306*); SF3B1 (c.1873C > T; p.R625C); |
| 100 | 115 | DNMT3A (c.1969G > A; p.V657M); SF3B1 (c.2098A > G; p.K700E); |

TABLE 8-continued

Mutation identified in 119 out 126 patients screened for mutations

| Sl. No. | Unique ID | Gene (Mutation) |
|---|---|---|
| 101 | 116 | DNMT3A (c.746dupA; p.P250Afs*3\|c.723_745delGGCCAGCCCTCCTGCTGTGCAGC; p.S243Hfs*2\|c.745C > G; p.Q249E\|c.742C > G; p.Q248E); NOTCH1 (c.7648A > G; p.I2550V); TET2 (c.22C > G; p.H8D); |
| 102 | 117 | None |
| 103 | 118 | CUX1 (c.1573C > G; p.L525V); |
| 104 | 122 | None |
| 105 | 123 | CDKN2A (c.430C > T; p.R144C); CSF3R (c.2488C > T; p.P830S); |
| 106 | 124 | CUX1 (c.4123C > T; p.P1375S); SRSF2 (c.284C > T; p.P95L); TET2 (c.3380A > C; p.Q1127P\|c.3383delA; p.Y1128Lfs*9\|c.3385delG; p.D1129Ifs*8\|c.3635T > A; p.L1212*); |
| 107 | 125 | ASXL1 (c.3910C > G; p.L1304V); |
| 108 | 126 | DNMT3A (c.1429 + 1G > A); |
| 109 | 128 | BCOR (c.1005dupC; p.S336Lfs*45); BCOR (c.1005dupC; p.S336Lfs*45); BCORL1 (c.3158A > G; p.K1053R); CSF3R (c.2326C > T; p.Q776*); EZH2 (c.2228G > A; p.G743D); GATA2 (c.383_384dupCC; p.S129Pfs*90); |
| 110 | 129 | RUNX1 (c.939_950del12; p.L313fs); U2AF1 (c.470A > C; Q157P); |
| 111 | 130 | CALR (c.1132G > C; p.E378Q\|c.1137G > C; p.E379D\|c.1144delG; p.A382Qfs*48); GATA2 (c.669G > A; p.M223I); SF3B1 (c.1873C > T; p.R625C); TET2 (c.419A > G; p.N140S); |
| 112 | 131 | CEBPA (c.584_589dupACCCGC; p.H195_P196dup); CUX1 (c.1538G > A; p.R513H); DNMT3A (c.1740delC; p.W581Gfs*70); |
| 113 | 133 | DNMT3A (c.2206C > T; p.R736C); TP53 (c.746G > C; p.R249T); |

Example 7—Results of TED Analysis—TED Versus Overall Survival

Figure 5C:
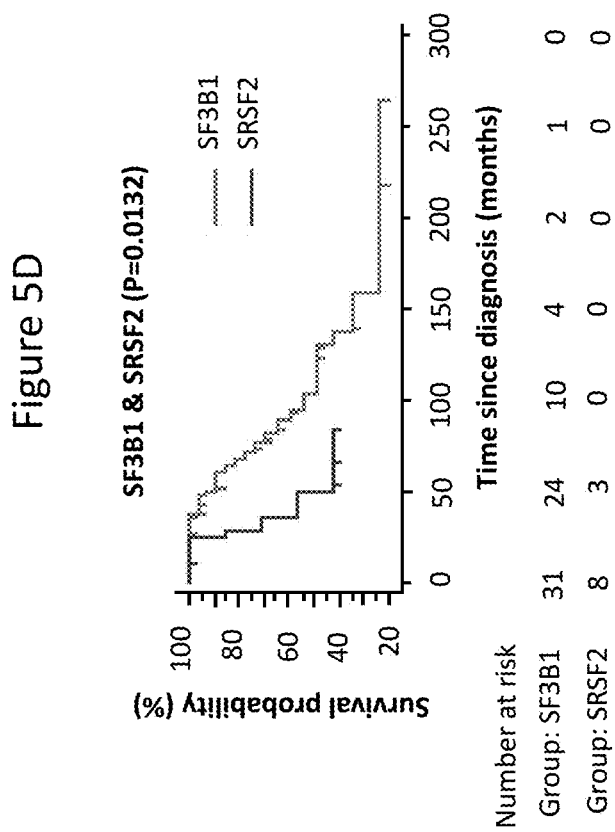
FIG. 5C is a survival curve for RAEB (RAEB-1 and RAEB-2) group of patients (P=0.029).
Figure 6A:
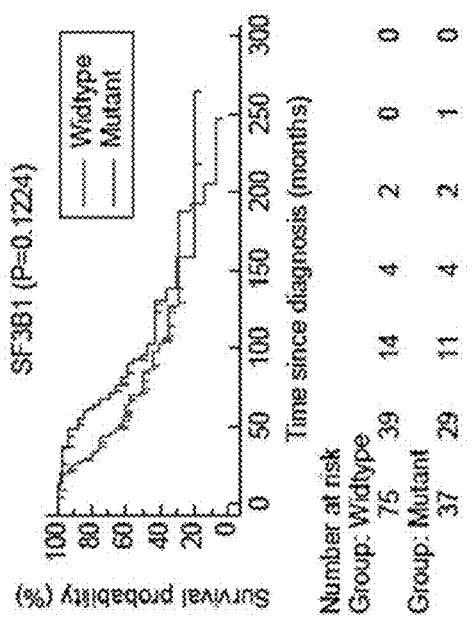
FIG. 6A is a survival curve of TED and NoTED MDS patients excluding RARS-T (P<0.0001).A). There was a significant difference in OS between TED and NoTED MDS patients excluding RARS-T.

Table 9 shows data used for survival analysis and Table 10 shows patient characteristics and their association with median survival. For all survival analyses, only the results of the first sample on each patient were used. There was a highly significant difference in OS between TED-positive (median 103 months) versus TED-negative (median 60 months) patients (P=0.0001, FIG. 5A). The difference in median survival remained unchanged when 6 RARS-T patients were excluded (FIG. 6A).

Figure 5D:
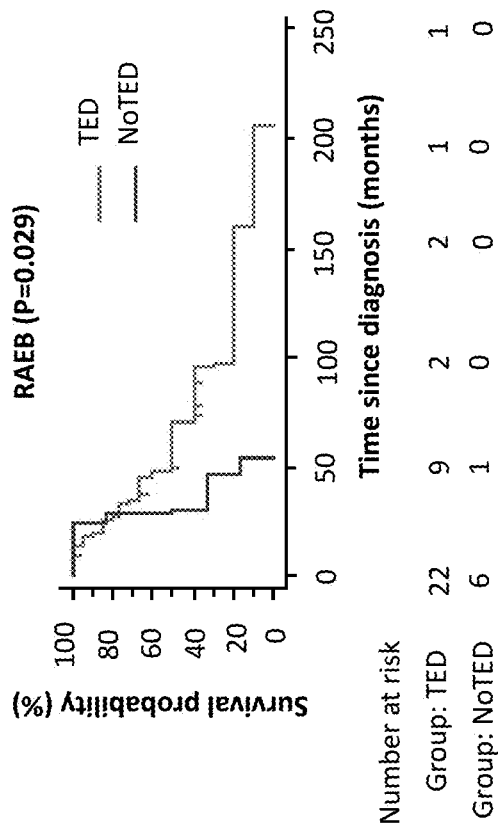
FIG. 5D is a survival curve for patients with TED and with SF3B1 or SRSF2 mutations (P=0.0132).
Figure 5H:
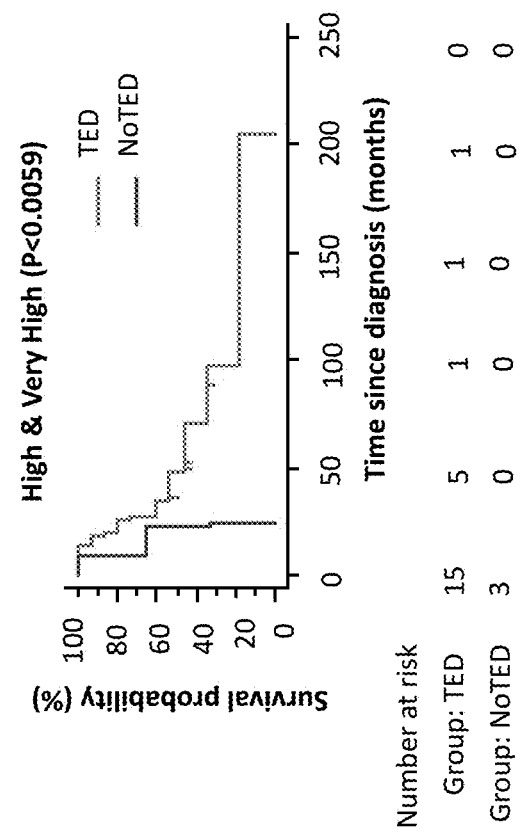
FIG. 5H is a survival curve for patients classified as IPSSR high and very high categories (P=0.0059). There was a significant difference in overall survival between TED and NoTED among all groups. Log-rank test was used to compare the curves. The tables below the curves indicate the number of patients at risk in each group.
Figure 5G:
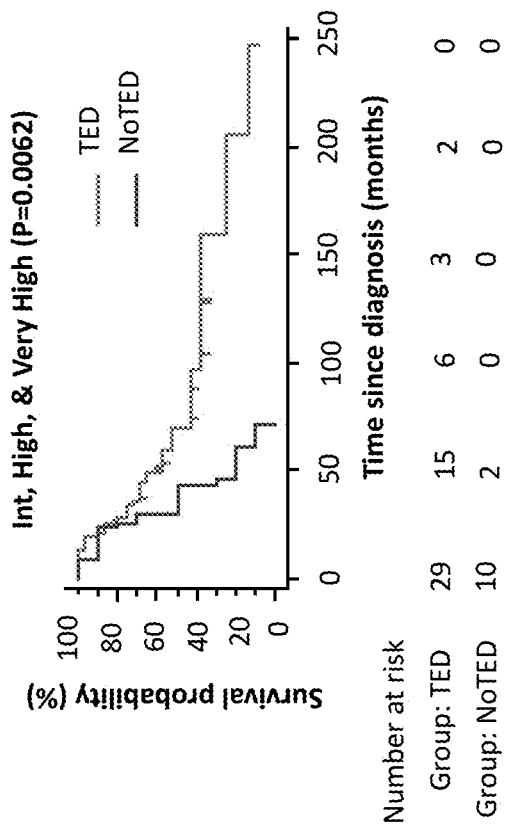
FIG. 5G is a survival curve for patients classified as IPSS-R intermediate, high, and very high categories (P=0.0062).
Figure 6B:
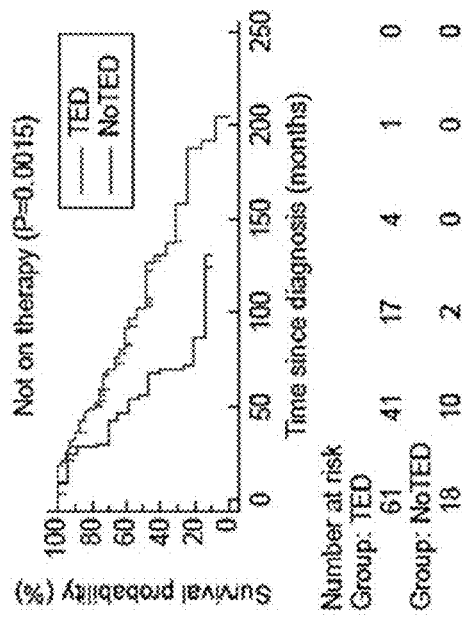
FIG. 6B is a survival curve of SF3B1 mutated and wildtype patients (P=0.1224). OS was different but not significant.
Figure 6C:
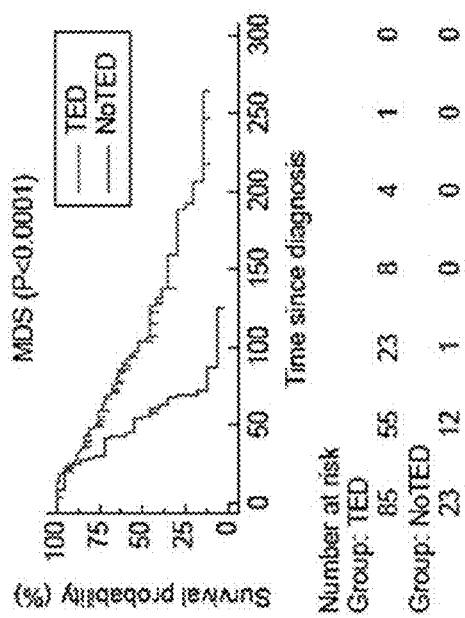
FIG. 6C is a survival curve of TED and NoTED MDS patients excluding SF3B1 mutated patients. There was a significant difference in OS between TED and NoTED MDS patients excluding SF3B1 mutated patients (P=0.0015).
Figure 6D:
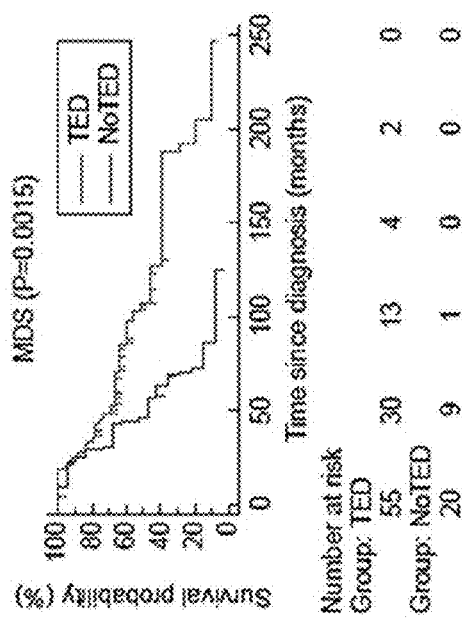
FIG. 6D is a survival curve of patients not on any therapy at sample collection (P=0.0015).

MDS patients with SF3B1 mutations show a better prognosis compared with SF3B1 wild-type patients (Malcovati et al. 2015; Patnaik et al. 2012; Mangaonkar et al. 2018). In the dataset herein (FIG. 6B), a similar better survival rate of MDS patients with SF3B1 mutations (median, 94.9 months) was seen compared with SF3B1 wild-type (median, 71.8 months). To alleviate the concern that the better OS of patients with an SF3B1 mutation might explain the better prognosis of TED-positive patients (FIG. 6B), because most of the SF3B1-mutated patients were TED-positive, an OS analysis excluding patients with mutations in the SF3B1 gene was performed (FIG. 6C). OS between TED-positive and TED-negative groups was still significantly different after excluding SF3B1 patients (P=0.0015; FIG. 6C). The median survival of the TED-positive group (106 months) was not much different after excluding the SF3B1 group, suggesting that the observed differences were not because of SF3B1-mutated patients. The difference persisted within each subgroup examined: RCMD (P=0.0041; FIG. 5B) and RAEB-1/2 (P=0.029; FIG. 5C). When TED-positive samples were divided by those with mutations in SF3B1 or SRSF2, OS was worse for those with TED and SRSF2 (P=0.0132; FIG. 5D). OS was significantly different within lower and higher risk IPSS-R categories (FIG. 5E-H; Table 11). OS analysis of a subset of patients who were not on any therapy at the time of sample collection still showed a significant difference between TED and NoTED (P=0.0015) (FIG. 6D). The survival of patients with M:E ratio ≥5 was worse than those with patient with a <5M:E ratio (P=0.0005).

TABLE 9

Patients TED status, time since diagnosis, transfusion requirements, and whether the data is censored, alive/0, dead/1 at the time of study.

| Sl. No. | Unique Patient ID - repeat order | TED status | Time since diagnosis | Censored | Transfusion requirements |
|---|---|---|---|---|---|
| 1 | 2-1 | TED | 86.1 | 0 | Independent |
| 2 | 3-1 | TED | 78.83 | 0 | Dependent |
| 3 | 4-1 | TED | 36.9 | 0 | Dependent |
| 4 | 5-1 | TED | 19.77 | 1 | Dependent |
| 5 | 6-1 | NoTED | 42.23 | 1 | Dependent |
| 6 | 7-1 | TED | 20.53 | 0 | Dependent |
| 7 | 9-1 | TED | 39.3 | 0 | Independent |
| 8 | 10-1 | TED | 88.47 | 0 | Independent |
| 9 | 11-1 | TED | 103.57 | 0 | Dependent |
| 10 | 12-1 | TED | 44.77 | 1 | Dependent |
| 11 | 13-1 | NoTED | 67.73 | 0 | Dependent |
| 12 | 14-1 | TED | 9.63 | 0 | Independent |
| 13 | 15-1 | TED | 81.13 | 1 | Dependent |
| 14 | 16-1 | NoTED | 71.83 | 1 | Dependent |
| 15 | 17-1 | TED | 94.9 | 1 | Independent |
| 16 | 18-1 | TED | 106.7 | 1 | Independent |
| 17 | 19-1 | TED | 247.2 | 0 | Independent |
| 18 | 20-1 | TED | 48.23 | 1 | Dependent |
| 19 | 21-1 | TED | 76.1 | 1 | Independent |
| 20 | 22-1 | TED | 129.83 | 0 | Independent |
| 21 | 24-1 | TED | 66.53 | 0 | Independent |
| 22 | 25-1 | TED | 70 | 1 | Independent |
| 23 | 26-1 | TED | 71.33 | 0 | Dependent |
| 24 | 27-1 | TED | 27.27 | 1 | Dependent |
| 25 | 28-1 | TED | 92 | 1 | Dependent |
| 26 | 31-1 | NoTED | 43.6 | 1 | Dependent |
| 27 | 32-1 | TED | 33.17 | 1 | Independent |
| 28 | 34-1 | TED | 192.47 | 1 | Independent |
| 29 | 35-1 | TED | 76.97 | 0 | Dependent |
| 30 | 36-1 | TED | 97.3 | 1 | Dependent |
| 31 | 37-1 | NoTED | 9.1 | 1 | Dependent |
| 32 | 38-1 | TED | 48.87 | 1 | Dependent |
| 33 | 39-1 | TED | 85.6 | 0 | Dependent |
| 34 | 40-1 | NoTED | 28.7 | 1 | Dependent |
| 35 | 41-1 | NoTED | 23.2 | 1 | Dependent |
| 36 | 42-1 | TED | 51.17 | 0 | Independent |
| 37 | 43-1 | NoTED | 69.93 | 1 | Dependent |
| 38 | 45-1 | TED | 28.77 | 0 | Independent |
| 39 | 46-1 | NoTED | 69.43 | 1 | Independent |
| 40 | 47-1 | TED | 51.87 | 1 | Dependent |
| 41 | 48-1 | TED | 218.1 | 0 | Dependent |
| 42 | 49-1 | NoTED | 43.63 | 1 | Independent |

TABLE 9-continued

Patients TED status, time since diagnosis, transfusion requirements, and whether the data is censored, alive/0, dead/1 at the time of study.

| Sl. No. | Unique Patient ID - repeat order | TED status | Time since diagnosis | Censored | Transfusion requirements |
|---|---|---|---|---|---|
| 43 | 50-1 | TED | 21.6 | 1 | Independent |
| 44 | 51-1 | TED | 159 | 1 | Dependent |
| 45 | 52-1 | TED | 56.4 | 0 | Independent |
| 46 | 54-1 | TED | 92.87 | 0 | Dependent |
| 47 | 55-1 | TED | 138.43 | 0 | Dependent |
| 48 | 56-1 | TED | 59 | 0 | Independent |
| 49 | 57-1 | NoTED | 29 | 1 | Dependent |
| 50 | 58-1 | TED | 70.37 | 1 | Independent |
| 51 | 59-1 | TED | 89.5 | 1 | Independent |
| 52 | 60-1 | NoTED | 29.87 | 1 | Dependent |
| 53 | 61-1 | TED | 72.93 | 0 | Dependent |
| 54 | 62-1 | NoTED | 63.13 | 1 | Dependent |
| 55 | 63-1 | TED | 51.13 | 0 | Dependent |
| 56 | 65-1 | TED | 42.7 | 0 | Independent |
| 57 | 66-1 | NoTED | 86.77 | 1 | Dependent |
| 58 | 67-1 | TED | 59.63 | 1 | Independent |
| 59 | 69-1 | TED | 122.53 | 0 | Dependent |
| 60 | 70-1 | TED | 52.93 | 0 | Independent |
| 61 | 71-1 | TED | 107.3 | 0 | Dependent |
| 62 | 72-1 | TED | 48.63 | 1 | Independent |
| 63 | 73-1 | TED | 137.57 | 1 | Dependent |
| 64 | 74-1 | TED | 122.6 | 0 | Independent |
| 65 | 75-1 | TED | 264.9 | 0 | Dependent |
| 66 | 76-1 | NoTED | 54.47 | 1 | Dependent |
| 67 | 77-1 | TED | 25.37 | 1 | Independent |
| 68 | 78-1 | TED | 67 | 0 | Independent |
| 69 | 79-1 | TED | 32.1 | 1 | Independent |
| 70 | 80-1 | NoTED | 130.5 | 0 | Dependent |
| 71 | 81-1 | TED | 49.83 | 0 | Dependent |
| 72 | 82-1 | TED | 83.93 | 0 | Dependent |
| 73 | 83-1 | TED | 18.9 | 1 | Dependent |
| 74 | 84-1 | TED | 158.87 | 0 | Independent |
| 75 | 86-1 | TED | 53.2 | 0 | Independent |
| 76 | 88-1 | TED | 105.73 | 0 | Independent |
| 77 | 89-1 | TED | 27.9 | 1 | Dependent |
| 78 | 90-1 | TED | 103.07 | 1 | Independent |
| 79 | 91-1 | TED | 114.53 | 0 | Independent |
| 80 | 92-1 | NoTED | 25.03 | 1 | Dependent |
| 81 | 93-1 | TED | 102.9 | 1 | Dependent |
| 82 | 95-1 | TED | 131.17 | 1 | Dependent |
| 83 | 97-1 | TED | 26.1 | 0 | Dependent |
| 84 | 98-1 | TED | 59.93 | 0 | Independent |
| 85 | 99-1 | TED | 83.23 | 0 | Independent |
| 86 | 100-1 | TED | 126.43 | 1 | Dependent |
| 87 | 101-1 | NoTED | 57.6 | 0 | Independent |
| 88 | 102-1 | TED | 13.53 | 1 | Independent |
| 89 | 103-1 | TED | 67.93 | 1 | Dependent |
| 90 | 104-1 | TED | 128.43 | 0 | Dependent |
| 91 | 105-1 | NoTED | 46.23 | 1 | Dependent |
| 92 | 106-1 | TED | 35.07 | 0 | Dependent |
| 93 | 107-1 | TED | 73.37 | 0 | Independent |
| 94 | 108-1 | NoTED | 60.43 | 1 | Dependent |
| 95 | 110-1 | TED | 18.67 | 1 | Dependent |
| 96 | 111-1 | TED | 78.33 | 0 | Dependent |
| 97 | 112-1 | NoTED | 124.93 | 0 | Dependent |
| 98 | 113-1 | TED | 48 | 1 | Independent |
| 99 | 114-1 | TED | 63.97 | 1 | Dependent |
| 100 | 115-1 | NoTED | 67.97 | 0 | Dependent |
| 101 | 116-1 | TED | 48.8 | 0 | Dependent |
| 102 | 117-1 | TED | 187.87 | 0 | Independent |
| 103 | 118-1 | NoTED | 55.77 | 1 | Dependent |
| 104 | 122-1 | TED | 43.17 | 1 | Independent |
| 105 | 123-1 | TED | 36.87 | 0 | Independent |
| 106 | 124-1 | TED | 35.1 | 1 | Dependent |
| 107 | 125-1 | TED | 4.1 | 0 | Independent |
| 108 | 126-1 | TED | 40.03 | 0 | Independent |
| 109 | 128-1 | TED | 205.57 | 1 | Independent |
| 110 | 129-1 | TED | 24.63 | 1 | Independent |
| 111 | 130-1 | TED | 36.5 | 1 | Independent |
| 112 | 131-1 | NoTED | 21.67 | 0 | Dependent |
| 113 | 133-1 | TED | 3.97 | 0 | Independent |

TABLE 10

Patient Characterstics and Association with Median Survival

| | N | % | Median Survival (months) | (95% CI) | p-value |
|---|---|---|---|---|---|
| Age | | | | | |
| <55 yrs. | 5 | 4.4 | 70 | 70.0 to 71.8 | 0.6337 |
| 55-64 yrs. | 14 | 10.6 | — | — | |
| 65-74 yrs. | 49 | 43.3 | 81.13 | 67.9 to 131.1 | |
| ≥75 yrs | 45 | 39.8 | 85.6 | 48.6 to 126.4 | |
| Total | 113 | | | | |
| Sex | | | | | |
| Female | 46 | 40.7 | 85.6 | 48.8 to 205.5 | 0.9382 |
| Male | 67 | 59.3 | 92 | 69.4 to 126.4 | |
| WHO 2008 | | | | | |
| RA | 9 | 8 | 103. | 63.1 to 103.0 | 0.002 |
| RCMD | 11 | 9.8 | — | — | |
| RARS | 59 | 52.6 | 86.7 | 69.4 to 126.4 | |
| RAEB-1 | 15 | 13.3 | 46.2 | 27.2 to 70.0 | |
| RAFEB-2 | 13 | 11.6 | 48.6 | 28.7 to 205.5 | |
| RARS-T | 5 | 4.4 | — | — | |
| Total | 112 | | | | |
| IPSS Risk Categories | | | | | |
| Low | 29 | 32.2 | 131.1 | 81.1 to 192.4 | 0.0154 |
| Int-1 | 46 | 48.8 | 94.9 | 60.4 to 126.3 | |
| Int-2 | 11 | 12.2 | 35.1 | 25.3 to 70. | |
| high | 6 | 6.6 | 25 | 23.2 to 205.5 | |
| Total | 90 | | | | |
| Karyotype (IPSS) | 70 | 66 | 94.9 | 76.1 to 131.1 | 0.0219 |
| Good | 29 | 24 | 67.9 | 48.6 to 205.5 | |
| intermediate | 12 | 11.3 | 43.6 | 25.3 to 70.0 | |
| Poor | | | | | |
| Total | 106 | | | | |
| IPSS-R Risk Categories | | | | | |
| Very Low | 19 | 21.1 | 137.57 | 81.1 to 137.5 | 0.0026 |
| Low | 32 | 35.5 | 103 | 85.6 to 187.8 | |
| Intermediate | 21 | 23.3 | 60.43 | 44.770 to 159.000 | |
| High | 10 | 11.1 | 27.9 | 23.2 to 97.3 | |
| Very High | 8 | 8.8 | 25.3 | 19.7 to 205.5 | |
| Total | 90 | | | | |
| Karyotype (IPSSR) | | | | | |
| Very good | 3 | 3 | 137.5 | 21.6 to — | 0.075 |
| Good | 69 | 63 | 94.9 | 71.1 to 131.1 | |
| Intermediate | 22 | 21 | 63.1 | 48.6 to 205.5 | |
| Poor | 5 | 4 | 67.9 | 13.5 to 67.9 | |
| Very poor | 7 | 9 | 43.6 | 19.7 to 70.0 | |
| Total | 106 | | | | |
| Blast | | | | | |
| ≤2 | 65 | 59.5 | 126.4 | 89.5 to 192.4 | 0.0002 |
| 2.1-4.9 | 15 | 13.7 | 85.6 | 42.2 to 131.1 | |
| 5-10 | 19 | 17.4 | 54.4 | 44.7 to 70.3 | |
| >10 | 10 | 9.1 | 35.1 | 25.0 to 205.5 | |
| Total | 109 | | | | |
| Hemoglobin (g/dL) | | | | | |
| <8 | 13 | 11.9 | 205.5 | 91.2 to — | 0.0899 |
| 8-9.9 | 48 | 44 | 67.9 | 54.4 to 97.3 | |
| ≥10 | 48 | 44 | 89.5 | 69.9 to 187.8 | |
| Total Absolute | 109 | | | | |

TABLE 10-continued

Patient Characterstics and Association with Median Survival

| | N | % | Median Survival (months) | (95% CI) | p-value |
|---|---|---|---|---|---|
| Neutrophil Count (109/L) | | | | | |
| <0.8 | 19 | 18.8 | 70 | 29.0 to 97.3 | 0.2058 |
| ≥0.8 | 82 | 81.1 | 92 | 69.9 to 126.4 | |
| Total | 101 | | | | |
| Platelets (109/L) | | | | | |
| <50 | 22 | 20.1 | 97.3 | 35.1 to 187.8 | 0.6999 |
| 50-99 | 23 | 21.1 | 81.1 | 60.4 to 106.7 | |
| ≥100 | 64 | 58.8 | 85.6 | 67.9 to 131.1 | |
| Total | 109 | | | | |
| TED | | | | | |
| TED-positive | 89 | 78.7 | 103 | 89.6 to 137.5 | 0.0001 |
| TED-negative | 24 | 21.3 | 55.7 | 43.6 to 69.4 | |
| Total | 113 | | | | |

TABLE 11

OS among various IPSS-R categories

| | | Median Survival (mo) | | |
|---|---|---|---|---|
| Sl. No. | IPSS-R Category | TED | No TED | P value |
| 1 | Very Low, Low, Intermediate | 126.4 | 55.7 | <0.0001 |
| 2 | Very Low, Low | 126.4 | 69.9 | 0.0278 |
| 3 | High, Very High | 48.6 | 23.2 | 0.0059 |
| 4 | Intermediate, High, Very High | 70 | 29.8 | 0.0062 |

Figures 6E, 6F:
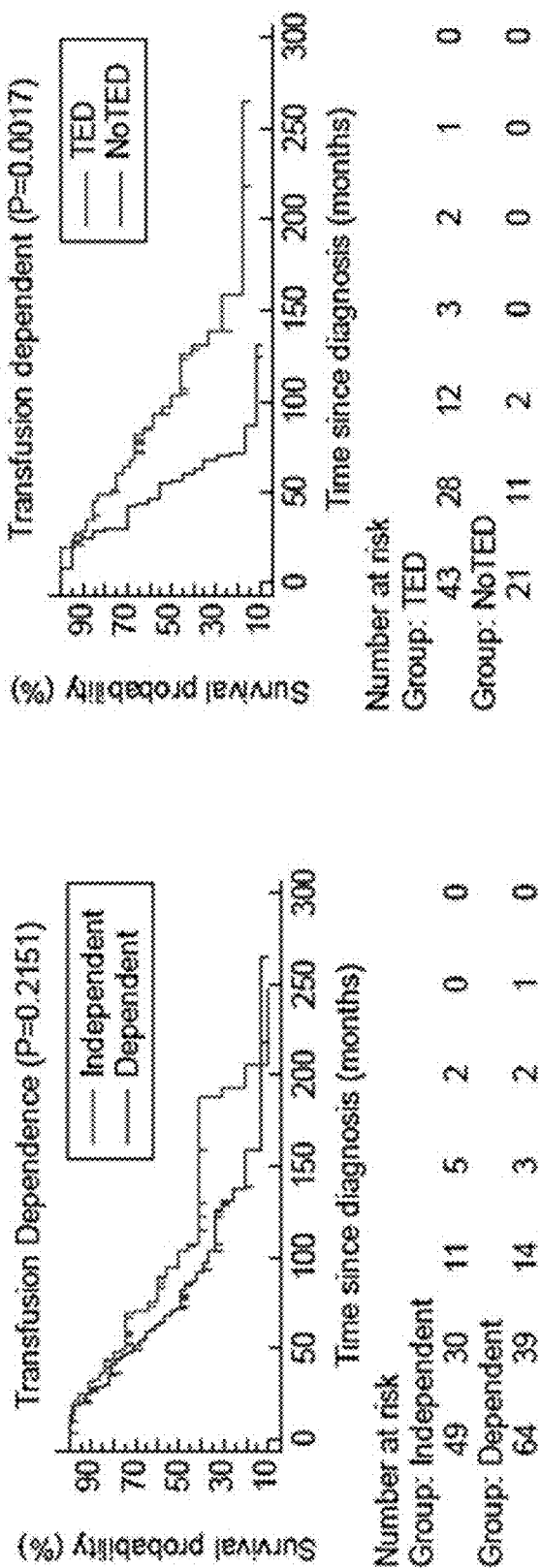
FIG. 6E is a survival curve of transfusion dependent and independent patients (P=0.2151).
FIG. 6F is a survival curve of TED and noTED patients who were transfusion dependent at sample collection (P=0.0017). OS was significantly different between TED and noTED patients who were transfusion dependent at sample collection. Log-rank test was used to compare the curves. The tables below the curves indicate the number of patients at risk in each group.
Figure 7:
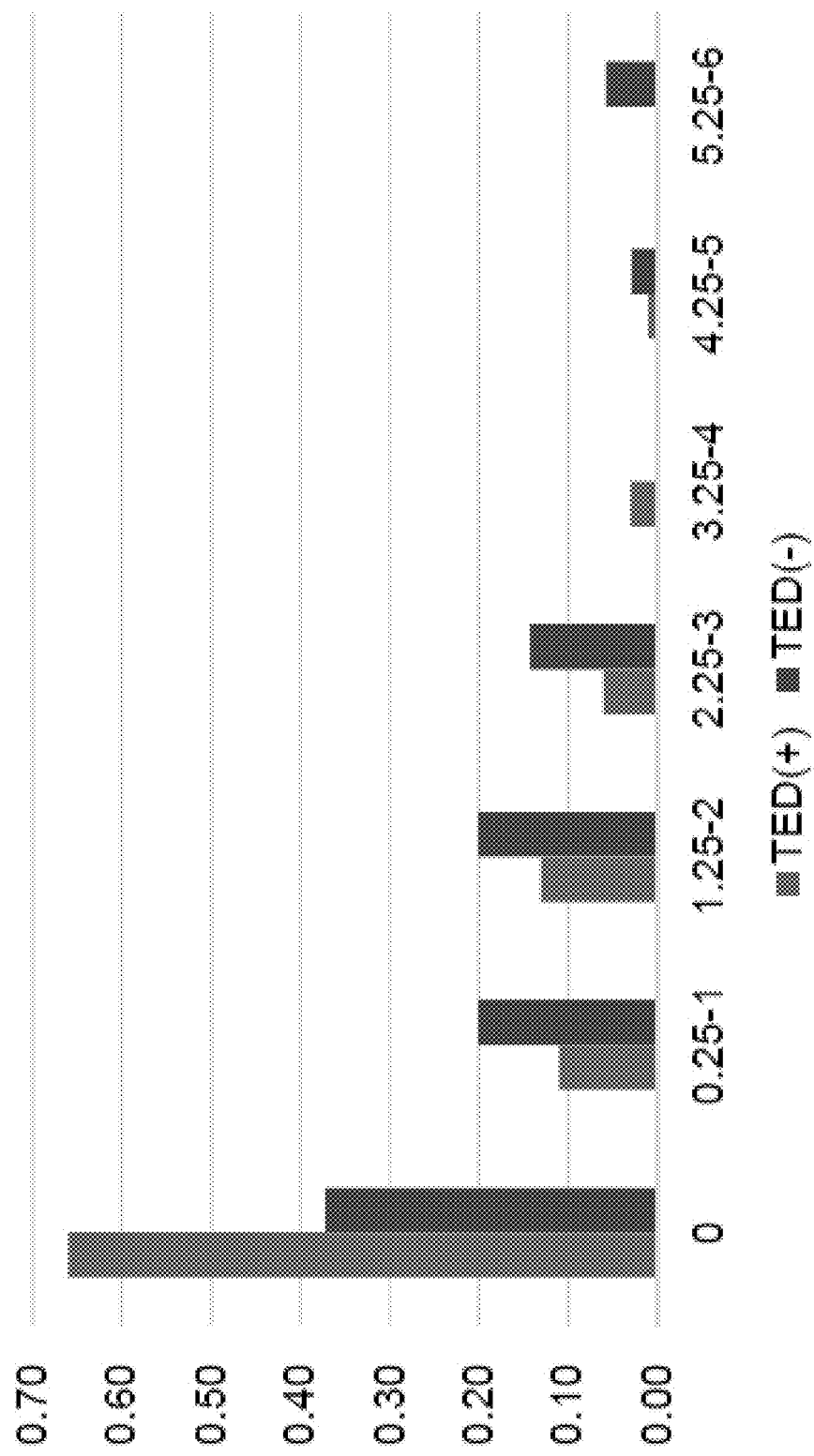
FIG. 7 is a graph of the transfusion rate (units/month) between TED and noTED patients. Twice as many patients who were TED-negative (noTED) were transfusion dependent compared to TED-positive (TED+). Also, the transfusion requirements of TED-negative patients were more than TED-positive.

Example 8—Results of TED Analysis—TED Versus Red Blood Cell Transfusion Dependence Transfusion data were available on all 113 unique patients. Patients were considered transfusion-dependent if they had received at least two units of red blood cells (RBC) within the last 56 days prior to their first sample collected for this study. Fifty-seven percent (64/113) were transfusion-dependent. Among the noTED, 88% (21/24) were transfusion-dependent whereas among the TED, 46% (43/89) were transfusion dependent (P=0.0005). Within the transfusion-dependent patients, transfusion requirements were higher in the noTED group (FIG. 7). The median survival of transfusion-dependent patients (72 months) was lower than transfusion-independent patients (103 months; FIG. 6E). Within the transfusion dependent patients, there was a significant difference in survival based on their TED status (P=0.0017; FIG. 6F).

Example 9—Results of TED Analysis—Multivariate Survival Model Using Presence or Absence of TED In a univariate analysis, absence of TED, IPSS-R, and M:E ratio (≥5) and presence of mutation in CEBPA, CUX1, IDH2, NRA5, RUNX1, SRSF2, and STAG2 was significantly associated with survival in MDS patients (Table 12). To determine the contribution of significant factors affecting survival, a multivariable Cox proportional hazards regression model was generated, using a stepwise variable selection procedure, incorporating variables noted previously except CEBPA, IDH2, and NRAS, which were present in <3% of patients. TED and the IPSS-R risk categories high and very high and mutations in CUX1 and STAG2 remained significant (Table 13). The same final model was obtained using a forward selection method.

TABLE 12

Hazard Ratios for Death in a Univariate Analysis

| Factor | HR | 95% CI of HR | P |
|---|---|---|---|
| TED | 3.4 | 1.9 to 6.1 | <0.0001 |
| ME Ratio | 3.1 | 1.5 to 6.3 | 0.001 |
| IPSSR | 1.4 | 1.1 to 1.8 | 0.0006 |
| CEBPA | 5.1 | 1.2 to 21.7 | 0.0264 |
| CUX1 | 4.1 | 1.5 to 10.8 | 0.0035 |
| IDH2 | 12.2 | 2.5 to 57.9 | 0.0016 |
| NRAS | 5.3 | 1.6 to 17.6 | 0.0061 |
| RUNX1 | 2.4 | 1.2 to 4.8 | 0.0105 |
| SRSF2 | 3.1 | 1.6 to 6.0 | 0.0005 |
| STAG2 | 4.3 | 1.7 to 11.1 | 0.0021 |

TABLE 13

Hazard Ratios for death in a multivariable model.*

| Covariate | P | HR | 95% CI of HR |
|---|---|---|---|
| TED (quantifiable vs NoTED) | 0.0001 | 4.9 | 2.1 to 11.0 |
| IPSSR (High vs Low) | 0.0035 | 3.7 | 1.5 to 9.0 |
| IPSSR(Very high vs low) | 0.031 | 2.7 | 1.0 to 6.8 |
| CUX1 (absent vs present) | 0.0157 | 3.5 | 1.2 to 9.6 |
| STAG2 (absent vs present) | 0.045 | 3.0 | 1.0 to 9.1 |

*the model include TED (quantifiable or not), IPSS-R (very low, low, intermediate, high, and very high), ME ratio (<5 and >=5), and presence or absence of mutation in CUX1, RUNX1, SRSF2, and STAG2.

Example 10—RNA SEQ Data

As shown in the previous examples, using a recently developed flow cytometry based method, TED was examined in more than 200 samples from 126 unique MDS patients and identified two distinct subsets: two-third of the patients showed sufficient number of cells undergoing TED (TED+) while the remaining one-third had too few cells undergoing TED (TED−) despite having adequate numbers of hematopoietic cells for flow cytometry analysis. Compared to TED+, the TED− patients were associated with higher myeloid:erythroid (M:E) ratio (mean 5.7:1), more profound anemia (P=0.0003), higher blasts (P=0.0030), but lower absolute neutrophil count (P=0.0245). It was also found that the TED− cases were associated with significantly worse overall survival (56 versus 103 months, P<0.0001).

To identify differences at the molecular level between the TED+ (n=23) and TED− (n=19) patients and to generate a gene expression based signature, the RNA from bone marrow mononuclear cells was sequenced using next generation sequencing (NGS). To identify the biological processes and pathways that are deregulated in TED− patients, Gene Set Enrichment Analysis (GSEA) and Database for Annotation, Visualization and Integrated Discovery (DAVID) analyses was performed to identify significantly differentially expressed genes (>0.5 and <−0.5 log fold change) using DESeq2 and edgeR packages.

Materials and Methods

Total RNA was isolated from bone marrow mononuclear cells (BM MNC) of TED+ (n=23) and TED− (n=19) patients. The BM MNCs were lysed in Trizol and Qiagen Rneasy kit was used for RNA isolation. RNA quality was checked using Agilent's Bioanalyzer. An Illumina's TruSeq Stranded mRNA library was prepared and sequenced using Illumina's HiSeq2500/4000 sequencer. 100-bp was sequenced on both ends of the DNA fragment to generate 60 million reads. Illumina's RTA was used for base calling (BCL) and the BCL file is converted to a fastQ formation using bcl2fastq2 v2.17.

The fastQ data was then mapped to human genome NCBI build 37.2 using STAR (v2.5.2b) program and a BAM file was generated. Reads that mapped to each gene was counted using featureCount (v1.5.0-p3).

The count data was transformed using Variance Stabilizing Transformation (VST) method. Variability within the data was measured using principal component analysis (PCA) and the samples clustering was done using hierarchical clustering of the whole sample set. Data normalization was done using the DESeq or edgeR methods. Differential gene expression analysis was done using DESeq2 and edgeR packages of Bioconductor packages of R program.

The RNeasy Mini kit was used for total RNA extraction. RNA concentrations and quality were measured with Bioanalyzer. RNA integrity number (RIN) with >9 was used for RNAseq and qPCR. cDNA was produced starting with 1 ug of total RNA using Superscript II reverse transcriptase. Primers for qPCR of 76 genes was designed using D3 Assay Design software (Fluidigm). Primer specificity and assay efficiency was tested and primers pairs that threshold cycle (Ct) lower than 40 and showing a single dominant peak in the melting curve, and no amplification of non-template controls were selected. Preamplification was used to increase the number of template molecules. qPCR was performed using the high-throughput microfluidic qPCR platform BioMark™ (Fluidigm) and 96.96 dynamic array. SYBR Green and ROX was used for measuring fluroscence. Measured Ct values were exported from the BioMark™ platform software to Excel and expression ratios were calculated by the delta Ct method, substracting Ct of a average of reference gens from Ct of given.

Results

Figure 8A:
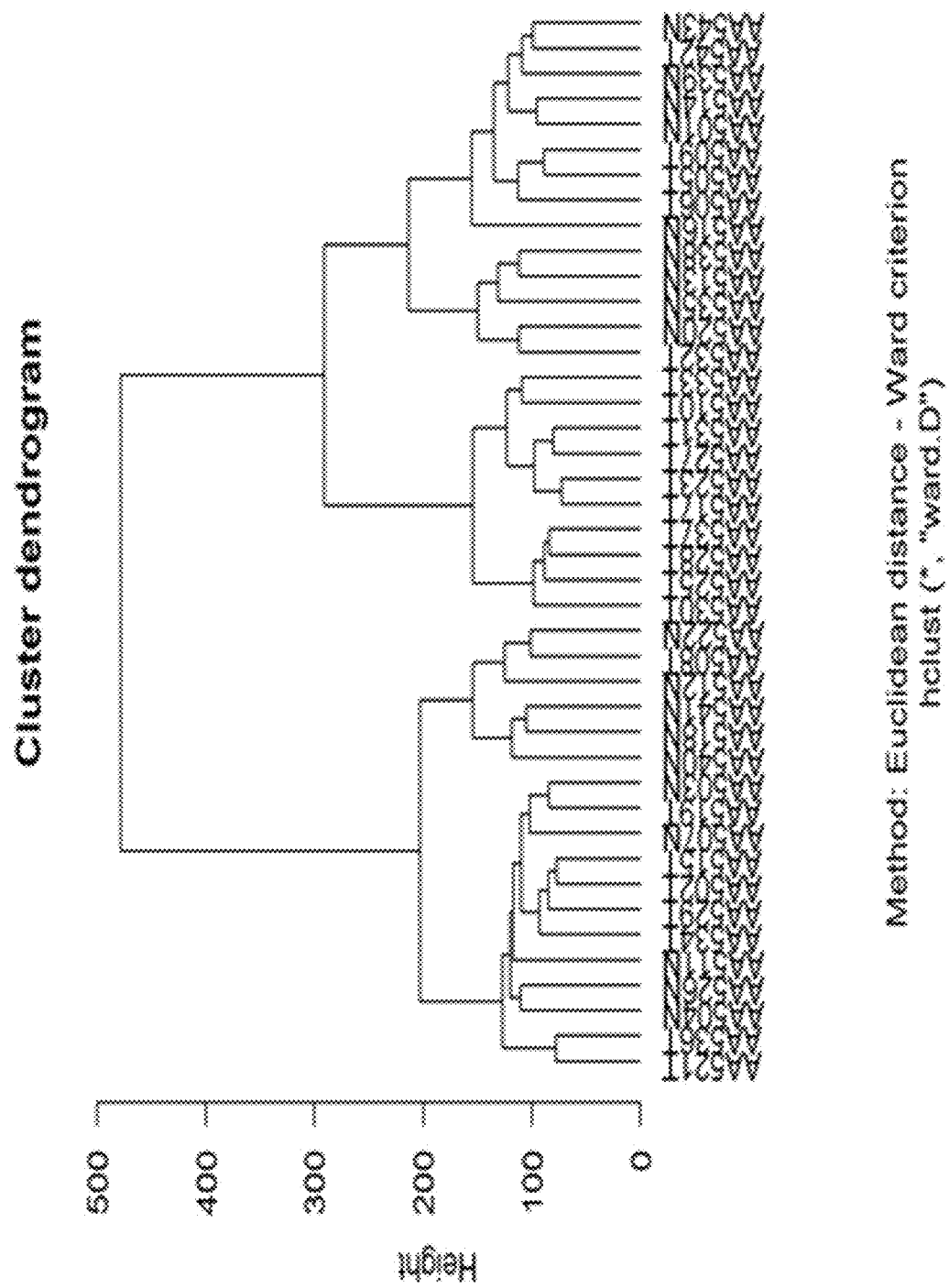
FIG. 8A shows the hierarchical clustering.
Figure 9A:
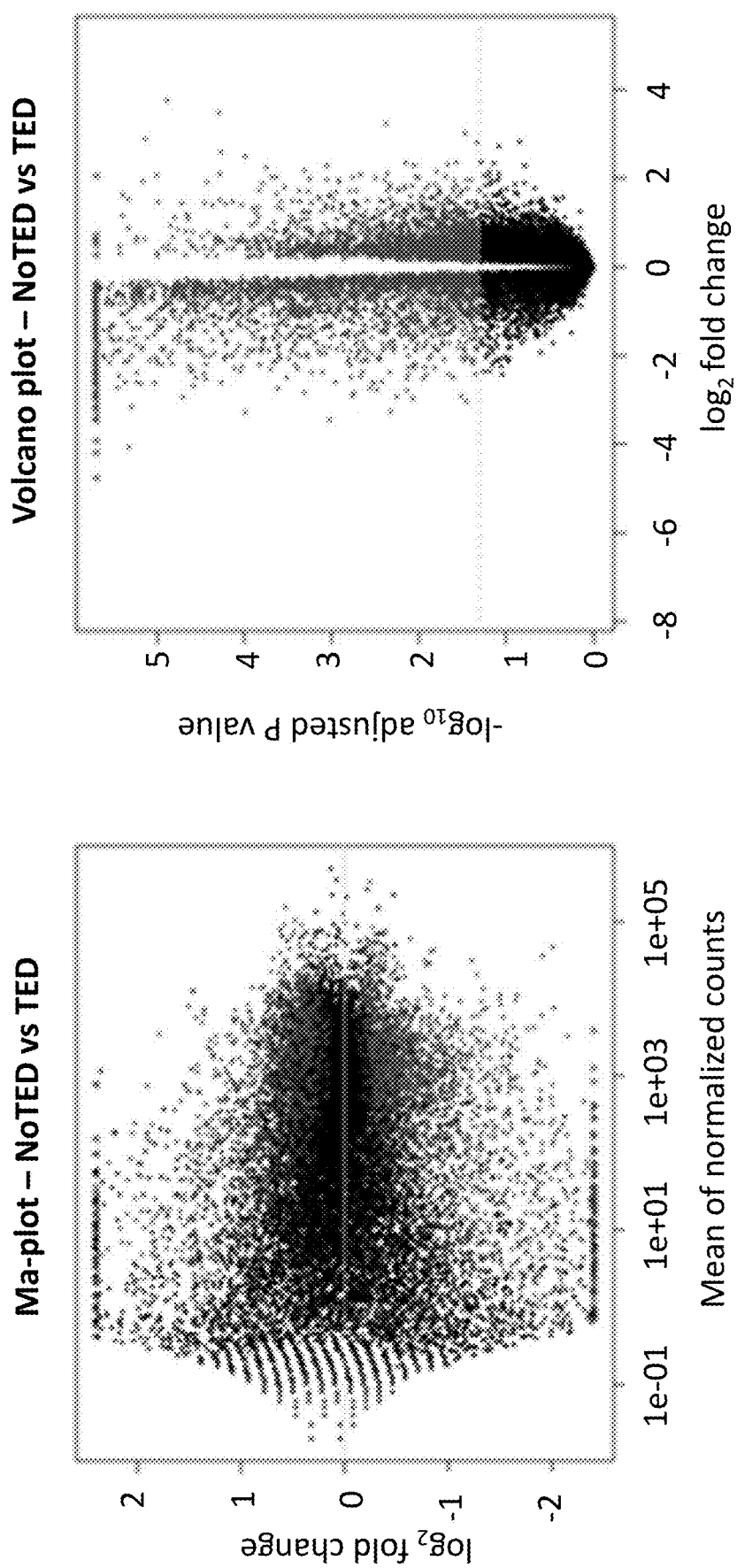
FIG. 9A shows the DESeq program used to find differentially expressed genes.
Figures 9C, 9D:
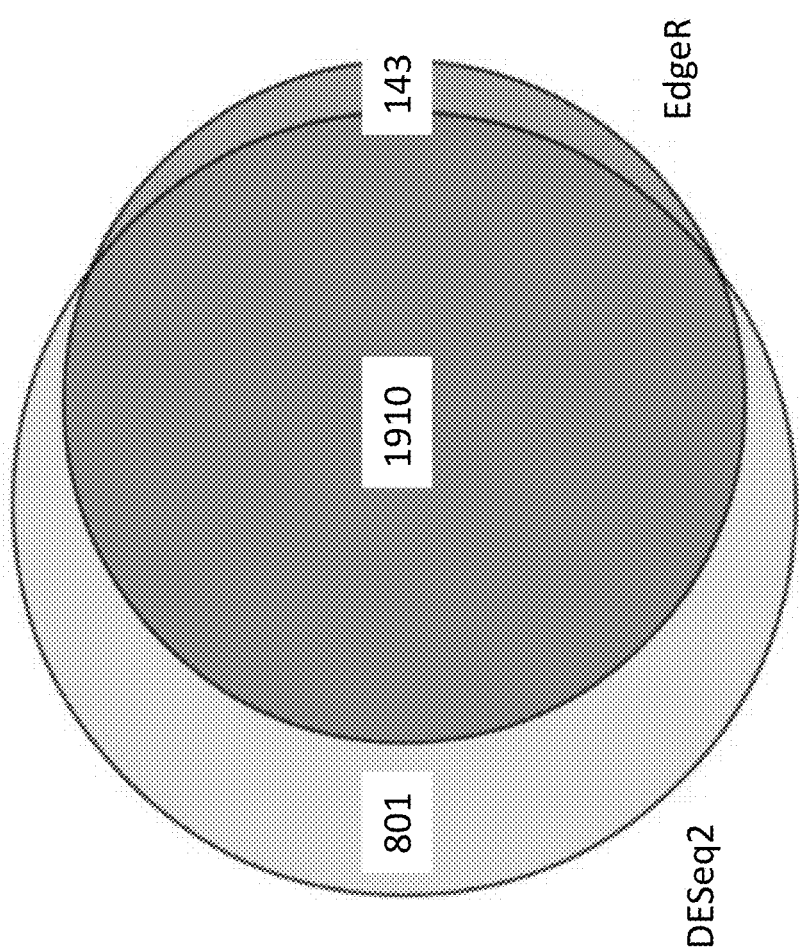
FIG. 9C is a table showing number of up and down expression genes in NoTED relative to TED.
FIG. 9D is a chart of showing 1910 genes that were common to the list with DESeq2 and edgeR.

PCA analysis using shifted logarithm transformation (ntd) of RNAseq data identified several gene clusters; in general TED+ samples were closer to each other than TED− samples (FIGS. 8A and 8B). A total of 2711 genes showed differential expression, 1572 down regulated and 1139 up regulated (FIGS. 9A-D). Both GSEA and DAVID analyses of significantly down-regulated genes showed a marked enrichment of biological processes including heme biosynthesis, erythroid differentiation, and cell cycle, all of which are associated with TED (Table 14). Significantly up-regulated genes were associated with apoptosis, interferon signaling, TNFα, IL6, and IL2 signaling (Table 15). Although, it is not clear which cell types are producing these cytokines, one likely cell type could be T-cells. A significantly higher percentage of $CD4^+$ cells in the bone marrows of TED− group (P=0.0162) was seen, as assessed by immunophenotyping of various T, B, and plasma cell populations. Also, a CIBERSORT analysis of RNAseq data which estimates the abundance of immune cells in a mixture of cell population showed a significantly higher number of $CD4^+$ cell proportion in TED− group (P=0.0109) (FIGS. 10A and 10B).

Figure 11C:
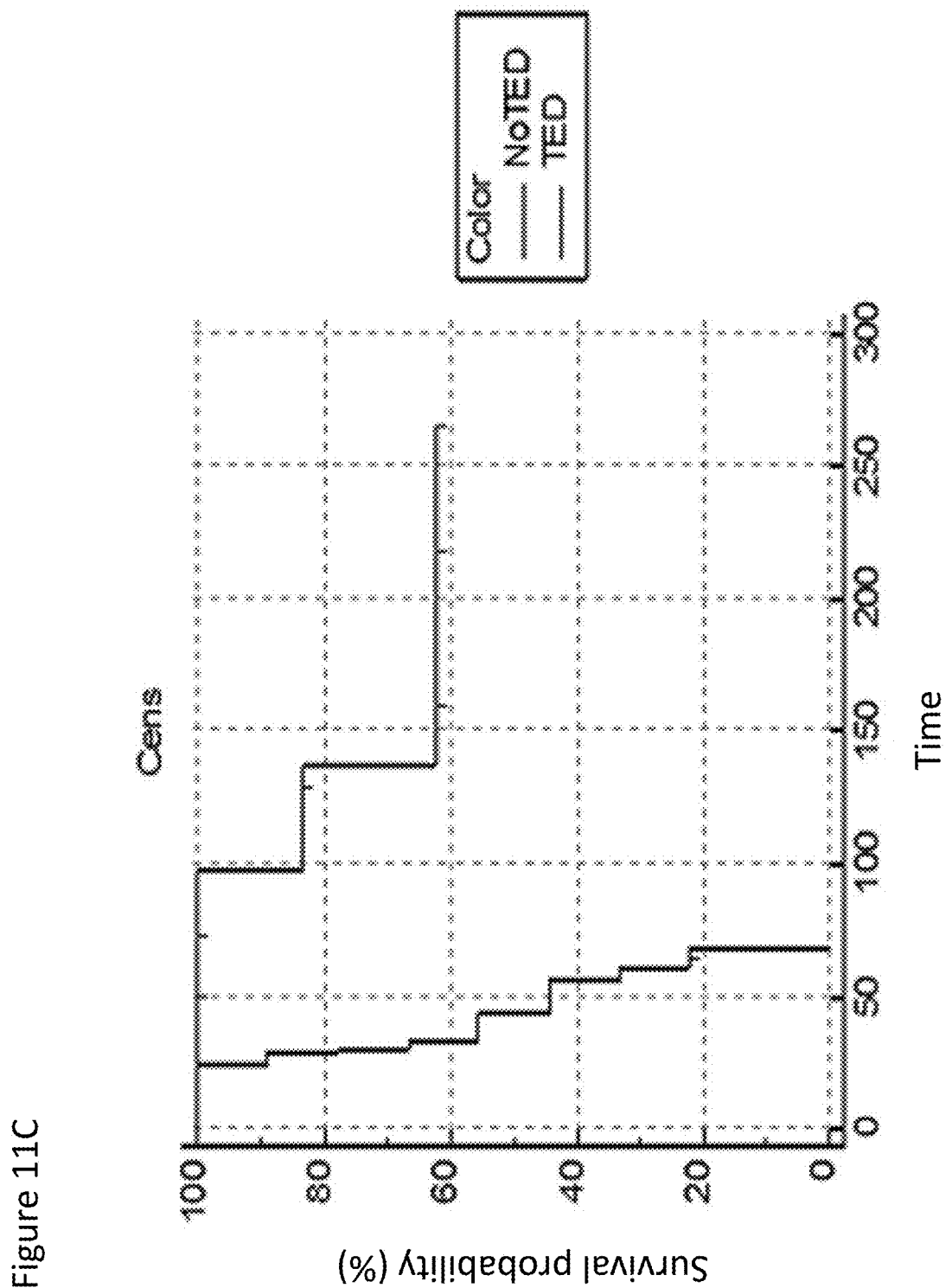
FIG. 11C is a survival curve of the TED and NoTED groups (identified in FIG. 11B). The survival of NoTED is significantly poor.

Using GSEA ranking 100 genes (top 50 up-regulated and top 50 down-regulated) were identified that cluster TED+ and TED− samples into two groups (FIG. 11A). Also, using a 10-gene panel of highly expressed genes during TED, a clustering of TED+ and TED− groups was seen (FIG. 11B). A Kaplan-Meier overall survival analysis of patients who showed a uniform up or down regulation showed a significant difference in survival (FIG. 11C).

Molecular characterization using RNAseq data of TED+ and TED− groups identified several biological pathways deregulated in TED− cases. Given that the RNAseq was done using BM MNC, which is a heterogenous mixture of many different cell types including cells in various TED stages, this "down-regulation" may reflect the loss of cells undergoing TED as observed using flow cytometry. Upregulation of genes involved in cytokine signaling, specially of TNF alpha pathway genes may be a reflection of increased infiltration of $CD4^+$ T cells. Enrichment of genes involved in apoptosis in TED− cases likely represents excessive erythroid cell death and it is likely that this increased apoptosis is due to increased TNF signaling. Distinct RNA expression profiles were associated with presence or absence of cells undergoing TED in MDS patients. Pathways associated with apoptosis and TNF were upregulated while those related to heme synthesis and erythroid differentiation were down-regulated in TED− cases.

It was concluded that that presence or absence of terminal erythroid differentiation identifies two distinct clinical entities within MDS patients with unique molecular profiles that can be identified through RNA sequencing.

Figure 12:
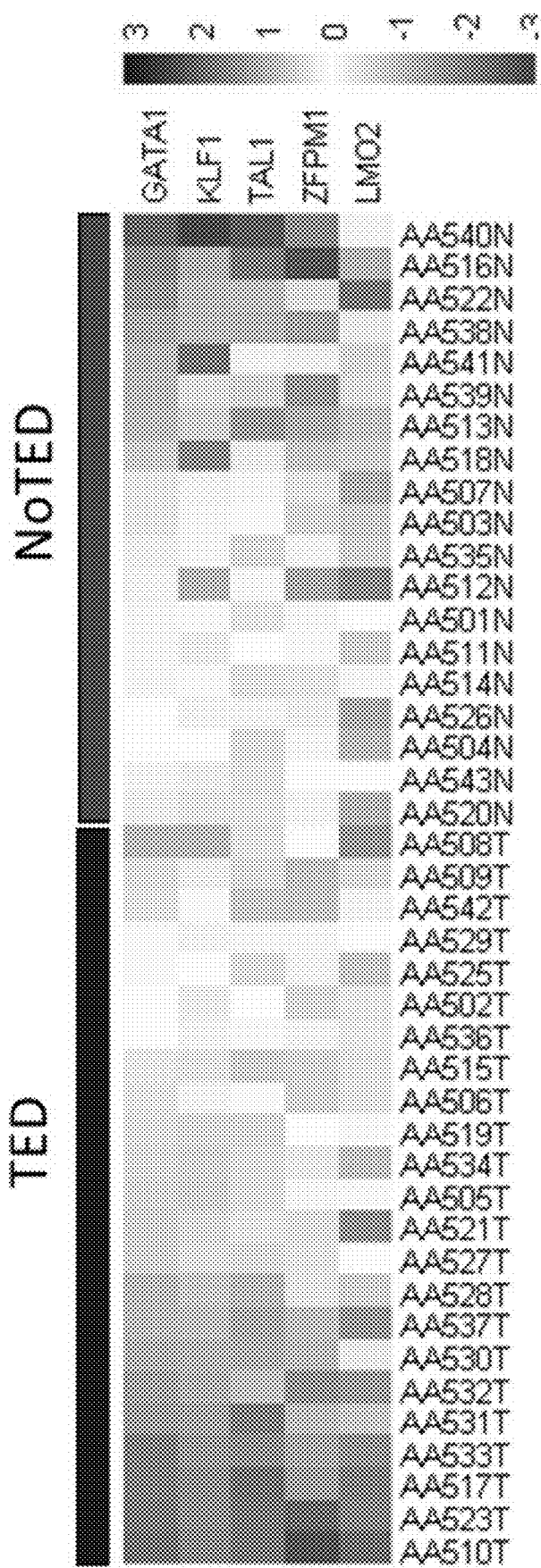
FIG. 12 is a heatmap of gene expression values of transcription factors GATA1, KLF1, TAL1, ZFPM1, and LMO2. These transcription factors showed differential expression between two groups.

Several core erythroid network transcription factors are responsible for TED are GATA1, KLF1, TAL1, ZFPM1 and LMO2. These transcription factors were also significantly differentially expressed between the TED+ and TED− groups (Table 16). In general, the transcription factors were significantly low in TED− group compared to TED+ group (FIG. 12).

To build and test a classifier that can predict TED+ and TED−, weighted voting (signal to noise ratio) class prediction methods comparing gene expression dataset of TED+ and TED− were used. GenePattern software package was used. RNAseq count data was preprocessed and normalized using either the variance stabilizing transformed (VST) count or using transcript per million (TPM). Weighted voting cross-validation identified 77 genes that were used 35 times or more in the classifier with 51 genes used 42 time (Table 17).

Figure 13A:
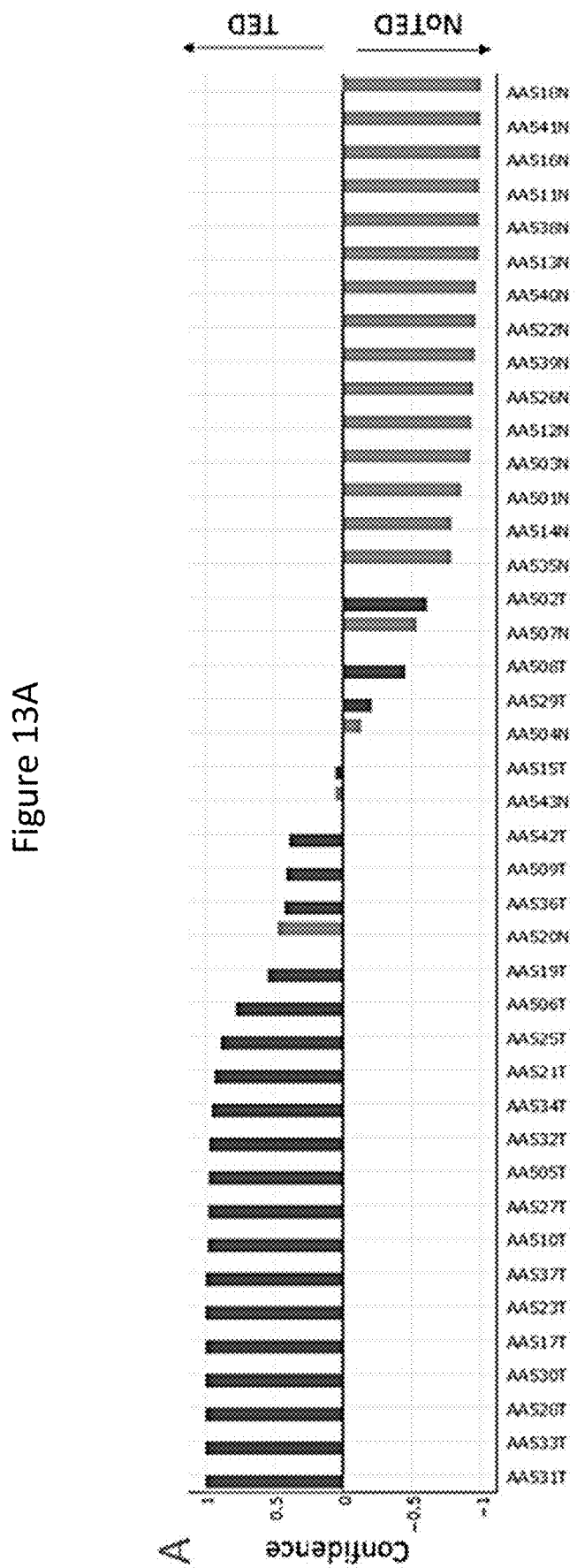
FIG. 13A is a bar diagram showing predicted class of each sample as either TED+ (blue) or TED− (or NoTED; orange).
Figure 13B:
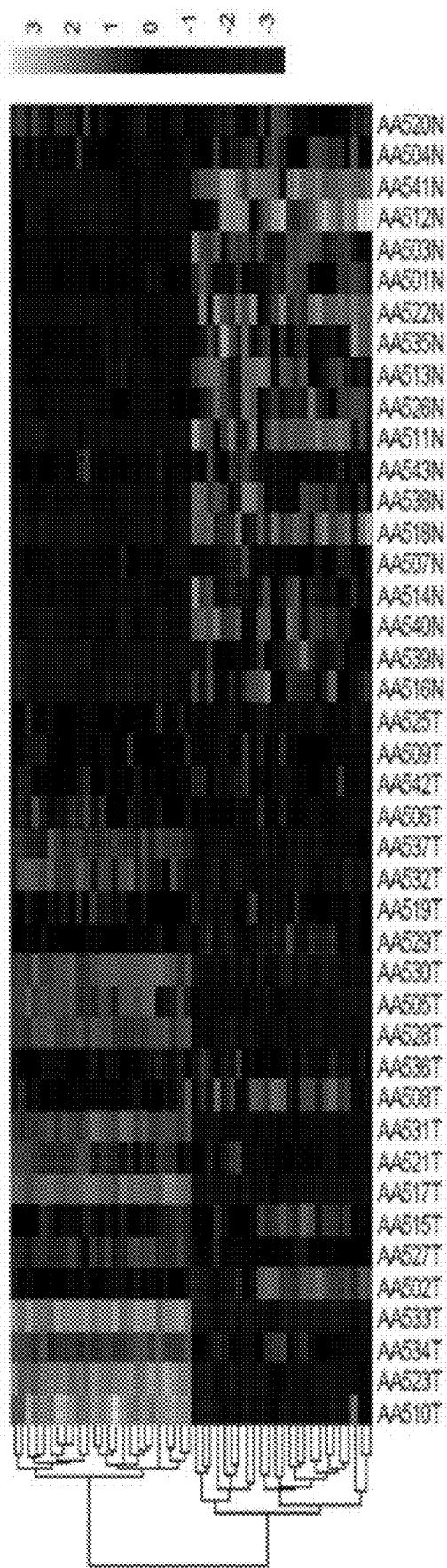
FIG. 13B is a heatmap of gene expression values of the 50 genes classifier.

Two different classifiers were built, one using the VST count and second using transcript per million TPM as input with weighted voting method (Table 18). Also, 50 genes were selected based on GINI index identified using RandomForest. 102 genes were identified between three methods, all which show a predictive power as classifier. 50 genes identified using VST and weighted voting methods were selected and these 50 gene classifier predicted with an absolute error of 0.166 (FIG. 13).

Figure 14:
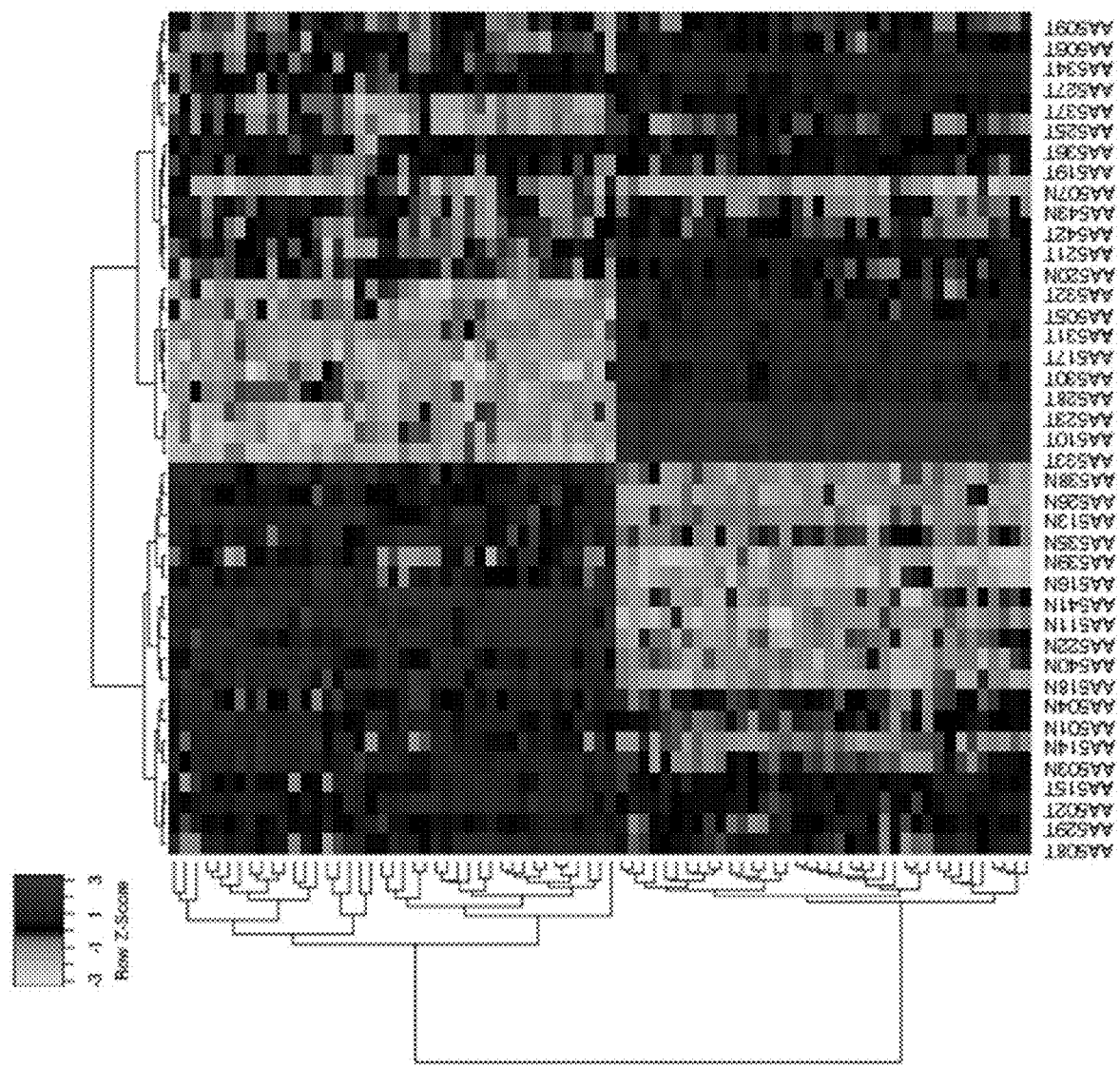
FIG. 14 is a heatmap of gene expression values of 79 genes validated using qPCR. Supervised clustering was performed using Spearman rank correlation and complete linkage. The numbers below the heatmap show the number of TED− in each cluster.

To validate the signatures on an independent platform, the gene expression for 79 genes (Table 19) was measured using a high-throughput microfluidic quantitative PCR (qPCR) platform Biomark HD (Fluidigm). Six reference genes (5S, Actin, GAPDH, TBP, MLN51, and SNORD44) were tested, and three (SNORD44, TBP, 5S) reference genes which showed little variation between the TED+ and TED− dataset were selected. Unsupervised clustering using Spearman correlation with complete linkage, using all 79 genes, resulted in two clusters with one predominantly TED+ (19/22) and one TED− (15/19) (FIG. 14). There was a high correlation between RNAseq and qPCR data.

TABLE 14

A list of genesets enriched for genes that are downregulated TED - groups

| Sl. No. | Category | PValue | Fold Enrichment | FDR |
|---|---|---|---|---|
| 1 | porphyrin-containing compound biosynthetic process | 4.17E−06 | 11.73 | 0.007745 |
| 2 | DNA strand elongation involved in DNA replication | 3.92E−10 | 10.72 | 7.28E−07 |
| 3 | DNA unwinding involved in DNA replication | 1.24E−06 | 10.72 | 0.002298 |
| 4 | heme biosynthetic process | 4.38E−09 | 8.30 | 8.13E−06 |
| 5 | DNA replication initiation | 7.77E−13 | 7.96 | 1.44E−09 |
| 6 | regulation of transcription involved in G1/S transition of mitotic cell cycle | 1.75E−08 | 7.57 | 3.25E−05 |
| 7 | mitotic sister chromatid segregation | 4.61E−09 | 7.50 | 8.56E−06 |
| 8 | telomere maintenance via recombination | 1.90E−09 | 6.70 | 3.53E−06 |
| 9 | DNA duplex unwinding | 4.68E−08 | 5.18 | 8.68E−05 |
| 10 | G1/S transition of mitotic cell cycle | 7.33E−17 | 4.99 | 2.11E−13 |
| 11 | DNA replication | 7.54E−24 | 4.84 | 1.40E−20 |
| 12 | chromosome segregation | 1.88E−09 | 4.53 | 3.49E−06 |
| 13 | sister chromatid cohesion | 2.37E−13 | 4.42 | 4.41E−10 |
| 14 | mitotic nuclear division | 7.33E−20 | 3.57 | 1.36E−16 |
| 15 | cell division | 3.50E−23 | 3.29 | 6.51E−20 |
| 16 | G2/M transition of mitotic cell cycle | 2.68E−06 | 2.74 | 0.004972 |
| 17 | DNA repair | 3.66E−10 | 2.74 | 6.79E−07 |
| 18 | cell proliferation | 2.09E−09 | 2.27 | 3.88E−06 |

TABLE 15

A list of genesets enriched in genes that are upregulated TED- groups

| Sl. No. | Category | PValue | Fold Enrichment | FDR |
|---|---|---|---|---|
| 1 | response to interferon-beta | 1.94E−05 | 14.85 | 0.035075 |
| 2 | type I interferon signaling pathway | 1.77E−15 | 8.35 | 3.21E−12 |
| 3 | negative regulation of viral genome replication | 1.05E−08 | 7.79 | 1.89E−05 |
| 4 | interferon-gamma-mediated signaling pathway | 2.42E−12 | 6.90 | 4.38E−09 |
| 5 | response to virus | 3.60E−14 | 5.87 | 6.51E−11 |
| 6 | defense response to virus | 3.26E−13 | 4.59 | 5.90E−10 |
| 7 | platelet degranulation | 1.36E−07 | 4.32 | 2.46E−04 |
| 8 | leukocyte migration | 2.03E−06 | 3.65 | 0.003678 |
| 9 | platelet activation | 1.42E−05 | 3.49 | 0.025641 |
| 10 | inflammatory response | 6.76E−12 | 3.00 | 1.22E−08 |
| 11 | immune response | 8.61E−13 | 2.96 | 1.56E−09 |
| 12 | innate immune response | 4.29E−08 | 2.43 | 7.77E−05 |

TABLE 16

A list of transcription factors downregulated in NoTED group

| Gene | Log2Fold Change | pvalue | padj |
|---|---|---|---|
| GATA1 | −1.526 | 4.08E−09 | 7.17E−07 |
| KLF1 | −1.63 | 3.28E−07 | 1.57E−05 |
| TAL1 | −1.339 | 3.81E−08 | 3.19E−06 |
| ZFPM1 | −0.842 | 0.000103224 | 0.001238881 |
| LMO2 | −0.405 | 0.001859348 | 0.011529232 |

TABLE 17

A list of predictor genes and the number of times that gene was used as predictor. These genes were identified using leave-one-out cross validation using Weighted Voting methods.

| Predictor Gene | Number of times Used for Prediction |
|---|---|
| CCT2 | 42 |
| PGAM5 | 42 |
| EIF2B3 | 42 |
| GTPBP4 | 42 |
| CCDC138 | 42 |
| CCDC97 | 42 |
| PPT2 | 42 |
| TMEM123 | 42 |
| STX16 | 42 |
| HPCAL1 | 42 |
| BECN1 | 42 |
| ZNF620 | 42 |
| DDX1 | 42 |
| TRPS1 | 42 |
| RG9MTD1 | 42 |
| CDS2 | 42 |
| LOC100652878 | 42 |
| USP14 | 42 |
| ADAM10 | 42 |
| GNB1 | 42 |
| FARSB | 42 |
| NUP107 | 42 |
| TF | 42 |
| YPEL2 | 42 |
| WIPF1 | 42 |
| PAK1IP1 | 42 |
| AP2A2 | 42 |
| MICA | 42 |
| UBQLN2 | 42 |
| CXCL12 | 42 |
| TGFB1 | 42 |
| TGS1 | 42 |
| SCAMP2 | 42 |
| ZFAND3 | 42 |
| CSE1L | 42 |
| CASC4 | 42 |
| HDAC5 | 42 |
| KCTD18 | 42 |
| HSPD1 | 42 |
| ZNF319 | 42 |
| DENND5A | 42 |
| METAP2 | 42 |
| AKR1C3 | 42 |
| HLTF | 42 |
| COQ3 | 42 |
| SAMM50 | 42 |
| UBE2R2 | 42 |
| SELPLG | 42 |
| MSH2 | 42 |
| UBE2Q1 | 42 |
| SH3BGRL3 | 42 |
| SNHG13 | 41 |
| NAA50 | 41 |
| KLHL6 | 41 |
| ITGA5 | 41 |
| HSP90AA1 | 41 |
| GEMIN5 | 41 |
| USP35 | 40 |
| LARP4 | 40 |
| TCP1 | 40 |
| FLI1 | 39 |
| ZNF688 | 39 |
| TSR1 | 39 |
| DEF6 | 39 |
| SMPD1 | 39 |
| COPS3 | 38 |
| PPP2R1B | 38 |
| DDB1 | 38 |
| HAUS6 | 38 |
| ZC3H7A | 37 |
| PSMD14 | 37 |
| RHOBTB3 | 37 |
| DKC1 | 37 |

TABLE 17-continued

A list of predictor genes and the number of times that gene was used as predictor. These genes were identified using leave-one-out cross validation using Weighted Voting methods.

| Predictor Gene | Number of times Used for Prediction |
|---|---|
| C9orf89 | 36 |
| MRPS9 | 36 |
| FKBPL | 36 |
| DDX58 | 35 |

TABLE 18

A list of genes identified using VST or TPM normalization with WeightedVoting methods; or TPM with RandomForest method, indicated with an "yes" in the respective column. Log2Fold change, base mean count of reads in each of TED group, and the padj value for each genes is presented.

| | WeightedVoting | | | Base Mean Counts | | log2Fold | |
|---|---|---|---|---|---|---|---|
| Id | VST | TPM | RandomForest | TED | NoTED | Change | padj |
| ABR | Yes | | | 5209 | 7152 | 0.457 | 7.64E-05 |
| ADAM10 | Yes | Yes | | 4131 | 6150 | 0.574 | 1.77E-06 |
| AKR1C3 | Yes | Yes | Yes | 1777 | 602 | -1.562 | 4.64E-09 |
| ANTXR2 | | Yes | | 3646 | 5177 | 0.506 | 0.000197327 |
| AP2A2 | Yes | | | 2101 | 2551 | 0.28 | 1.54E-06 |
| ATAD3A | | | Yes | 1582 | 896 | -0.82 | 7.94E-07 |
| ATP6V0E1 | | Yes | | 4253 | 5366 | 0.335 | 0.002382794 |
| C1orf135 | | | Yes | 413 | 169 | -1.289 | 7.65E-07 |
| C3orf26 | | | Yes | 680 | 379 | -0.842 | 1.09E-06 |
| CASC4 | Yes | Yes | | 2326 | 3011 | 0.372 | 1.34E-05 |
| CCDC138 | Yes | Yes | Yes | 313 | 177 | -0.816 | 7.85E-09 |
| CCNB1 | | | Yes | 3438 | 1306 | -1.396 | 5.24E-06 |
| CCT2 | Yes | | Yes | 6971 | 3953 | -0.818 | 2.36E-08 |
| CDS2 | Yes | | | 3066 | 4149 | 0.436 | 3.44E-05 |
| CELF2 | Yes | | | 11522 | 15938 | 0.468 | 0.000150884 |
| CHEK2 | | | Yes | 875 | 540 | -0.697 | 8.41E-06 |
| CHL1 | | | Yes | 162 | 36 | -2.171 | 1.15E-07 |
| COPS3 | Yes | Yes | Yes | 3890 | 2448 | -0.668 | 2.40E-07 |
| COQ3 | | | Yes | 288 | 151 | -0.932 | 4.34E-08 |
| CSE1L | | | Yes | 4492 | 2695 | -0.737 | 6.87E-08 |
| DDX1 | Yes | | Yes | 4237 | 2591 | -0.71 | 7.85E-09 |
| DDX59 | | Yes | | 1073 | 1272 | 0.245 | 0.001325073 |
| DENND5A | Yes | Yes | | 4397 | 6699 | 0.607 | 1.71E-06 |
| DRG1 | Yes | Yes | | 1833 | 1389 | -0.401 | 1.57E-05 |
| DTYMK | | Yes | | 1254 | 659 | -0.928 | 1.70E-06 |
| EEF1E1 | | | Yes | 368 | 226 | -0.704 | 1.91E-05 |
| EIF2B3 | Yes | Yes | Yes | 799 | 398 | -1.003 | 4.03E-10 |
| ESCO2 | | | Yes | 889 | 316 | -1.491 | 3.93E-07 |
| EXO1 | | | Yes | 1367 | 529 | -1.368 | 2.85E-06 |
| FAM195A | | Yes | | 750 | 471 | -0.671 | 1.28E-06 |
| FAT1 | | | Yes | 168 | 27 | -2.605 | 4.29E-06 |
| FKBPL | Yes | Yes | Yes | 490 | 254 | -0.948 | 2.62E-07 |
| FLI1 | | Yes | | 7066 | 9416 | 0.414 | 6.42E-05 |
| FMO2 | | | Yes | 104 | 20 | -2.343 | 1.39E-07 |
| FRZB | | | Yes | 86 | 16 | -2.439 | |
| FUT1 | | | Yes | 692 | 90 | -2.941 | 1.52E-10 |
| GMNN | | Yes | | 1391 | 668 | -1.058 | 9.70E-06 |
| GTPBP4 | Yes | | | 2137 | 1433 | -0.577 | 1.15E-08 |
| HAT1 | | | Yes | 2613 | 1827 | -0.516 | 0.000202524 |
| HDAC5 | Yes | | | 2381 | 3340 | 0.488 | 1.04E-06 |
| HMMR | | | Yes | 2454 | 975 | -1.332 | 2.53E-05 |
| HPCAL1 | Yes | | | 1413 | 1980 | 0.487 | 1.63E-06 |
| HSP90AA1 | Yes | Yes | Yes | 53444 | 29419 | -0.861 | 3.74E-07 |
| HSPD1 | Yes | Yes | Yes | 13825 | 7079 | -0.966 | 7.85E-09 |
| IRX1 | | | Yes | 22 | 1 | -4.195 | 9.48E-09 |
| ITGAV | Yes | Yes | | 770 | 1071 | 0.475 | 0.000439387 |
| ITPR2 | Yes | | | 2922 | 3617 | 0.308 | 0.000712884 |
| KCTD18 | Yes | | | 1019 | 1220 | 0.261 | 4.71E-05 |
| KLHL6 | Yes | | | 2616 | 3547 | 0.439 | 1.18E-05 |
| LAMP1 | | Yes | | 7737 | 9345 | 0.272 | 0.000329941 |
| LAPTM5 | | Yes | | 39365 | 52931 | 0.427 | 0.000667833 |
| LOC100505758 | | | Yes | 608 | 394 | -0.626 | 5.89E-06 |

TABLE 18-continued

A list of genes identified using VST or TPM normalization with WeightedVoting methods; or TPM with RandomForest method, indicated with an "yes" in the respective column. Log2Fold change, base mean count of reads in each of TED group, and the padj value for each genes is presented.

| | WeightedVoting | | | Base Mean Counts | | log2Fold | |
|---|---|---|---|---|---|---|---|
| Id | VST | TPM | RandomForest | TED | NoTED | Change | padj |
| LOC100506321 | Yes | Yes | | 706 | 1129 | 0.678 | 3.25E−05 |
| LOC100506639 | Yes | | | 237 | 306 | 0.367 | 0.000534426 |
| LOC100652878 | Yes | Yes | Yes | 1017 | 617 | −0.721 | 1.53E−07 |
| MARVELD2 | | | Yes | 96 | 23 | −2.035 | 1.13E−09 |
| MAX | Yes | | | 4199 | 6179 | 0.557 | 5.33E−05 |
| METAP2 | | | Yes | 7205 | 3583 | −1.008 | 2.67E−08 |
| METTL5 | | Yes | | 1278 | 927 | −0.462 | 5.23E−05 |
| MICA | | Yes | | 580 | 812 | 0.487 | 2.53E−05 |
| MRPL1 | | | Yes | 989 | 575 | −0.783 | 3.72E−07 |
| MRPL22 | | | Yes | 822 | 533 | −0.626 | 1.67E−05 |
| MRPL47 | | Yes | Yes | 1131 | 793 | −0.512 | 1.63E−05 |
| MSH2 | Yes | Yes | Yes | 2683 | 1590 | −0.755 | 2.67E−08 |
| NAA50 | Yes | | | 6978 | 4839 | −0.528 | 6.21E−07 |
| NDUFAB1 | | Yes | Yes | 1477 | 988 | −0.58 | 3.70E−06 |
| NDUFB6 | | Yes | Yes | 927 | 552 | −0.746 | 9.03E−06 |
| NUP107 | Yes | | | 2973 | 2090 | −0.508 | 1.16E−08 |
| NUP37 | | | Yes | 1168 | 700 | −0.74 | 1.78E−05 |
| ODC1 | Yes | | Yes | 6367 | 3477 | −0.873 | 3.06E−07 |
| PAK1IP1 | Yes | | Yes | 1056 | 592 | −0.835 | 2.36E−08 |
| PELI2 | | Yes | | 1822 | 2661 | 0.546 | 0.000282154 |
| PGAM5 | Yes | | | 1547 | 1079 | −0.519 | 1.15E−07 |
| POLR3K | | Yes | Yes | 550 | 361 | −0.607 | 1.17E−06 |
| PPA2 | | | Yes | 1939 | 1207 | −0.684 | 1.19E−05 |
| PPT2 | Yes | Yes | | 924 | 333 | −1.473 | 2.33E−09 |
| PSMC1 | | Yes | | 2674 | 2043 | −0.388 | 0.000337328 |
| PSMD14 | Yes | Yes | Yes | 2017 | 1249 | −0.692 | 2.37E−07 |
| PUS1 | Yes | | | 1472 | 1040 | −0.501 | 2.28E−06 |
| RANGAP1 | Yes | | | 4801 | 3246 | −0.565 | 5.24E−06 |
| RG9MTD1 | Yes | | | 943 | 562 | −0.745 | 2.85E−08 |
| SAMM50 | Yes | | | 2064 | 1407 | −0.552 | 2.62E−07 |
| SELPLG | Yes | Yes | | 8348 | 13838 | 0.729 | 1.63E−06 |
| SLCO3A1 | | Yes | | 1781 | 2654 | 0.575 | 5.25E−05 |
| SLIRP | | Yes | | 821 | 474 | −0.794 | 2.02E−06 |
| SNRPE | | Yes | Yes | 1991 | 1273 | −0.645 | 6.40E−06 |
| SULT1B1 | | Yes | | 348 | 774 | 1.155 | 2.27E−05 |
| SVEP1 | | | Yes | 99 | 12 | −3.009 | 1.62E−10 |
| TCP1 | Yes | | | 8321 | 5679 | −0.551 | 6.80E−07 |
| TIMM23 | | | Yes | 1053 | 692 | −0.606 | 6.60E−06 |
| TMEM123 | Yes | Yes | Yes | 12076 | 18495 | 0.615 | 3.76E−08 |
| TMOD2 | Yes | | | 969 | 1626 | 0.747 | 0.000767602 |
| TMX4 | | Yes | | 1990 | 2602 | 0.387 | 0.000319829 |
| TOM1 | | Yes | | 2096 | 2734 | 0.384 | 0.003167342 |
| TRPS1 | Yes | Yes | | 1146 | 2094 | 0.869 | 4.71E−06 |
| UBE2T | | Yes | | 960 | 372 | −1.367 | 8.24E−07 |
| UBQLN2 | Yes | | | 1616 | 2223 | 0.46 | 3.72E−06 |
| UBXN10 | | | Yes | 309 | 111 | −1.474 | 1.02E−07 |
| VBP1 | | Yes | Yes | 2674 | 1761 | −0.602 | 2.43E−05 |
| VPS8 | | Yes | | 2042 | 2860 | 0.486 | 0.000532548 |
| WIPF1 | Yes | | | 12136 | 18727 | 0.626 | 7.14E−06 |
| YBX2 | | | Yes | 105 | 25 | −2.05 | 3.68E−07 |
| YPEL2 | Yes | Yes | | 1774 | 2787 | 0.652 | 5.17E−05 |
| YPEL3 | | Yes | | 3096 | 4370 | 0.497 | 4.70E−05 |
| ZC3H7A | Yes | | | 3284 | 3841 | 0.226 | 0.000114963 |
| ZFAND3 | | Yes | | 2728 | 3563 | 0.385 | 1.57E−05 |
| ZNF319 | Yes | | | 992 | 1402 | 0.499 | 1.36E−05 |
| ZYX | | Yes | | 16455 | 23143 | 0.492 | 0.00042208 |

TABLE 19

List of 79 genes used for validation using qPCR. Average expression of these genes in TED+ and TED−, fold change, and pvalue on a t-test are provided.

| gene | P value t-test | FoldChange | Average expresesion TED− | Average expresesion TED+ |
|---|---|---|---|---|
| ABR | 0.0001 | 1.603 | 2.94 | 3.62 |
| ADAM10 | 0.0010 | 1.745 | 2.38 | 3.18 |
| AKR1C3 | 0.0007 | 0.471 | 1.35 | 0.27 |
| AP2A2 | 0.0295 | 1.263 | 4.88 | 5.22 |
| ATP6V0E1 | 0.0000 | 1.839 | −2.38 | −1.50 |
| CASC4 | 0.0004 | 1.534 | 0.14 | 0.76 |
| CCDC138 | 0.0100 | 0.719 | 2.47 | 1.99 |
| CCT2 | 0.1777 | 0.869 | −0.83 | −1.03 |
| CDS2 | 0.0667 | 1.310 | 2.67 | 3.06 |
| CELF2 | 0.0028 | 1.769 | 2.59 | 3.41 |
| COPS3 | 0.1076 | 0.860 | −2.93 | −3.14 |
| DDX1 | 0.1332 | 0.896 | 1.05 | 0.89 |
| DDX59 | 0.0006 | 1.648 | 0.54 | 1.26 |
| DENND5A | 0.0025 | 1.832 | 3.93 | 4.80 |
| DTYMK | 0.0514 | 0.765 | 1.67 | 1.28 |
| EIF2B3 | 0.0373 | 0.743 | 2.97 | 2.54 |
| FKBPL | 0.0130 | 0.699 | 6.84 | 6.32 |
| FLI1 | 0.0000 | 1.507 | 0.09 | 0.69 |
| GMNN | 0.0018 | 0.613 | −2.94 | −3.65 |
| HDAC5 | 0.6267 | 1.891 | 18.76 | 19.68 |
| HPCAL1 | 0.0061 | 1.681 | 3.18 | 3.93 |
| HSP90AA1 | 0.2780 | 0.877 | −4.25 | −4.44 |
| HSPD1 | 0.0325 | 0.779 | −0.47 | −0.83 |
| ITGAV | 0.0006 | 1.818 | 0.31 | 1.17 |
| ITPR2 | 0.0631 | 1.351 | 4.02 | 4.45 |
| KCTD18 | 0.0086 | 1.362 | 2.42 | 2.87 |
| LAMP1 | 0.0027 | 1.589 | 1.65 | 2.32 |
| LAPTM5 | 0.0045 | 1.804 | −1.79 | −0.94 |
| LOC100506639 | 0.0849 | 1.355 | 6.99 | 7.43 |
| MAX | 0.0041 | 1.680 | −1.63 | −0.88 |
| MCRIP2 (FAM195A) | 0.7757 | 0.948 | 8.54 | 8.46 |
| MICA | 0.0007 | 2.120 | −0.25 | 0.83 |
| MSH2 | 0.3322 | 0.855 | 1.64 | 1.42 |
| NAA50 | 0.6891 | 0.960 | −2.53 | −2.59 |
| ODC1 | 0.2394 | 0.853 | 0.89 | 0.66 |
| PAK1IP1 | 0.0149 | 0.743 | −0.70 | −1.13 |
| PELI2 | 0.0000 | 1.885 | 1.84 | 2.76 |
| PPT2 | 0.0001 | 0.394 | 10.26 | 8.91 |
| PUS1 | 0.2189 | 0.879 | 4.05 | 3.86 |
| SAMM50 | 0.1201 | 0.843 | 1.53 | 1.28 |
| SELPLG | 0.0000 | 2.076 | −3.31 | −2.26 |
| SLCO3A1 | 0.0002 | 1.917 | 3.51 | 4.45 |
| SULT1B1 | 0.0000 | 2.703 | 0.86 | 2.30 |
| TCP1 | 0.1998 | 0.884 | −2.45 | −2.62 |
| TMEM123 | 0.0000 | 1.810 | −3.58 | −2.73 |
| TMOD2 | 0.0195 | 2.489 | 2.60 | 3.92 |
| TMX4 | 0.0011 | 1.443 | 2.81 | 3.34 |
| TOM1 | 0.0000 | 1.893 | 1.36 | 2.28 |
| TRMT10C (RG9MTD1) | 0.4523 | 0.912 | −0.68 | −0.81 |
| TRPS1 | 0.0033 | 1.769 | −0.11 | 0.71 |
| UBE2T | 0.0009 | 0.556 | −0.20 | −1.05 |
| UBQLN2 | 0.0018 | 1.611 | −2.61 | −1.92 |
| VPS8 | 0.0017 | 1.587 | 3.48 | 4.14 |
| WIPF1 | 0.0018 | 1.986 | 0.89 | 1.88 |
| YPEL2 | 0.0027 | 2.004 | 3.79 | 4.79 |
| YPEL3 | 0.0000 | 1.883 | 1.94 | 2.85 |
| ZC3H7A | 0.0014 | 1.475 | −0.06 | 0.50 |
| ZFAND3 | 0.0004 | 1.609 | −1.15 | −0.47 |
| ZNF319 | 0.0137 | 1.616 | 3.58 | 4.27 |
| ZYX | 0.0012 | 2.767 | 12.27 | 13.74 |
| ANTXR2 | 0.1367 | 9.726 | 8.95 | 12.23 |
| GTPBP4 | 0.8200 | 0.973 | −0.58 | −0.62 |
| LOC100506321 | 0.0131 | 1.413 | 2.37 | 2.86 |
| NUP107 | 0.4256 | 0.905 | 2.30 | 2.16 |
| DRG1 | 0.3095 | 1.160 | 2.20 | 2.42 |
| KLHL6 | 0.2498 | 5.032 | 9.26 | 11.59 |
| LOC100652878 | 0.2931 | 0.862 | −2.68 | −2.89 |
| METTL5 | 0.6960 | 0.915 | −3.40 | −3.53 |
| MRPL47 | 0.5203 | 0.906 | −3.83 | −3.97 |
| NDUFAB1 | 0.8361 | 0.980 | −3.39 | −3.42 |
| NDUFB6 | 0.2800 | 0.880 | −3.15 | −3.33 |
| PGAM5 | 0.5188 | 1.885 | 10.52 | 11.44 |
| POLR3K | 0.5640 | 1.058 | 0.17 | 0.25 |
| PSMC1 | 0.0434 | 1.311 | 0.84 | 1.23 |
| PSMD14 | 0.4341 | 0.888 | −2.87 | −3.04 |
| RANGAP1 | 0.2329 | 0.275 | 12.50 | 10.63 |
| SLIRP | 0.2621 | 0.827 | −5.46 | −5.73 |
| SNRPE | 0.4789 | 0.881 | −6.01 | −6.19 |
| VBP1 | 0.6508 | 0.946 | −3.64 | −3.72 |

REFERENCES

Bejar et al. Validation of a prognostic model and the impact of mutations in patients with lower-risk myelodysplastic syndromes. *J Clin Oncol.* 2012; 30(27):3376-3382.

Blikstad et al. Synthesis and assembly of spectrin during avian erythropoiesis: stoichiometric assembly but unequal synthesis of alpha and beta spectrin. *Cell.* 1983; 32(4): 1081-1091.

Chang et al. Asynchronous synthesis of erythrocyte membrane proteins. *Proc Natl Acad Sci USA.* 1976; 73(9): 3206-3210.

Chen et al. Resolving the distinct stages in erythroid differentiation based on dynamic changes in membrane protein expression during erythropoiesis. *Proc Natl Acad Sci USA.* 2009; 106(41):17413-17418.

Greenberg et al. Revised international prognostic scoring system for myelodysplastic syndromes. *Blood.* 2012; 120 (12):2454-2465.

Gronowicz et al. Maturation of the reticulocyte in vitro. *J Cell Sci.* 1984; 71:177-197.

Hanspal et al. Asynchronous synthesis of membrane skeletal proteins during terminal maturation of murine erythroblasts. *Blood.* 1992; 80(2):530-539.

Hu et al. Isolation and functional characterization of human erythroblasts at distinct stages: implications for understanding of normal and disordered erythropoiesis in vivo. *Blood.* 2013; 121(16):3246-3253.

Liu and Mohandas, An X. Membrane assembly during erythropoiesis. *Curr Opin Hematol.* 2011; 18(3):133-138.

Malcovati et al. SF3B1 mutation identifies a distinct subset of myelodysplastic syndrome with ring sideroblasts. *Blood.* 2015; 126(2):233-241.

Mangaonkar et al. Prognostic interaction between bone marrow morphology and SF3B1 and ASXL1 mutations in myelodysplastic syndromes with ring sideroblasts. *Blood Cancer J.* 2018; 8(2):18.

Patnaik et al. SF3B1 mutations are prevalent in myelodysplastic syndromes with ring sideroblasts but do not hold independent prognostic value. *Blood.* 2012; 119(2):569-572.

Peters et al. Changing patterns in cytoskeletal mRNA expression and protein synthesis during murine erythropoiesis in vivo. *Proc Natl Acad Sci USA.* 1992; 89(13): 5749-5753

Pomares et al. Validation of the Low Risk Prognostic Scoring System (LR-PSS) in Patients with VERY Low, Low and Intermediate Risk IPSS-R Myelodysplastic Syndrome. Results from a Single Center. *Blood.* 2015; 126(23):2902-2902.

Raza and Galil, The genetic basis of phenotypic heterogeneity in myelodysplastic syndromes. *Nat Rev Cancer.* 2012; 12(12):849-859.

Shiozawa et al. Gene expression and risk of leukemic transformation in myelodysplasia. *Blood.* 2017; 130(24): 2642-2653.

Wu et al. The clinical implication of SRSF2 mutation in patients with myelodysplastic syndrome and its stability during disease evolution. *Blood.* 2012; 120(15):3106-3111.

Zhang et al. Disease-associated mutation in SRSF2 misregulates splicing by altering RNA-binding affinities. *Proc Natl Acad Sci USA.* 2015; 112(34):E4726-4734.

The invention claimed is:

1. A method of treating myelodyplastic syndrome (MDS) in a subject in need thereof, comprising:
   a. assaying gene expression levels of PPT2, AKR1C3, and SELPLG in a sample from the subject with MDS to obtain a test expression profile;
   b. comparing the test expression profile of the subject with MDS with a reference expression profile of the same genes wherein the reference expression profile comprises gene expression levels of the same genes that are indicative of either a TED+ profile or a TED− profile;
   c. detecting that the gene expression levels of the genes in the test expression profile are different than the gene expression levels of the same genes in the reference expression profile that is indicative of a TED+ profile and/or detecting gene expression levels of the genes in the test expression profile are the same as the gene expression levels of the same genes in the reference expression profile that is indicative of a TED− profile;
   d. classifying the subject as having a TED− profile and severe MDS; and
   e. treating the subject with treatment selected from the group consisting of:
   hematopoetic stem cell transplant; bone marrow transplant; administering hypomethylating agents, chemotherapeutic agents or combinations thereof, wherein said treatment is aggressive and more effectively treats severe MDS.

2. The method of claim 1, wherein the sample from the subject is from the bone marrow of the subject.

* * * * *

UNITED STATES PATENT AND TRADEMARK OFFICE
CERTIFICATE OF CORRECTION

| | |
|---|---|
| PATENT NO. | : 11,186,877 B2 |
| APPLICATION NO. | : 16/223942 |
| DATED | : November 30, 2021 |
| INVENTOR(S) | : Azra Raza, Abdullah Mahmood Ali and Naomi Galili |

It is certified that error appears in the above-identified patent and that said Letters Patent is hereby corrected as shown below:

In the Specification

Column 1 Lines 16-19, should read:
"STATEMENT OF GOVERNMENT SUPPORT
This invention was made with government support under grant numbers DK100810 and DK32094 awarded by the National Institutes of Health. The government has certain rights in this invention.".

Signed and Sealed this
First Day of August, 2023

Katherine Kelly Vidal
*Director of the United States Patent and Trademark Office*